(12) United States Patent
Treon et al.

(10) Patent No.: US 10,526,660 B2
(45) Date of Patent: Jan. 7, 2020

(54) METHODS FOR EVALUATING AND TREATING WALDENSTROM'S MACROGLOBULINEMIA

(71) Applicant: Dana-Farber Cancer Institute, Inc., Boston, MA (US)

(72) Inventors: Steven P. Treon, Jamaica Plain, MA (US); Zachary Hunter, Jamaica Plain, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 236 days.

(21) Appl. No.: 15/021,323

(22) PCT Filed: Sep. 12, 2014

(86) PCT No.: PCT/US2014/055386
§ 371 (c)(1),
(2) Date: Mar. 11, 2016

(87) PCT Pub. No.: WO2015/038887
PCT Pub. Date: Mar. 19, 2015

(65) Prior Publication Data
US 2016/0222465 A1 Aug. 4, 2016

Related U.S. Application Data

(60) Provisional application No. 61/889,150, filed on Oct. 10, 2013, provisional application No. 61/877,009, filed on Sep. 12, 2013.

(51) Int. Cl.
| | | |
|---|---|---|
| *A61K 39/395* | (2006.01) | |
| *C12Q 1/6886* | (2018.01) | |
| *C12Q 1/6883* | (2018.01) | |
| *A61K 31/519* | (2006.01) | |
| *A61K 45/06* | (2006.01) | |

(52) U.S. Cl.
CPC .......... *C12Q 1/6886* (2013.01); *A61K 31/519* (2013.01); *A61K 45/06* (2013.01); *C12Q 1/6883* (2013.01); *C12Q 2600/106* (2013.01); *C12Q 2600/112* (2013.01); *C12Q 2600/156* (2013.01); *C12Q 2600/158* (2013.01)

(58) Field of Classification Search
CPC .. C12Q 1/6886; C12Q 1/6883; A61K 31/519; A61K 45/06
See application file for complete search history.

(56) References Cited

U.S. PATENT DOCUMENTS

| | | |
|---|---|---|
| 2004/0137489 A1 | 7/2004 | Shaughnessy |
| 2009/0156469 A1 | 6/2009 | Ghobrial et al. |
| 2010/0009350 A1 | 1/2010 | Chow |
| 2010/0216115 A1 | 8/2010 | Yan et al. |
| 2012/0065201 A1 | 3/2012 | Honigberg et al. |
| 2012/0071497 A1 | 3/2012 | Buggy et al. |
| 2014/0249142 A1 | 9/2014 | Treon |
| 2016/0304958 A1 | 10/2016 | Treon et al. |
| 2017/0333436 A1 | 11/2017 | Treon et al. |

FOREIGN PATENT DOCUMENTS

| | | | | |
|---|---|---|---|---|
| EP | 2 878 601 A1 | 6/2015 | | |
| WO | WO 2006/067091 A1 | 6/2006 | | |
| WO | WO 2008060367 A2 * | 5/2008 | ....... | A61K 47/48384 |
| WO | WO 2013/006443 A2 | 1/2013 | | |
| WO | WO 2013/071068 A2 | 5/2013 | | |
| WO | WO 2015/038887 A1 | 3/2015 | | |

OTHER PUBLICATIONS

Hunter et al., (Hematol. Oncol. Jun. 2013. 31(S1):127. Abstract 93).*
Treon et al., (Hematol. Oncol. Jun. 2013. 31(S1):119. Abstract 67).*
Treon et al., (Hematol. Oncol. Jun. 2013. 31(S1):146. Abstract 150) (cited on Applicant's IDS of Nov. 28, 2016).*
Cao et al., (Blood. Nov. 16, 2012;120(12):2715. Abstract from 54th ASH Annual Meeting).*
Campath (alemtuzumab) Package Insert. FDA. ePub Sep. 26, 2003. www.accessdata.fda.gov/drugsatfda_docs/lanel/2001/alemmil050701LB.htm. Issued May 2001. 11 pages. Last Accessed Apr. 4, 2018. (Year: 2003).*
Trademark Electronic Search System (TESS). CAMPATH mark. Typed Drawing. May 21, 1991. 2nd Renewal Apr. 24, 2013. Last Accessed Apr. 4, 2018. 2 pages. (Year: 1991).*
Dasmahaptra et al., (Br J Haematol. Apr. 2013; 161(1):43-56. ePub Jan. 30, 2013; Abstract Only) (Year: 2013).*
Extended European Search Report for EP12807230.3 dated Feb. 2, 2015.
Invitation to Pay Additional Fees for PCT/US2012/044956 mailed Oct. 1, 2012.
International Search Report and Written Opinion for PCT/US2012/044956 dated Dec. 17, 2012.
International Preliminary Report on Patentability for PCT/US2012/044956 dated Jan. 16, 2014.
International Search Report and Written Opinion for PCT/US2014/055386 dated Dec. 23, 2014.
International Preliminary Report on Patentability for PCT/US2014/055386 dated Mar. 24, 2016.
International Search Report and Written Opinion for PCT/US2014/068579 dated Mar. 3, 2015.
International Preliminary Report on Patentability for PCT/US2014/068579 dated Jun. 16, 2016.
Advani et al., Bruton tyrosine kinase inhibitor ibrutinib (PCI-32765) has significant activity in patients with relapsed/refractory B-cell malignancies. J Clin Oncol. Jan. 1, 2013;31(1):88-94. doi:10.1200/JCO.2012.42.7906. Epub Oct. 8, 2012.

(Continued)

*Primary Examiner* — Michael D Pak
(74) *Attorney, Agent, or Firm* — Wolf, Greenfield & Sacks, P.C.

(57) ABSTRACT

Methods for evaluating and treating Waldenstrom's macroglobulinemia are provided.

22 Claims, 23 Drawing Sheets
Specification includes a Sequence Listing.

(56) References Cited

OTHER PUBLICATIONS

Anderson et al., Multiple myeloma, version 1.2013. J Natl Compr Canc Netw. Jan. 1, 2013;11(1):11-7.
Arcaini et al., Distinctive clinical and histological features of Waldenström's macroglobulinemia and splenic marginal zone lymphoma. Clin Lymphoma Myeloma Leuk. Feb. 2011;11(1):103-5. doi:10.3816/CLML.2011.n.020.
Argentou et al., Rapid detection of MYD88-L265P mutation by PCR-RFLP in B-cell lymphoproliferative disorders. Leukemia. Feb. 2014;28(2):447-9. doi: 10.1038/leu.2013.294. Epub Oct. 18, 2013.
Balabanian et al., WHIM syndromes with different genetic anomalies are accounted for by impaired CXCR4 desensitization to CXCL12. Blood. Mar. 15, 2005;105(6):2449-57. Epub Nov. 9, 2004.
Bam et al., Role of Bruton's tyrosine kinase in myeloma cell migration and induction of bone disease. Am J Hematol. Jun. 2013;88(6):463-71. doi: 10.1002/ajh.23433. Epub Mar. 28, 2013.
Berger et al., Clinicopathologic features of Waldenstrom's macroglobulinemia and marginal zone lymphoma: are they distinct or the same entity? Clin Lymphoma. Mar. 2005;5(4):220-4. Abstract.
Bergsagel et al., Comprehensive identification of somatic mutations in chronic lymphocytic leukemia. Cancer Cell. Jul. 12, 2011;20(1):5-7. doi:10.1016/j.ccr.2011.06.023.
Bohers et al., Targetable activating mutations are very frequent in GCB and ABC diffuse large B-cell lymphoma. Genes Chromosomes Cancer. Feb. 2014;53(2):144-53. doi:10.1002/gcc.22126. Epub Nov. 5, 2013.
Brikos et al., Mass spectrometric analysis of the endogenous type I interleukin-1 (IL-1) receptor signaling complex formed after IL-1 binding identifies IL-1RAcP, MyD88, and IRAK-4 as the stable components. Mol Cell Proteomics. Sep. 2007;6(9):1551-9. Epub May 15, 2007.
Busillo et al., Regulation of CXCR4 signaling. Biochim Biophys Acta. Apr. 2007;1768(4):952-63. Epub Nov. 10, 2006.
Busillo et al., Site-specific phosphorylation of CXCR4 is dynamically regulated by multiple kinases and results in differential modulation of CXCR4 signaling. J Biol Chem. Mar. 5, 2010;285(10):7805-17. doi: 10.1074/jbc.M109.091173. Epub Jan. 4, 2010.
Cao et al., CXCR4 WHIM-like frameshift and nonsense mutations promote ibrutinib resistance but do not supplant MYD88(L265P)-directed survival signalling in Waldenström macroglobulinaemia cells. Br J Haematol. Mar. 2015;168(5):701-7. doi: 10.1111/bjh.13200. Epub Nov. 5, 2014.
Cao et al., The WHIM-like CXCR4(S338X) somatic mutation activates AKT and ERK, and promotes resistance to ibrutinib and other agents used in the treatment of Waldenstrom's Macroglobulinemia. Leukemia. Jan. 2015;29(1):169-76. doi: 10.1038/leu.2014.187. Epub Jun. 10, 2014.
Cao et al., Whole Genome Sequencing Identifies Recurring Somatic Mutations in the C-Terminal Domain of CXCR4, Including a Gain of Function Mutation in Waldenstrom's Macroglobinemia. Blood. 2012;120: Abstract 2715.
Carnevali et al., Computational techniques for human genome resequencing using mated gapped reads. J Comput Biol. Mar. 2012;19(3):279-92. doi: 10.1089/cmb.2011.0201. Epub Dec. 16, 2011.
Chen, Treatment for Waldenstrom's macroglobulinemia. Ann Oncol. Apr. 2004;15(4):550-8.
Cheng et al., Binding of Bruton's tyrosine kinase to Fyn, Lyn, or Hck through a Src homology 3 domain-mediated interaction. Proc Natl Acad Sci U S A. Aug. 16, 1994;91(17):8152-5.
Chng et al., Gene-expression profiling of Waldenstrom macroglobulinemia reveals a phenotype more similar to chronic lymphocytic leukemia than multiple myeloma. Blood. Oct. 15, 2006;108(8):2755-63. Epub Jun. 27, 2006.
Davies et al., Preclinical pharmacology of AZD5363, an inhibitor of AKT: pharmacodynamics, antitumor activity, and correlation of monotherapy activity with genetic background. Mol Cancer Ther. Apr. 2012;11(4):873-87. doi: 10.1158/1535-7163.MCT-11-0824-T. Epub Jan. 31, 2012.
Ditzel et al., Establishment of BCWM.1 cell line for Waldenström's macroglobulinemia with productive in vivo engraftment in SCID-hu mice. Exp Hematol. Sep. 2007;35(9):1366-75.
Dotta et al., Clinical and genetic features of Warts, Hypogammaglobulinemia, Infections and Myelokathexis (WHIM) syndrome. Curr Mol Med. Jun. 2011;11(4):317-25.
Drmanac et al., Human genome sequencing using unchained base reads on self-assembling DNA nanoarrays. Science. Jan. 1, 2010;327(5961):78-81.
Evans et al., Inhibition of Btk with CC-292 provides early pharmacodynamic assessment of activity in mice and humans. J Pharmacol Exp Ther. Aug. 2013;346(2):219-28. doi:10.1124/jpet.113.203489. Epub May 24, 2013.
Farré et al., Identification of patterns in biological sequences at the ALGGEN server: PROMO and MALGEN. Nucleic Acids Res. Jul. 1, 2003;31(13):3651-3.
Futahashi et al., Separate elements are required for ligand-dependent and -independent internalization of metastatic potentiator CXCR4. Cancer Sci. Mar. 2007;98(3):373-9.
Gachard et al., IGHV gene features and MYD88 L265P mutation separate the three marginal zone lymphoma entities and Waldenström macroglobulinemia/lymphoplasmacytic lymphomas. Leukemia. Jan. 2013;27(1):183-9. doi: 10.1038/leu.2012.257. Epub Sep. 4, 2012.
Gay et al., Assembly and localization of Toll-like receptor signalling complexes. Nat Rev Immunol. Aug. 2014;14(8):546-58. doi: 10.1038/nri3713.
Genbank Submission; NIH/NCBI, Accession No. NM_001008540. Micucci et al., Mar. 18, 2016.
Gertz et al., Waldenström's macroglobulinemia. Oncologist. 2000;5(1):63-7.
Gopal et al., PI3Kδ inhibition by idelalisib in patients with relapsed indolent lymphoma. N Engl J Med. Mar. 13, 2014;370(11):1008-18. doi: 10.1056/NEJMoa1314583. Epub Jan. 22, 2014.
Gutiérrez et al., Gene expression profiling of B lymphocytes and plasma cells from Waldenström's macroglobulinemia: comparison with expression patterns of the same cell counterparts from chronic lymphocytic leukemia, multiple myeloma and normal individuals. Leukemia. Mar. 2007;21(3):541-9. Epub Jan. 25, 2007.
Hallek et al., Signal transduction of interleukin-6 involves tyrosine phosphorylation of multiple cytosolic proteins and activation of Src-family kinases Fyn, Hck, and Lyn in multiple myeloma cell lines. Exp Hematol. Dec. 1997;25(13):1367-77.
Hanke et al., Discovery of a novel, potent, and Src family-selective tyrosine kinase inhibitor. Study of Lck- and FynT-dependent T cell activation. J Biol Chem. Jan. 12, 1996;271(2):695-701.
Herman et al., Bruton tyrosine kinase represents a promising therapeutic target for treatment of chronic lymphocytic leukemia and is effectively targeted by PCI-32765. Blood. Jun. 9, 2011;117(23):6287-96. doi: 10.1182/blood-2011-01-328484. Epub Mar. 21, 2011.
Hodge et al., IL-21 in the bone marrow microenvironment contributes to IgM secretion and proliferation of malignant cells in Waldenstrom macroglobulinemia. Blood. Nov. 1, 2012;120(18):3774-82. doi: 10.1182/blood-2012-03-419440. Epub Sep. 13, 2012.
Hong et al., The Src family kinase Hck regulates mast cell activation by suppressing an inhibitory Src family kinase Lyn. Blood. Oct. 1, 2007;110(7):2511-9. Epub May 18, 2007. Erratum in: Blood. Mar. 15, 2008;111(6):3299.
Honigberg et al., The Bruton tyrosine kinase inhibitor PCI-32765 blocks B-cell activation and is efficacious in models of autoimmune disease and B-cell malignancy. Proc Natl Acad Sci U S A. Jul. 20, 2010;107(29):13075-80. doi:10.1073/pnas.1004594107. Epub Jul. 6, 2010.
Hunter et al., Recurring activation mutations and somatic deletions revealed through whole genome sequencing in Waldenstrom's Macroglobulinemia. Hematol Oncol. Jun. 2013; 31(S1): Abstract 093.
Hunter et al., The genomic landscape of Waldenstrom macroglobulinemia is characterized by highly recurring MYD88 and WHIM-like CXCR4 mutations, and small somatic deletions associated with B-cell lymphomagenesis. Blood. Mar. 13, 2014;123(11):1637-46. doi:10.1182/blood-2013-09-525808. Epub Dec. 23, 2013.

(56) References Cited

OTHER PUBLICATIONS

Hunter et al., Use of whole genome sequencing to identify highly recurrent somatic mutations in Waldenström's macroglobulinemia. 2012 ASCO Annual Meeting. Jun. 1-5. Chicago, Illinois: Abstract 8107.
Janz, Waldenström macroglobulinemia: clinical and immunological aspects, natural history, cell of origin, and emerging mouse models. ISRN Hematol. Sep. 9, 2013;2013:815325. doi: 10.1155/2013/815325.
Jeelall et al., Oncogenic MYD88 mutation drives Toll pathway to lymphoma. Immunol Cell Biol. Aug. 2011;89(6):659-60. doi: 10.1038/icb.2011.31. Epub Apr. 26, 2011.
Jiménez et al., MYD88 L265P is a marker highly characteristic of, but not restricted to, Waldenström's macroglobulinemia. Leukemia. Aug. 2013;27(8):1722-8. doi: 10.1038/leu.2013.62. Epub Feb. 28, 2013.
Jourdan et al., Characterization of a transitional preplasmablast population in the process of human B cell to plasma cell differentiation. J Immunol. Oct. 15, 2011;187(8):3931-41. doi:10.4049/jimmunol.1101230. Epub Sep. 14, 2011.
Juilland et al., CARMA1- and MyD88-dependent activation of Jun/ATF-type Ap-1 complexes is a hallmark of ABC diffuse large B-cell lymphomas. Blood. Apr. 7, 2016;127(14):1780-9. doi:10.1182/blood-2015-07-655647. Epub Jan. 8, 2016.
Kawagoe et al., Sequential control of Toll-like receptor-dependent responses by IRAK1 and IRAK2. Nat Immunol. Jun. 2008;9(6):684-91.
Kiss et al., Comparative testing of peripheral blood and bone marrow for BCR-ABL transcripts in patients post allogeneic bone marrow transplantation and during interferon treatment for chronic myeloid leukemia. Leuk Lymphoma. Aug. 1999;34(5-6):493-500.
Kriangkum et al., Clonotypic IgM V/D/J sequence analysis in Waldenstrom macroglobulinemia suggests an unusual B-cell origin and an expansion of polyclonal B cells in peripheral blood. Blood. Oct. 1, 2004;104(7):2134-42. Epub Feb. 5, 2004.
Kyle et al., IgM monoclonal gammopathy of undetermined significance and smoldering Waldenström's macroglobulinemia. Clin Lymphoma Myeloma. Mar. 2009;9(1):17-8.
Kyle et al., Prognostic markers and criteria to initiate therapy in Waldenstrom's macroglobulinemia: consensus panel recommendations from the Second International Workshop on Waldenstrom's Macroglobulinemia. Semin Oncol. Apr. 2003;30(2):116-20.
Kyrtsonis et al., CD138 expression helps distinguishing Waldenström's macroglobulinemia (WM) from splenic marginal zone lymphoma (SMZL). Clin Lymphoma Myeloma Leuk. Feb. 2011;11(1):99-102. doi: 10.3816/CLML.2011.n.019.
Lagane et al., CXCR4 dimerization and beta-arrestin-mediated signaling account for the enhanced chemotaxis to CXCL12 in WHIM syndrome. Blood. Jul. 1, 2008;112(1):34-44. doi: 10.1182/blood-2007-07-102103. Epub Apr. 24, 2008.
Lam et al., Cooperative signaling through the signal transducer and activator of transcription 3 and nuclear factor-{kappa}B pathways in subtypes of diffuse large B-cell lymphoma. Blood. Apr. 1, 2008;111(7):3701-13. Epub Dec. 26, 2007.
Landgren et al., MYD88 L265P somatic mutation in IgM MGUS. N Engl J Med. Dec. 6, 2012;367(23):2255-6; author reply 2256-7. doi: 10.1056/NEJMc1211959#SA1.
Lee et al., The mutation spectrum revealed by paired genome sequences from a lung cancer patient. Nature. May 27, 2010;465(7297):473-7.
Leleu et al., Targeting NF-kappaB in Waldenstrom macroglobulinemia. Blood. May 15, 2008;111(10):5068-77.
Leleu et al., The Akt pathway regulates survival and homing in Waldenstrom macroglobulinemia. Blood. Dec. 15, 2007;110(13):4417-26. Epub Aug. 30, 2007.
Lin et al., Helical assembly in the MyD88-IRAK4-IRAK2 complex in TLR/IL-1R signaling. Nature. Jun. 17, 2010;465(7300):885-90.
Lin et al., Lymphoid neoplasms associated with IgM paraprotein: a study of 382 patients. Am J Clin Pathol. Feb. 2005;123(2):200-5.
Loiarro et al., Identification of critical residues of the MyD88 death domain involved in the recruitment of downstream kinases. J Biol Chem. Oct. 9, 2009;284(41):28093-103.
Loiarro et al., Peptide-mediated interference of TIR domain dimerization in MyD88 inhibits interleukin-1-dependent activation of NF-{kappa}B. J Biol Chem. Apr. 22, 2005;280(16):15809-14. Epub Mar. 8, 2005.
Loiarro et al., Pivotal Advance: Inhibition of MyD88 dimerization and recruitment of IRAK1 and IRAK4 by a novel peptidomimetic compound. J Leukoc Biol. Oct. 2007;82(4):801-10. Epub Jun. 4, 2007.
Martínez et al., Whole-exome sequencing in splenic marginal zone lymphoma reveals mutations in genes involved in marginal zone differentiation. Leukemia. Jun. 2014;28(6):1334-40. doi: 10.1038/leu.2013.365. Epub Dec. 3, 2013.
McDermott et al., A phase 1 clinical trial of long-term, low-dose treatment of WHIM syndrome with the CXCR4 antagonist plerixafor. Blood. Apr. 10, 2014;123(15):2308-16. doi:10.1182/blood-2013-09-527226. Epub Feb. 12, 2014.
McDermott et al., AMD3100 is a potent antagonist at CXCR4 (R334X), a hyperfunctional mutant chemokine receptor and cause of WHIM syndrome. J Cell Mol Med. Oct. 2011;15(10):2071-81. doi: 10.1111/j.1582-4934.2010.01210.x.
McDermott et al., The CXCR4 antagonist plerixafor corrects panleukopenia in patients with WHIM syndrome. Blood. Nov. 3, 2011;118(18):4957-62. doi: 10.1182/blood-2011-07-368084. Epub Sep. 2, 2011.
McMaster et al., Long-term evaluation of three multiple-case Waldenstrom macroglobulinemia families. Clin Cancer Res. Sep. 1, 2007;13(17):5063-9.
Messeguer et al., PROMO: detection of known transcription regulatory elements using species-tailored searches. Bioinformatics. Feb. 2002;18(2):333-4.
Mueller et al., Hierarchical organization of multi-site phosphorylation at the CXCR4 C terminus. PLoS One. May 29, 2013;8(5):e64975. doi: 10.1371/journal.pone.0064975. Print 2013.
Musumeci et al., Hck inhibitors as potential therapeutic agents in cancer and HIV infection. Curr Med Chem. 2015;22(13):1540-64.
Ngo et al., Oncogenically active MYD88 mutations in human lymphoma. Nature. Feb. 3, 2011;470(7332):115-9. doi: 10.1038/nature09671.
Ngo et al., SDF-1/CXCR4 and VLA-4 interaction regulates homing in Waldenstrom macroglobulinemia. Blood. Jul. 1, 2008;112(1):150-8. doi: 10.1182/blood-2007-12-129395. Epub Apr. 30, 2008.
O'Boyle et al., Open Babel: An open chemical toolbox. J Cheminform. Oct. 7, 2011;3:33. doi:10.1186/1758-2946-3-33.
Okuzumi et al., Inhibitor hijacking of Akt activation. Nat Chem Biol. Jul. 2009;5(7):484-93. doi:10.1038/nchembio.183. Epub May 24, 2009.
Ondrejka et al., MYD88 L265P somatic mutation: its usefulness in the differential diagnosis of bone marrow involvement by B-cell lymphoproliferative disorders. Am J Clin Pathol. Sep. 2013;140(3):387-94. doi: 10.1309/AJCP10ZCLFZGYZIP.
Owen et al., Clinicopathological definition of Waldenstrom's macroglobulinemia: consensus panel recommendations from the Second International Workshop on Waldenstrom's Macroglobulinemia. Semin Oncol. Apr. 2003;30(2):110-5.
Passamonti, How I treat polycythemia vera. Blood. Jul. 12, 2012;120(2):275-84. doi: 10.1182/blood-2012-02-366054. Epub May 18, 2012.
Patricelli et al., In situ kinase profiling reveals functionally relevant properties of native kinases. Chem Biol. Jun. 24, 2011;18(6):699-710. doi:10.1016/j.chembiol.2011.04.011.
Pecquet et al., The Src tyrosine kinase Hck is required for Tel-Abl- but not for Tel-Jak2-induced cell transformation. Oncogene. Mar. 8, 2007;26(11):1577-85. Epub Sep. 4, 2006.
Pene-Dumitrescu et al., An inhibitor-resistant mutant of Hck protects CML cells against the antiproliferative and apoptotic effects of the broad-spectrum Src family kinase inhibitor A-419259. Oncogene. Nov. 27, 2008;27(56):7055-69. doi:10.1038/onc.2008.330. Epub Sep. 15, 2008.

(56) References Cited

OTHER PUBLICATIONS

Poh et al., Hematopoietic cell kinase (HCK) as a therapeutic target in immune and cancer cells. Oncotarget. Jun. 30, 2015;6(18):15752-71.

Poulain et al., MYD88 L265P mutation in Waldenstrom macroglobulinemia. Blood. May 30, 2013;121(22):4504-11. doi: 10.1182/blood-2012-06-436329. Epub Mar. 26, 2013.

Powers et al., Discovery and initial SAR of inhibitors of interleukin-1 receptor-associated kinase-4. Bioorg Med Chem Lett. Jun. 1, 2006;16(11):2842-5. Epub Mar. 24, 2006.

Puente et al., Whole-genome sequencing identifies recurrent mutations in chronic lymphocytic leukaemia. Nature. Jun. 5, 2011;475(7354):101-5. doi:10.1038/nature10113.

Roach et al., Analysis of genetic inheritance in a family quartet by whole-genome sequencing. Science. Apr. 30, 2010;328(5978):636-9.

Roccaro et al., A Novel Activating Mutation of CXCR4 Plays a Crucial Role in Waldenstrom Macroglobulinemia Biology. Blood. 2013;122: Abstract 272.

Roccaro et al., C1013G/CXCR4 acts as a driver mutation of tumor progression and modulator of drug resistance in lymphoplasmacytic lymphoma. Blood. Jun. 26, 2014;123(26):4120-31. doi:10.1182/blood-2014-03-564583. Epub Apr. 7, 2014.

Sahota et al., CD27 in defining memory B-cell origins in Waldenström's macroglobulinemia. Clin Lymphoma Myeloma. Mar. 2009;9(1):33-5. doi: 10.3816/CLM.2009.n.007.

Saito et al., A pyrrolo-pyrimidine derivative targets human primary AML stem cells in vivo. Sci Transl Med. Apr. 17, 2013;5(181):181ra52. doi: 10.1126/scitranslmed.3004387.

Sanner et al., Reduced surface: an efficient way to compute molecular surfaces. Biopolymers. Mar. 1996;38(3):305-20.

Schaeffer et al., Signaling through a novel domain of gp130 mediates cell proliferation and activation of Hck and Erk kinases. Mol Cell Biol. Dec. 2001;21(23):8068-81.

Smith et al., In Waldenstrom's macroglobulinemia the quantity of detectable circulating monoclonal B lymphocytes correlates with clinical course. Blood. May 1983;61(5):911-4.

Song et al., The kinase activities of interleukin-1 receptor associated kinase (IRAK)-1 and 4 are redundant in the control of inflammatory cytokine expression in human cells. Mol Immunol. Apr. 2009;46(7):1458-66.

Suh et al., Inhibition of granulocyte-macrophage colony-stimulating factor signaling and microglial proliferation by anti-CD45RO: role of Hck tyrosine kinase and phosphatidylinositol 3-kinase/Akt. J Immunol. Mar. 1, 2005;174(5):2712-9.

Taguchi et al., Characteristic expression of Hck in human B-cell precursors. Exp Hematol. Jan. 2000;28(1):55-64. Erratum in: Exp Hematol. Mar. 2000;28(3):347.

Tai et al., Bruton tyrosine kinase inhibition is a novel therapeutic strategy targeting tumor in the bone marrow microenvironment in multiple myeloma. Blood. Aug. 30, 2012;120(9):1877-87. doi: 10.1182/blood-2011-12-396853. Epub Jun. 11, 2012.

Tiacci et al., Simple genetic diagnosis of hairy cell leukemia by sensitive detection of the BRAF-V600E mutation. Blood. Jan. 5, 2012;119(1):192-5. doi:10.1182/blood-2011-08-371179. Epub Oct. 25, 2011. Erratum in: Blood. Aug. 29, 2013;122(9):1685.

Treon et al., A new era for Waldenstrom macroglobulinemia: MYD88 L265P. Blood. May 30, 2013;121(22):4434-6. doi: 10.1182/blood-2013-04-494849.

Treon et al., A Prospective Multicenter Study of the Bruton's Tyrosine Kinase Inhibitor Ibrutinib in Patients With Relapsed or Refractory Waldenstrom's Macroglobulinemia. Blood. 2013;122:Abstract 251.

Treon et al., A prospective, multicenter, phase II study of the Bruton's Tyrosine Kinase Inhibitor Ibrutinib in patients with relapsed and refractory Waldenstrom's Macroglobulinemia. Hematol Oncol. Jun. 2013;31(S1): Abstract 067.

Treon et al., Characterization of familial Waldenstrom's macroglobulinemia. Ann Oncol. Mar. 2006;17(3):488-94. Epub Dec. 15, 2005.

Treon et al., Ibrutinib in previously treated Waldenström's macroglobulinemia. N Engl J Med. Apr. 9, 2015;372(15):1430-40. doi:10.1056/NEJMoa1501548.

Treon et al., Multicenter clinical trial of bortezomib in relapsed/refractory Waldenstrom's macroglobulinemia: results of WMCTG Trial 03-248. Clin Cancer Res. Jun. 1, 2007;13(11):3320-5.

Treon et al., MYD88 L265P somatic mutation in Waldenström's macroglobulinemia. N Engl J Med. Aug. 30, 2012;367(9):826-33. doi:10.1056/NEJMoa1200710.

Treon et al., MYD88 Mutations and Response to Ibrutinib in Waldenström's Macroglobulinemia. N Engl J Med. Aug. 6, 2015;373(6):584-6. doi:10.1056/NEJMc1506192.

Treon et al., Prospective phase II clinical trial of carfilzomib, rituximab, and dexamethasone (CaRD) in Waldenstrom's macroglobulinemia. 12th International Conference on Malignant Lymphoma. Palazzo dei Congressi, Lugano, Switzerland, Jun. 19-22, 2013, abstract 150, 2013.

Treon et al., Prospective, Multicenter Study of the MTOR Inhibitor Everolimus (RAD001) As Primary Therapy in Waldenstrom's Macroglobulinemia. Blood. 2011;118:Abstract 2951.

Treon et al., Somatic mutations in MYD88 and CXCR4 are determinants of clinical presentation and overall survival in Waldenstrom macroglobulinemia. Blood. May 1, 2014;123(18):2791-6. doi:10.1182/blood-2014-01-550905. Epub Feb. 19, 2014.

Treon et al., Whole Genome sequencing reveals a widely expressed mutation (MYD88 L265P) in Waldenstrom's Macroglobulinemia. Oral and Poster Abstracts. Dec. 2011. 1 Page.

Treon, How I treat Waldenström macroglobulinemia. Blood. Sep. 17, 2009;114(12):2375-85.

Trøen et al., CD79B and MYD88 Mutations in Splenic Marginal Zone Lymphoma. ISRN Oncol. 2013;2013:252318. doi: 10.1155/2013/252318. Epub Jan. 10, 2013.

Trott et al., AutoDock Vina: improving the speed and accuracy of docking with a new scoring function, efficient optimization, and multithreading. J Comput Chem. Jan. 30, 2010;31(2):455-61. doi: 10.1002/jcc.21334.

Varettoni et al., Prevalence and clinical significance of the MYD88 (L265P) somatic mutation in Waldenstrom's macroglobulinemia and related lymphoid neoplasms. Blood. Mar. 28, 2013;121(13):2522-8. doi: 10.1182/blood-2012-09-457101. Epub Jan. 25, 2013.

Wang et al., CD19: a biomarker for B cell development, lymphoma diagnosis and therapy. Experimental Hematol Oncol. 2012;1(36):1-7.

Wang et al., IRAK-4 inhibitors for inflammation. Curr Top Med Chem. 2009;9(8):724-37.

Watters et al., Structure, function and regulation of the Toll/IL-1 receptor adaptor proteins. Immunol Cell Biol. Aug.-Sep. 2007;85(6):411-9. Epub Jul. 31, 2007.

Willenbacher et al., Improved accuracy of discrimination between IgM multiple myeloma and Waldenström macroglobulinaemia by testing for MYD88 L265P mutations. Br J Haematol. Jun. 2013;161(6):902-4. doi:10.1111/bjh.12313. Epub Apr. 5, 2013.

Wilson et al., Targeting B cell receptor signaling with ibrutinib in diffuse large B cell lymphoma. Nat Med. Aug. 2015;21(8):922-6. doi: 10.1038/nm.3884. Epub Jul. 20, 2015.

Woyach et al., Resistance mechanisms for the Bruton's tyrosine kinase inhibitor ibrutinib. N Engl J Med. Jun. 12, 2014;370(24):2286-94. doi: 10.1056/NEJMoa1400029. Epub May 28, 2014.

Xu et al., Detection of MYD88 L265P In Peripheral Blood of Patients With Waldenström's Macroglobulinemia and IgM Monoclonal Gammopathy of Undetermined Significance. Blood. 2013;122(21): Abstract 3024.

Xu et al., Detection of MYD88 L265P in peripheral blood of patients with Waldenström's Macroglobulinemia and IgM monoclonal gammopathy of undetermined significance. Leukemia. Aug. 2014;28(8):1698-704. doi: 10.1038/leu.2014.65. Epub Feb. 10, 2014.

Xu et al., MYD88 L265P in Waldenström macroglobulinemia, immunoglobulin M monoclonal gammopathy, and other B-cell lymphoproliferative disorders using conventional and quantitative allele-specific polymerase chain reaction. Blood. Mar. 14, 2013;121(11):2051-8. doi: 10.1182/blood-2012-09-454355. Epub Jan. 15, 2013. Erratum in: Blood. Jun. 27, 2013;121(26):5259.

(56) References Cited

OTHER PUBLICATIONS

Yang et al., A mutation in MYD88 (L265P) supports the survival of lymphoplasmacytic cells by activation of Bruton tyrosine kinase in Waldenström macroglobulinemia. Blood. Aug. 15, 2013;122(7):1222-32. doi:10.1182/blood-2012-12-475111. Epub Jul. 8, 2013.

Yang et al., Tyrosine kinase inhibition in diffuse large B-cell lymphoma: molecular basis for antitumor activity and drug resistance of dasatinib. Leukemia. Sep. 2008;22(9):1755-66. doi:10.1038/leu.2008.163. Epub Jul. 3, 2008.

Ye et al., t(1;14) and t(11;18) in the differential diagnosis of Waldenström's macroglobulinemia. Mod Pathol. Sep. 2004;17(9):1150-4.

Extended European Search Report for EP14844516.6 dated Mar. 28, 2017.

International Search Report and Written Opinion for PCT/US2017/030116 dated Aug. 21, 2017.

Dave et al., Molecular diagnosis of Burkitt's lymphoma. New Engl J Med. Jun. 8, 2006;354(23):2431-42.

Harris et al., A revised European-American classification of lymphoid neoplasms: a proposal from the International Lymphoma Study Group. Blood. Sep. 1, 1994;84(5):1361-92.

Okada et al., Autopsy case of lymphoplasmacytic lymphoma with a large submucosal tumor in the stomach. Pathol Int. Oct. 2001;51(10):802-6.

Tai et al., Targeting Brouton's Tyrosine Kinase with PCI-32765 Blocks Growth and Survival of Multiple Myeloma and Waldenström Macroglobulinemia Via Potent Inhibition of Osteoclastogenesis, Cytokines/Chemokine Secretion, and Myeloma Stem-Like Cells in the Bone Marrow Microenvironment. Blood. Nov. 18, 2011;118(21):404. Abstract.

Xu et al., Detection of the MYD88 L265P mutation in Waldenström's macroglobulinemia using a highly sensitive allele-specific PCR assay. J Clinical Oncology. May 2012;30(15):8042. Abstract.

Yang et al., HCK is a Highly Relevant Target of Ibrutinib in MYD88 Mutated Waldenstrom's Macroglobulinemia and Diffuse Large B-Cell Lymphoma. Blood. 2015;126:705.

Yang et al., HCK is a survival determinant transactivated by mutated MYD88, and a direct target of ibrutinib. Blood. Jun. 23, 2016;127(25):3237-52. doi: 10.1182/blood-2016-01-695098. Epub May 3, 2016.

Baxter et al., Acquired mutation of the tyrosine kinase JAK2 in human myeloproliferative disorders. Lancet. Mar. 19-25, 2005;365(9464):1054-61.

International Preliminary Report on Patentability for PCT/US2017/030116 dated Nov. 8, 2018.

PCT/US2017/030116, Nov. 8, 2018, International Preliminary Report on Patentability.

\* cited by examiner

SEQUENCE LISTING

```
<160> NUMBER OF SEQ ID NOS: 17

<210> SEQ ID NO 1
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 1
gctgccttac tacattggga tcagc                                           25

<210> SEQ ID NO 2
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 2
ttggccacag gtcctgccta gaca                                            24

<210> SEQ ID NO 3
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 3
ccttgtactt gatggggaac g                                               21

<210> SEQ ID NO 4
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 4
agactcagac tcagtggaaa cagttc                                          26

<210> SEQ ID NO 5
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 5
```
agactcagac tcagtggaaa caggtt                                              26

<210> SEQ ID NO 6
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 6
agactcagac tcagtggaaa cagttg                                              26

<210> SEQ ID NO 7
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 7
ttccactgtt gtctgaaccc catc                                                24

<210> SEQ ID NO 8
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 8
actacattgg gatcagcatc gactc                                               25

<210> SEQ ID NO 9
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 9
tgaagactca gactcagtgg aaacag                                              26

<210> SEQ ID NO 10
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 10
atggggagga gagttgtagg attctac                                             27

<210> SEQ ID NO 11
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 11
ttggccacag gtcctgccta gaca                                                24

<210> SEQ ID NO 12
<211> LENGTH: 25
<212> TYPE: DNA

-continued

<213> ORGANISM: Artificial Sequence
<220> FEATURE:
<223> OTHER INFORMATION: Synthetic Oligonucleotide

<400> SEQUENCE: 12
gctgccttac tacattggga tcagc                                              25

<210> SEQ ID NO 13
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 13

Lys Phe Lys Thr Ser Ala Gln His Ala Leu Thr Ser Val Ser Arg Gly
1               5                   10                  15

Ser Ser Leu Lys Ile Leu Ser Lys Gly Lys Arg Gly Gly His Ser Ser
            20                  25                  30

Val Ser Thr Glu Ser Glu Ser Ser Phe His Ser Ser
        35                  40                  45

<210> SEQ ID NO 14
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 14

Lys Phe Lys Thr Ser Ala Gln His Ala Leu Thr Ser Val Ser Arg Gly
1               5                   10                  15

Ser Ser Leu Lys Ile Leu Ser Lys Gly Lys Arg Gly Gly His
            20                  25                  30

<210> SEQ ID NO 15
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 15

Lys Phe Lys Asn Leu Cys Pro Ala Arg Thr His Leu Cys Glu Gln Arg
1               5                   10                  15

Val Gln Pro Gln Asp Pro Leu Pro Arg Lys Ala Arg Val Thr Phe Ile
            20                  25                  30

Cys Phe His
        35

<210> SEQ ID NO 16
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 16

Lys Phe Lys Thr Ser Ala Gln His Ala Leu Thr Ser Val Ser Arg Gly
1               5                   10                  15

Ser Ser Leu Lys Ile Leu Ser Lys Gly Lys Arg Gly Gly His Ser Ser
            20                  25                  30

Val Ser Thr Glu Cys Lys Phe Ser Leu Gln Leu Thr Gln Met

```
<210> SEQ ID NO 17
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 17
gaagactcag                                                          10
```

METHODS FOR EVALUATING AND TREATING WALDENSTROM'S MACROGLOBULINEMIA

RELATED APPLICATIONS

This application is a national stage filing under 35 U.S.C. § 371 of International Application No. PCT/US2014/055386, filed Sep. 12, 2014, and entitled "METHODS FOR EVALUATING AND TREATING WALDENSTROM'S MACROGLOBULINEMIA," which claims the benefit under 35 U.S.C. § 119(e) of U.S. provisional application Ser. No. 61/877,009, filed Sep. 12, 2013, and of U.S. provisional application Ser. No. 61/889,150, filed Oct. 10, 2013, the contents of each of which are incorporated by reference herein in their entirety.

BACKGROUND OF THE INVENTION

Lymphoma is the most common blood cancer. Lymphoma occurs when lymphocytes multiply uncontrollably. The body has two main types of lymphocytes that can develop into lymphomas: B-lymphocytes (B-cells) and T-lymphocytes (T-cells).

Waldenström's macroglobulinemia (also known as lymphoplasmacytic lymphoma or immunocytoma) is a rare, indolent (slow-growing) B-cell lymphoma that occurs in less than two percent of patients with non-Hodgkin lymphoma. There are about 1,500 new cases of Waldenström's each year. The disease is primarily found in the bone marrow, although lymph nodes and the spleen may be involved.

The disease, named after the Swedish oncologist Jan G. Waldenström, was first identified in 1944. The proliferation of B-cells interferes with the production of red blood cells, resulting in anemia. A characteristic of the disease is that the B-cells produce excess amounts of the immunoglobulin IgM. These high levels of IgM can cause a thickening of the blood, resulting in symptoms such as nosebleeds, headaches, dizziness, and blurring or loss of vision. Other symptoms may include tiredness, night sweats, headaches, pain or numbness in the extremities, and increased size of the liver, spleen, and lymph nodes.

Current treatment of WM includes the monoclonal antibody rituximab, sometimes in combination with chemotherapeutic drugs such as chlorambucil, cyclophosphamide, or vincristine or with thalidomide. Corticosteroids, such as Prednisone, may also be used in combination. Plasmapheresis can be used to treat the hyperviscosity syndrome by removing the paraprotein from the blood, although it does not address the underlying disease. Recently, autologous bone marrow transplantation has been added to the available treatment options.

Bruton's tyrosine kinase (BTK), a member of the src-related BTK/Tec family of cytoplasmic tyrosine kinases, is required for B cell receptor signaling, plays a key role in B-cell maturation, and exhibits increased activation in a number of B-cell malignancies. BTK inhibitors are under investigation for the treatment of certain lymphomas. Prior to the present invention, BTK inhibitors had not been tested for treatment of WM.

CXCR4 is a chemokine receptor specific for stromal-derived-factor-1 (SDF-1 also called CXCL12). CXCR4 is a G-protein-coupled receptor involved in a number of physiological processes in the hematopoietic and immune systems. The SDF-1/CXCR4 interaction is associated with several diseases, such as HIV, WHIM syndrome, rheumatoid arthritis, pulmonary fibrosis, lupus and cancer. CXCR4's ligand SDF-1 is known to be important in hematopoietic stem cell homing to the bone marrow and in hematopoietic stem cell quiescence.

There are known CXCR4 mutations associated with Warts, *Hypogammaglobulinemia, Infection, and Myelokathexis* (WHIM) syndrome (Hunter et al, ASCO 2012), a rare autosomal dominant genetic disorder that is caused by frame shift or nonsense mutations in the carboxyl-terminal cytoplasmic tail of CXCR4. In WHIM syndrome, the germ-line mutation causes a loss of the c-terminal tail of CXCR4, which is believed to impair receptor internalization, thereby prolonging signaling. Prior to the invention, there had been no known association between CXCR4 mutations and WM treatment.

SUMMARY OF THE INVENTION

The invention involves a number of unexpected discoveries. The inventors discovered, surprisingly, that BTK inhibitors can be used to treat successfully WM. The inventors further discovered that WHIM like mutations to CXCR4 were present as somatic mutations in WM and were predictive of whether various WM therapies, including BTK inhibition treatment would be successful. They further discovered that CXCR4 inhibition treatment, AKT inhibition treatment and/or ERK inhibition treatment, when combined with BTK inhibition treatment, could restore the ability to treat WM successfully even in the presence of CXCR4 mutation.

The inventors discovered that the BTK inhibitor ibrutinib induces WM cell death, and is highly active in WM. Through whole genome sequencing, the inventors identified somatic mutations in CXCR4 that affected ⅓ of WM patients.

According to one aspect of the invention, a method for treating a subject who has Waldenstrom's macroglobulinemia is provided. The method involves administering to a human subject in need of such treatment a BTK inhibitor in an amount effective to treat the Waldenstrom's macroglobulinemia. The BTK inhibitor may be any BTK inhibitor, including any of the BTK inhibitors described herein. The BTK inhibitor may be ibrutinib. In any of the embodiments, the subject may have wild-type CXCR4 or may have a CXCR4 WHIM like mutation.

According to another aspect of the invention, a method for evaluating a subject having Waldenstrom's macroglobulinemia is provided. The method involves obtaining diseased B cells from the subject, and performing an assay on the diseased B cells to determine whether the diseased B cells contain a mutation in the carboxyl-terminal cytoplasmic tail of the gene encoding CXCR4, wherein the presence or absence of the mutation in the diseased B cell indicates the subject's likely responsiveness to treatment with various therapies. In embodiments, the presence of the mutation in the diseased B cell indicates that the subject is unlikely to be responsive to BTK inhibitor treatment. The subject having the mutation in the diseased B cell may be identified as unlikely to be responsive to treatment with a BTK inhibitor. In any of the embodiments, the presence or absence of the mutation may be determined by isolating nucleic acids obtained from the B cells, amplifying the nucleic acids and determining the presence or absence of the mutation in the amplified nucleic acids. In any of the embodiments, the presence or absence of the mutation is determined by allele-specific polymerase chain reaction (AS-PCR). In any of the embodiments, the diseased B cells may be isolated from other blood cells of the subject prior to determining the presence or absence of the mutation. In any of the embodiments, the mutation may be a frame shift or nonsense mutation in the gene encoding the carboxyl-terminal cytoplasmic tail of CXCR4. The method may further involve obtaining non-B cells or non-diseased cells from the subject, and performing an assay on the cells to determine whether the non-B cells or non-diseased cells contain a mutation in the carboxyl-terminal cytoplasmic tail of the gene encoding CXCR4.

According to another aspect of the invention, a method for evaluating a subject is provided. The method involves performing a test on the subject to determine if the subject has Waldenstrom's macroglobulinemia, obtaining diseased B cells from a subject having Waldenstrom's macroglobulinemia, and determining whether the diseased B cells contain a mutation in the carboxyl-terminal cytoplasmic tail of the gene encoding CXCR4, wherein if the subject has Waldenstrom's macroglobulinemia, then the presence or absence of the mutation in the diseased B cells indicates the subject's likely responsiveness to treatment with various therapies.

In embodiments, the presence of the mutation in the diseased B cells indicates that the subject is unlikely to be responsive to BTK inhibitor treatment. The subject having the mutation in the diseased B cells may be identified as having WM and as being unlikely to be responsive to treatment with a BTK inhibitor. In any of the embodiments, the presence or absence of the mutation may be determined by isolating nucleic acids obtained from the B cells, amplifying the nucleic acids and determining the presence or absence of the mutation in the amplified nucleic acids. In any of the embodiments, the presence or absence of the mutation is determined by allele-specific polymerase chain reaction (AS-PCR). In any of the embodiments, the diseased B cells may be isolated from other blood cells of the subject prior to determining the presence or absence of the mutation. In any of the embodiments, the mutation may be a frame shift or nonsense mutation in the gene encoding the carboxyl-terminal cytoplasmic tail of CXCR4. The method may further involve obtaining non-B cells or non-diseased cells from the subject, and performing an assay on the cells to determine whether the non-B cells or non-diseased cells contain a mutation in the carboxyl-terminal cytoplasmic tail of the gene encoding CXCR4.

According to another aspect of the invention, a method for evaluating a subject is provided. The method involves obtaining B cells from the subject, performing an assay on the diseased B cells to determine whether the diseased B cells contain a mutation in the carboxyl-terminal cytoplasmic tail of the gene encoding CXCR4, obtaining non-B cells or non-diseased cells from the subject, and performing an assay on the cells to determine whether the non-B cells or non-diseased cells contain a mutation in the carboxyl-terminal cytoplasmic tail of the gene encoding CXCR4. The subject having the mutation in the diseased B cell and no mutation in the non-diseased cell may be identified as having WM. The subject having the mutation in the diseased B cell and no mutation in the non-diseased cell may be identified as unlikely to be responsive to treatment with a BTK inhibitor. In any of the embodiments, the presence or absence of the mutation may be determined by isolating nucleic acids obtained from the B cells, amplifying the nucleic acids and determining the presence or absence of the mutation in the amplified nucleic acids. In any of the embodiments, the presence or absence of the mutation is determined by allele-specific polymerase chain reaction (AS-PCR). In any of the embodiments, the diseased B cells may be isolated from other blood cells of the subject prior to determining the presence or absence of the mutation. In any of the embodiments, the mutation may be a frame shift or nonsense mutation in the gene encoding the carboxyl-terminal cytoplasmic tail of CXCR4.

17.

In any of the foregoing evaluation methods, the method may further comprise first performing a test on the subject to determine if the subject has or is suspected of having Waldenstrom's macroglobulinemia. In some embodiments, the test comprises a blood test, a bone marrow biopsy, computed tomography scan, or flow cytometry.

According to another aspect of the invention, a method for treating a subject having Waldenstrom's macroglobulinemia is provided. The method involves obtaining diseased B cells from the subject, and performing an assay on the diseased B cells to determine whether the diseased B cells contain a mutation in the carboxyl-terminal cytoplasmic tail of the gene encoding CXCR4, and if the subject has a mutation in the carboxyl-terminal cytoplasmic tail of the gene encoding CXCR4, then administering to the subject an effective amount of (i) an anti-cancer agent for Waldenstrom's macroglobulinemia that is not a BTK inhibitor or (ii) a BTK inhibitor in combination with a CXCR4 inhibitor, an AKT inhibitor and/or an ERK inhibitor; or if the subject does not have a mutation in the carboxyl-terminal cytoplasmic tail of the gene encoding CXCR4, then administering to the subject an effective amount of an anti-cancer agent for Waldenstrom's macroglobulinemia, optionally a BTK inhibitor.

According to another aspect of the invention, a method for treating a subject having Waldenstrom's macroglobulinemia is provided. The method involves directing a test on diseased B cells obtained from the subject to determine whether the diseased B cells contain a mutation in the carboxyl-terminal cytoplasmic tail of the gene encoding CXCR4, and if the subject has a mutation in the carboxyl-terminal cytoplasmic tail of the gene encoding CXCR4, then administering to the subject an effective amount of (i) an anti-cancer agent for Waldenstrom's macroglobulinemia that is not a BTK inhibitor or (ii) a BTK inhibitor in combination with a CXCR4 inhibitor, an AKT inhibitor and/or an ERK inhibitor; or if the subject does not have a mutation in the carboxyl-terminal cytoplasmic tail of the gene encoding CXCR4, then administering to the subject an effective amount of an anti-cancer agent for Waldenstrom's macroglobulinemia, optionally a BTK inhibitor.

According to another aspect of the invention, a method for treating a subject having Waldenstrom's macroglobulinemia is provided. The method involves (a) selecting the subject on the basis that the subject is known to have contain a mutation in the carboxyl-terminal cytoplasmic tail of the gene encoding CXCR4; and (b) administering an effective amount of (i) an anti-cancer agent that is not a BTK inhibitor or (ii) a BTK inhibitor in combination with a CXCR4 inhibitor, an AKT inhibitor and/or an ERK inhibitor, to the subject because the subject has a mutation in the carboxyl-terminal cytoplasmic tail of the gene encoding CXCR4.

In any of the treatment embodiments, the anti-cancer agent for treating WM (which is not a BTK inhibitor) can be an alkylator, an anthracycline, a nucleoside analogs, an anti-CD20 monoclonal antibody, thalidomide, an immunomodulatory derivative of thalidomide, interferon, a proteasome inhibitor, a protein kinase C inhibitor, a monoclonal antibody to CD52 and a microtubule inhibitor. In some embodiments, the anti-cancer agent is on or more of chlorambucil, Carmustine (bis-chloroethylnitrosourea), cyclophosphamide, vincristine, melphalan, prednisone, cladribine (2-chlorodeoxyadenosine), adriamycin, rituximab, thalidomide, dexamethasone, alpha-interferon (α-IFN), carfilzomib, oprozomib, ixazomib (proteasome inhibitors) UCN-01 (a protein kinase C inhibitor), Campath-1H (monoclonal antibody to CD52), and dolastatin (a microtubule inhibitor).

In any of the treatment embodiments, the assays can be as described herein.

In any of the treatment embodiments, the CXCR4 inhibitor can be as described herein.

In any of the foregoing embodiments, the BTK inhibitor can be as described herein. In any embodiment, the BTK inhibitor can be ibrutinib.

In any of the foregoing embodiments, the AKT inhibitor can be as described herein. In any of the foregoing embodiments, the ERK inhibitor can be as described herein.

According to one aspect of the invention, a method to distinguish Waldenstrom's macroglobulinemia from other B cell neoplasms is provided. The method comprises performing an assay on a biological sample obtained from a subject in need thereof to determine whether the subject has a mutation at position 38182641 in chromosome 3p22.2; performing an assay on diseased B cells obtained from the subject to determine whether the diseased B cells contain a mutation in the carboxyl-terminal cytoplasmic tail of the gene encoding CXCR4, wherein the subject has Waldenstrom's macroglobulinemia if the subject has a mutation at position 38182641 in chromosome 3p22.2 and a mutation in the carboxyl-terminal cytoplasmic tail of the gene encoding CXCR4.

In some embodiments, the biological sample is a sample of bone marrow, lymph node, spleen or blood. In some embodiments, the mutation at position 38182641 results in a single nucleotide change from T to C in the myeloid differentiation primary response 88 (MYD88) gene. In some embodiments, the mutation at position 38182641 results in an amino acid change from leucine to proline at position 265 in the myeloid differentiation primary response 88 protein. In some embodiments, the assay to determine whether the subject has a mutation at position 38182641 in chromosome 3p22.2 comprises allele specific polymerase chain reaction performed using an allele specific primer, wherein the allele specific primer hybridizes at or near its 3' end to the mutation at position 38182641 in chromosome 3p22.2. In some embodiments, the mutation is a frame shift or nonsense mutation in the gene encoding the carboxyl-terminal cytoplasmic tail of CXCR4. In some embodiments, the assay to determine whether the diseased B cells contain a mutation in the carboxyl-terminal cytoplasmic tail of the gene encoding CXCR4 comprises allele specific polymerase chain reaction.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1. Sensitivity and specificity plots for real-time AS-PCR assays.

FIG. 4. CXCR4 cell surface expression following SDF-1a stimulation of $CXCR4^{WT}$ and $CXCR4^{S338X}$ expressing BCWM.1 and MWCL-1 cells. (FIG. 4B) Changes in cell surface CXCR4 expression following stimulation of $CXCR4^{WT}$ and $CXCR4^{S338X}$ engineered BCWM.1 and MWCL-1 cells for 30 minutes at 37° C. with SDF-1a (10 nM, 100 nM). Surface CXCR4 expression was assessed by flow cytometry and expression relative to baseline levels are shown. Data represent the median of at least 3 independent experiments; *p<0.001 for $CXCR4^{S338X}$ versus $CXCR4^{WT}$ expressing BCWM.1 and MWCL-1 cells at both 10 nM and 100 nM dose of SDF-1a.

FIG. 5. Impact of SDF-1a on AKT, ERK or BTK activation in plenti-GFP vector only, $CXCR4^{WT}$ and $CXCR4^{S338X}$ expressing BCWM.1 and MWCL-1 cells.

FIG. 8. Inhibitors of AKT or ERK overcome SDF-1a mediated resistance to ibrutinib triggered PARP and caspase 3 cleavage in CXCR4$^{S338X}$ expressing BCWM.1 cells. CXCR4$^{S338X}$ expressing WM cells were treated with ibrutinib (0.5 uM) alone or in the presence of SDF-1a (20 nM) and/or the AKT inhibitors MK-2206 (0.5 uM) and AZD-5363 (0.5 uM); or the MEK inhibitors AS-703026 (0.25 uM), AZD-6244 (0.5 uM) and U0126 (5.0 uM).

FIG. 11. CXCR4 cell surface expression following SDF-1a stimulation of CXCR4$^{WT}$, CXCR4$^{FS}$ and CXCR4$^{S338X}$ expressing WM cells.

DETAILED DESCRIPTION OF THE INVENTION

Figure 1A:
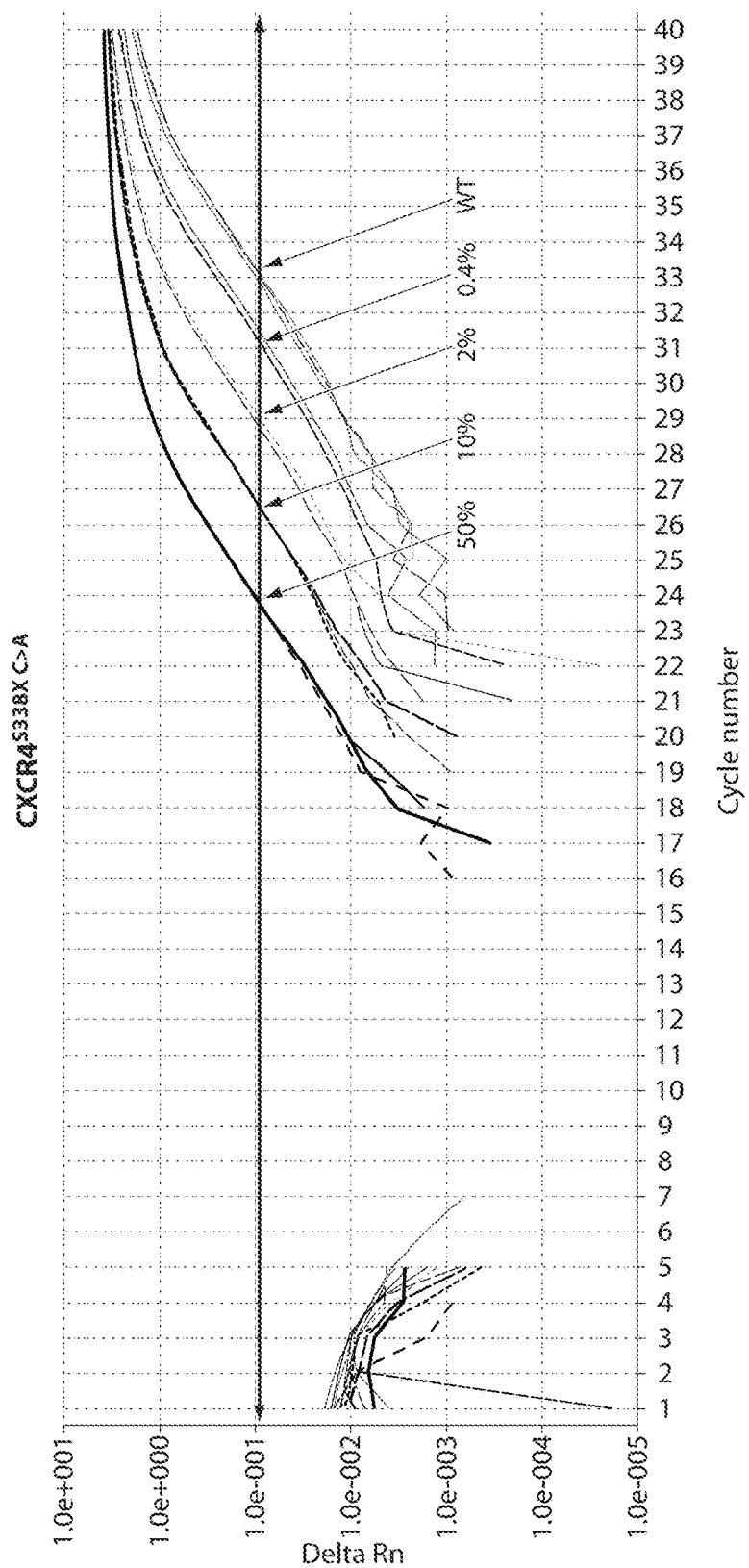
(FIG. 1A) Delta reaction curve for real time AS-PCR assays for $CXCR4^{S338X\ C>A}$ and $CXCR4^{S338X\ C>G}$ Serial dilutions of DNA from malignant cells isolated from patients with $CXCR4^{WT}$ against those from patients with either $CXCR4^{S338X\ C>A}$ or $CXCR4^{S338X\ C>G}$ were made at the concentrations indicated in the amplification plots. The $CXCR4^{S338X\ C>A}$ allele was detected to a dilution of 0.4%, and the $CXCR4^{S338X\ C>G}$ allele was detected to a dilution of 0.16%.
Figure 1A:
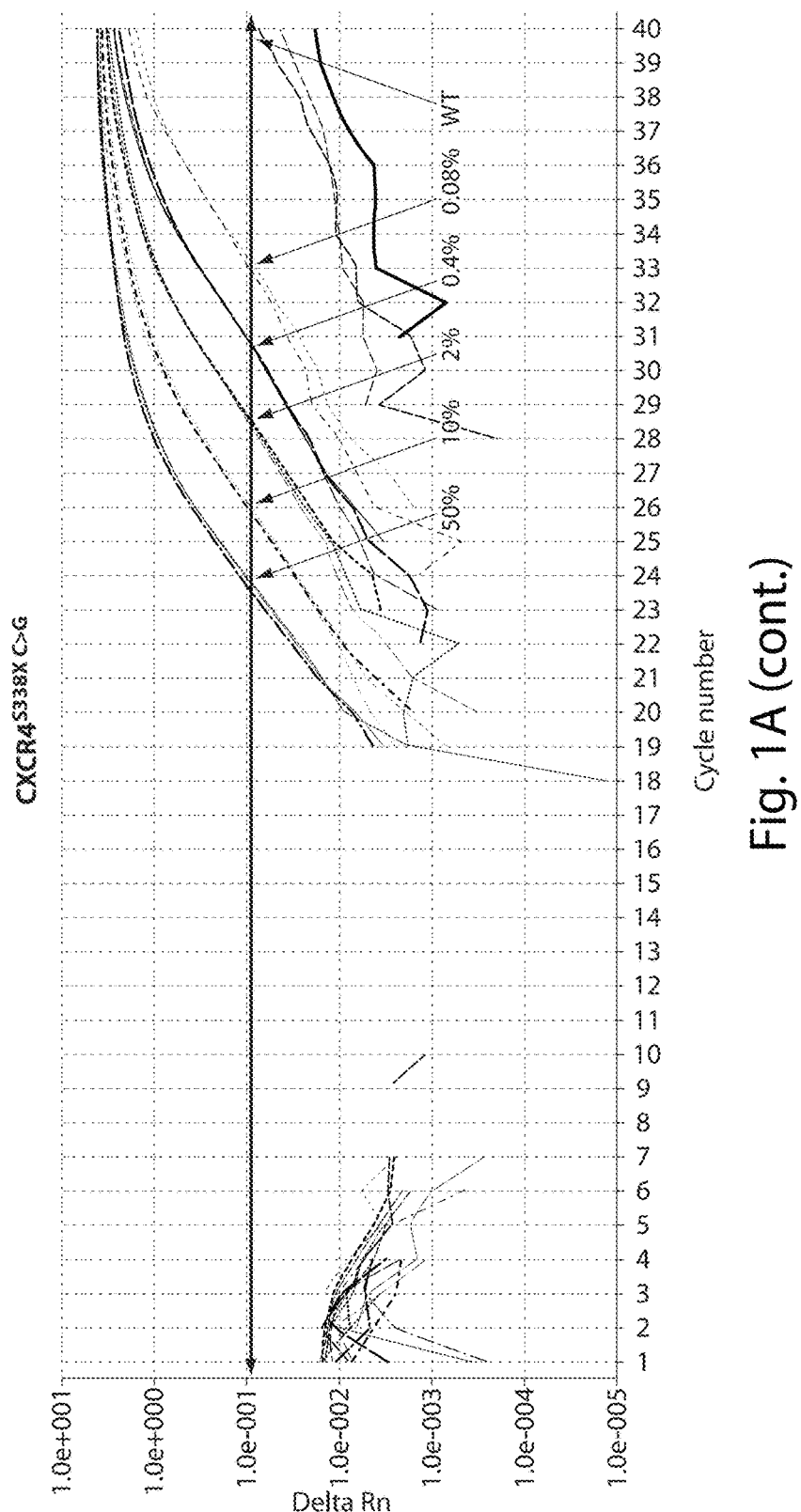
Figure 1B:
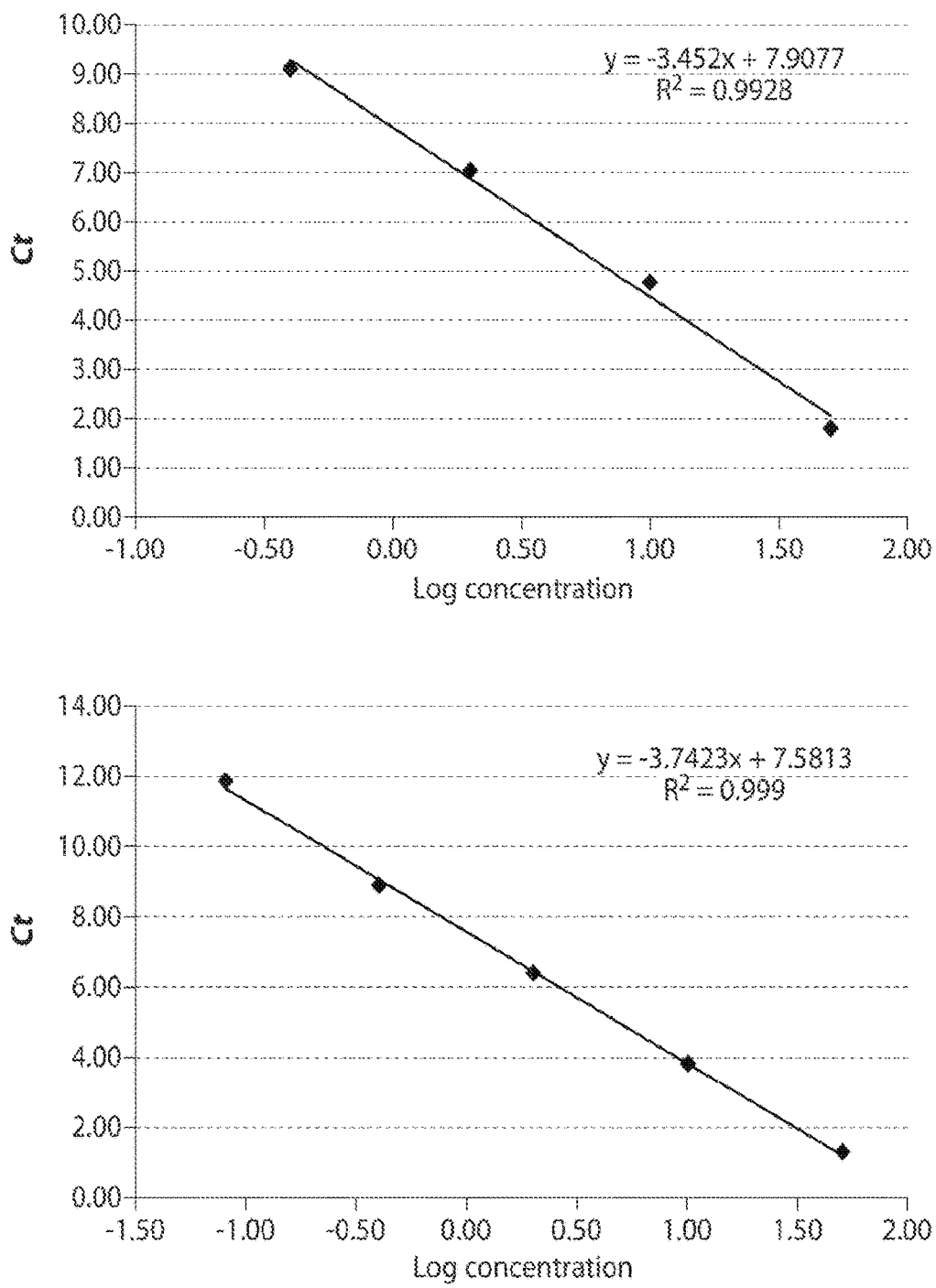
(FIG. 1B) Standard curves for $CXCR4^{S338X\ C>A}$ and $CXCR4^{S338X\ C>G}$ AS-PCR assays. The correlation coefficients and slope values for the assays are shown.
Figure 1C:
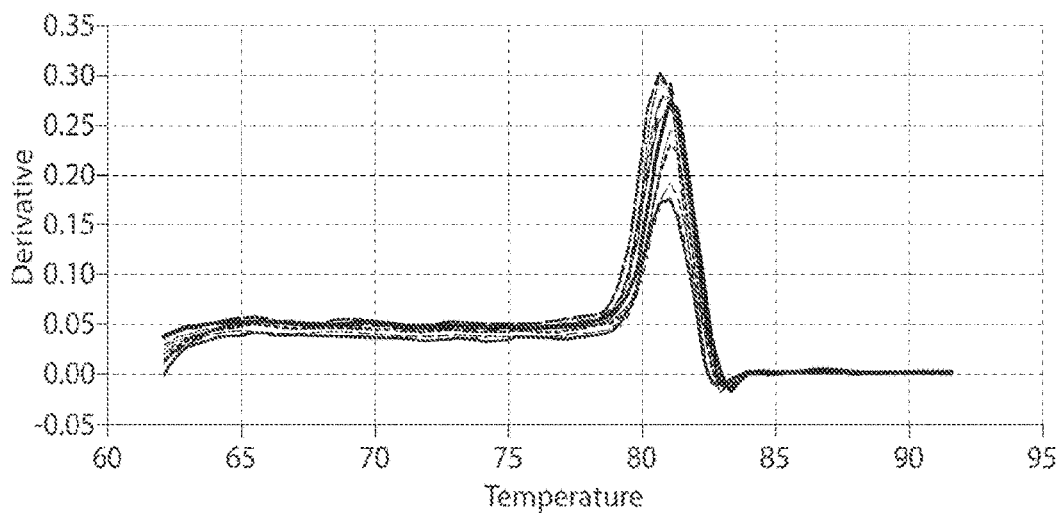
(FIG. 1C) Dissociation curves for real time AS-PCR assays for $CXCR4^{S338X\ C>A}$ and $CXCR4^{S338X\ C>G}$.
Figure 1C:
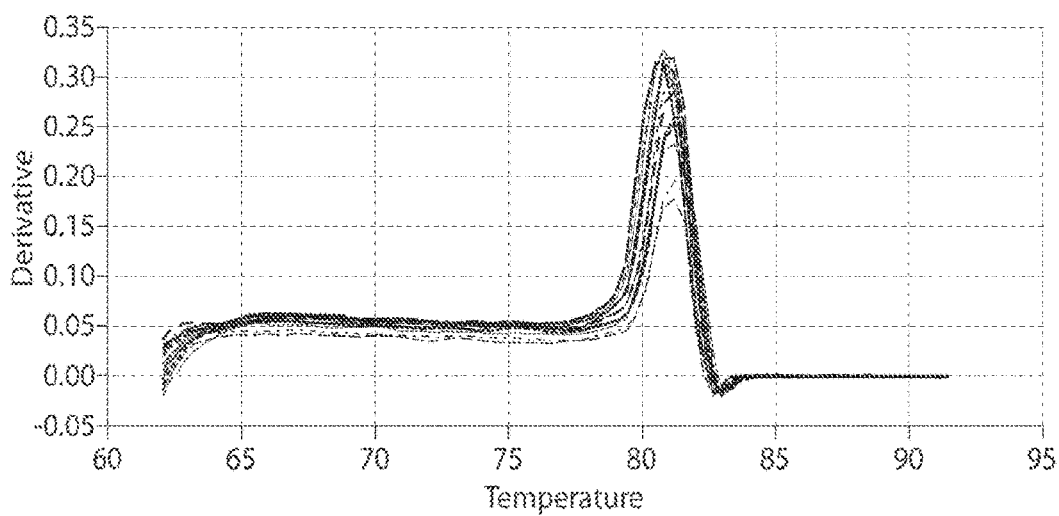

The invention involves the discovery that Waldenstrom's macroglobulinemia can be treated with BTK inhibitors. The invention in one aspect involves administering to a human subject who has Waldenstrom's macroglobulinemia (a "WM subject") a BTK inhibitor in an amount effective to treat the Waldenstrom's macroglobulinemia. In one embodiment Ibrutinib is administered to the WM subject.

BTK inhibitors are known in the art and act on Bruton's tyrosine kinase. There are covalent and non-covalent inhibitors of BTK. Covalent inhibitors bind irreversibly to the target, forming a covalent bond. The covalent BTK inhibitors include ibrutinib/PCI-32765, AVL-101, and AVL-291/292.

Exemplary structures of BTK inhibitors are as follows:

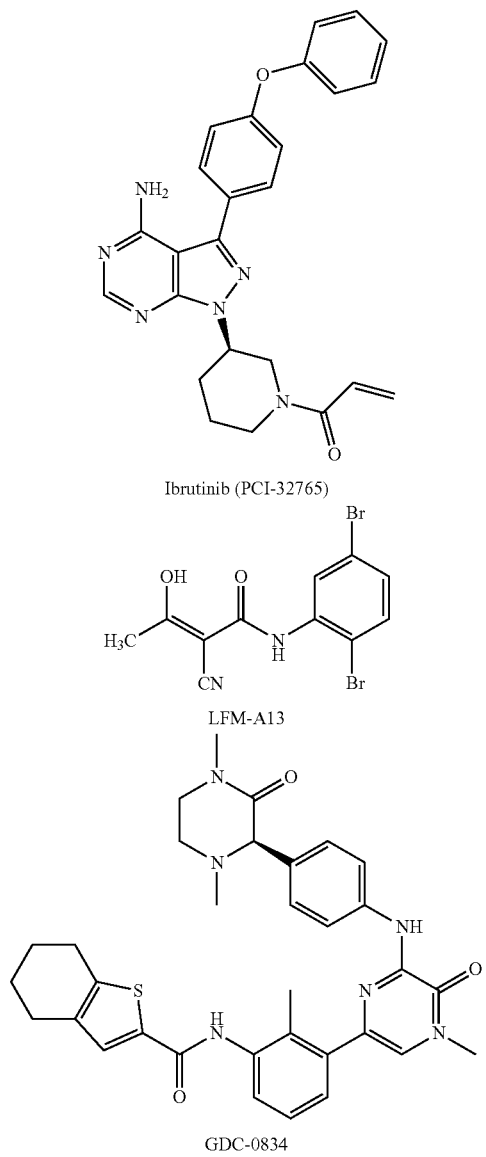

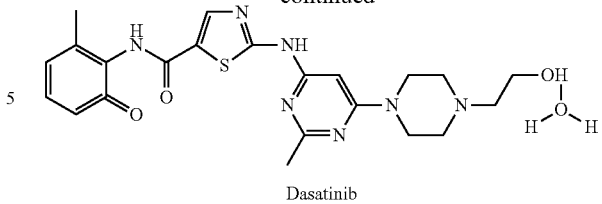

Dasatinib

Ibrutinib is an orally bioavailable, small-molecule inhibitor of Bruton's tyrosine kinase (BTK). Upon oral administration, ibrutinib binds to and irreversibly inhibits BTK activity, thereby interfering with both B-cell activation and B-cell-mediated signaling. Ibrutinib's formula is: 1-[(3R)-3-[4-amino-3-(4-phenoxyphenyl)pyrazolo[3,4-d]pyrimidin-1-yl]piperidin-1-yl]prop-2-en-1-one. AVL-101, AVL-291, and AVL-292 (Avila Therapeutics/Celgene Corporation) are orally active dianilinopyrimidine-based irreversible Btk inhibitors. See Singh J, Russell P, Deqiang N, et al. Protein kinase conjugates and inhibitors. US patent application 20110117073. May 19, 2011. Dasatinib (Sprycel/BMS-354825, Bristol-Myers Squibb) [N-(2-chloro-6-methylphenyl)-2-(6-(4-(2-hydroxyethyl) piperazin-1-yl)-2-methylpyrimidin-4-ylamino)thiazole-5-carboxamide], is a potent, orally active, multikinase BCR/Abl and Src family TKI that is a potent inhibitor of Btk. [See Hantschel O, Rix U, Superti-Furga G. Target spectrum of the BCR-ABL inhibitors imatinib, nilotinib and dasatinib. Leuk Lymphoma. 2008; 49:615-619.] LFM-A13 (alpha-cyano-beta-hydroxy-beta-methyl-N-(2,5-ibromophenyl) propenamide) is a selective Tec family kinase inhibitor that inhibits Btk. [See Mahajan S, Ghosh S, Sudbeck E A, et al. Rational design and synthesis of a novel anti-leukemic agent targeting Bruton's tyrosine kinase (BTK), LFM-A13 [alpha-cyano-beta-hydroxy-beta-methyl-N-(2,5-dibromophenyl) propenamide] J Biol Chem. 1999; 274:9587-9599; Ghosh S, Jennissen J D, Zheng Y, Uckun F M. Three leflunomide metabolite analogs. Acta Crystallogr C. 2000; 56:1254-1257.] ONO-WG-307 (Ono Pharmaceutical) is a multikinase inhibitor with selectivity for Btk. [See Kozaki R, Yoshizawa T, Yasuhiro T, et al. Development of a Bruton's tyrosine kinase (Btk) inhibitor-ONO-WG-307, a potential treatment for B-cell malignancies. Cancer Res. 2012; 72(Suppl B):857;Yasuhiro T, Yoshizawa T, Daub H, Weber C, Narita M, Kawabata K. ONO-WG-307, a novel, potent and selective inhibitor of Bruton's tyrosine kinase (Btk), results in sustained inhibition of the ERK, AKT and PKD signaling pathways. Cancer Res. 2012; 72(Suppl B):2021.] GDC-0834 (Genentech, Gilead): 2.2 GDC-0834 GDC-0834 [R—N-(3-(6-(4-(1,4-dimethyl-3-oxopiperazin-2-yl) phenylamino)-4-methyl-5-oxo-4,5-dihydropyrazin-2-yl)-2-methylphenyl)-4,5,6,7-tetrahydrobenzo[b] thiophene-2-carboxamide], is a reversible, adenosine triphosphate-competitive small-molecule inhibitor of Btk. [See Liu L, Di Paolo J, Barbosa J, Rong H, Reif K, Wong H. Antiarthritis effect of a novel Bruton's tyrosine kinase (BTK) inhibitor in rat collagen-induced arthritis and mechanism-based pharmacokinetic/pharmacodynamic modeling: relationships between inhibition of BTK phosphorylation and efficacy. J Pharmacol Exp Ther. 2011; 338:154-163]

The WM subjects are treated with effective amounts. An effective amount is an amount sufficient in one or more doses to slow, halt or reverse the progression of disease. Waldenström cells express surface immunoglobulin and strongly express CD19, CD20, and CD22 cells. These cells weakly express cytoplasmic immunoglobulin, CD10, and CD38. A slowing, halting, or reversal of the progression of an increase in the number of such cells is one measure of an effective amount. A stabilization of IgM concentration or a decrease in IgM concentration is another measure that may be used. A stabilization in red cell count or an increase in red cell count is another measure that may be used. A stabilization or a decrease in blood viscosity is yet another measure that can be used. A stabilization or lessening of any of the symptoms of Waldenstrom's is still another measure for determining an effective amount.

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

The active agents can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or targeted and direct administration to an affected site. In general the most appropriate route of administration will depend upon a variety of factors including the nature of the agent (e.g., its stability in the environment of the gastrointestinal tract), and/or the condition of the subject.

The active agents are administered in pharmaceutical compositions, which may be or contain pharmaceutically acceptable salts, solvates, hydrates, polymorphs, co-crystals, tautomers, stereoisomers, isotopically labeled derivatives, and prodrugs, and optionally a pharmaceutically acceptable excipient(s). Pharmaceutical compositions can be prepared by any method known in the art of pharmacology. In general, such preparatory methods include the steps of bringing the active compound (the "active ingredient") into association with a carrier or excipient, and/or one or more other accessory ingredients, and then, if necessary and/or desirable, shaping, and/or packaging the product into a desired single- or multi-dose unit. As used herein, a "unit dose" is a discrete amount of the pharmaceutical composition comprising a predetermined amount of the active ingredient.

Relative amounts of the active ingredient, the pharmaceutically acceptable excipient, and/or any additional ingredients in a pharmaceutical composition will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Compounds described herein are typically formulated in dosage unit form for ease of administration and uniformity of dosage. It will be understood, however, that the total daily usage of the pharmaceutical compositions will be decided by the attending physician within the scope of sound medical judgment. The specific therapeutically effective dose level for any particular subject will depend upon a variety of factors including the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs of other treatments used in combination or coincidental with the specific active ingredient employed; and like factors well known in the medical arts.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

The invention also involves the discovery that CXCR4 mutation status impacts whether a WM subject is a good candidate for BTK inhibition treatment. It was discovered, surprisingly, that WM subjects have WHIM-like mutations and that those mutations are B cell somatic mutations. It was further discovered, surprisingly, that WM patients with such WHIM-like mutations are less susceptible to various therapies, including BTK inhibitor treatment and other WM relevant therapeutics (such as, but not limited to, bendamustine, fludarabine, bortezomib, and idelalisib).

Thus, in another aspect of the invention, a method is provided for evaluating a subject having Waldenstrom's macroglobulinemia. The method involves (i) obtaining diseased B cells from the subject, and (ii) performing an assay on the diseased B cells to determine whether the diseased B cells contain a mutation in the carboxyl-terminal cytoplasmic tail of the gene encoding CXCR4, wherein the presence or absence of the mutation in the diseased B cell indicates the subject's likely responsiveness to treatment with various therapies. In one embodiment, the presence of the mutation in the diseased B cell indicates that the subject is unlikely to be responsive to BTK inhibitor treatment. In one embodiment, the presence of the mutation in the diseased B cell indicates that the subject may be responsive to treatment with a BTK inhibitor in combination with a CXCR4 inhibitor, an AKT inhibitor and/or an ERK inhibitor. In another embodiment, the absence of the mutation indicates the subject may be treated with an effective amount of an anti-cancer agent for Waldenstrom's macroglobulinemia, including, optionally, a BTK inhibitor.

The diseased cells are IgM producing B-cells, typically obtained from the bone marrow of the human subject when diagnosing the subject (although it is possible to obtain diseased B cells from lymph node biopsies, spleen biopsies and even circulating blood).

The cells are then evaluated for the presence of a mutation in the carboxyl-terminal cytoplasmic tail of the gene encoding CXCR4 that results in the CXCR4 failing to properly internalize. The mutations capable of causing this are typically frame shift or nonsense mutations in the gene encoding the carboxyl-terminal cytoplasmic tail of CXCR4. The C-terminal domain starts at the end of the 7th transmembrane helix at amino acid 303 (or 909th coding base pair) in the primary isoform (Protein Knowledge base (UniProtKB) P61073 protein or NCBI Reference Sequence: NM_001008540.1 mRNA transcript). The S338X mutation, discussed further below, is the most common observed in connection with the present invention, and it is caused by either a G→C or G→T mutation on chromosome 2 base pair 136872485 (using HG19 human genome reference). These G→C or G→T mutations correspond to a change in the coding transcript for CXCR4 at position 1013, from C→G or C→A, respectively. Either nonsense mutation introduces a pre-mature stop codon ("X") in the transcript of CXCR4, which results in the production of a truncated protein (e.g., a CXCR4 protein with a truncated carboxyl-terminal missing part or all of the cytoplasmic tail). Examples of frameshift mutations include, but are not limited to: a frameshift variant caused by insertion of T at position 136872570 resulting in T311fs; a frameshift variant caused by GAAGACTCAG>AC (SEQ ID NO:17) at position 136872467 resulting in S344fs.

The presence of the mutation can be determined by any number of assays involving evaluation of the CXCR4 protein or nucleic acid. In some embodiments, the assay involves amplifying nucleic acid obtained from a diseased cell and testing for the presence or absence of wild type nucleic acid, testing for the presence of a nucleic acid coding for a truncated tail, testing for a particular mutation, for example, by allele specific-PCR (AS-PCR) or Sanger sequencing and evaluation of the diseased cell nucleic acid sequence. In some embodiments, the presence of the mutation is determined using AS-PCR. Sanger technique is commonly used to sequence genes. However, it is not very sensitive and often requires a minimum mutation burden of 15-20%. In contrast, allele-specific PCR (AS-PCR) is considerably more sensitive, with a range of detection down to 0.1%, and is easier to adopt and provides interpretive results in a clinical diagnostic setting. In any of the forgoing embodiments, B cells can be isolated from other blood cells of the subject prior to determining the presence or absence of the CXCR4 mutation. The isolation may be partial, substantial, or complete, as necessary, to facilitate the isolation and sequencing of the target, such as target nucleic acid.

In some embodiments, DNA, cDNA or mRNA is isolated from a diseased B cell and the presence of the mutation can be assessed through standard Sanger sequencing of CXCR4 nucleic acid using the primers

```
forward:
                                    (SEQ ID NO: 1)
GCTGCCTTACTACATTGGGATCAGC reverse:
                                    (SEQ ID NO: 2)
TTGGCCACAGGTCCTGCCTAGACA.
```

Subjects having a mutation in the carboxyl-terminal cytoplasmic tail of the gene encoding CXCR4 that results in the CXCR4 failing to properly internalize can then be identified. As used herein, identified means identified in written or electronic form. The subject can be identified as having a CXCR4 tail mutation. The subject having the mutation in the diseased B cell can be identified as unlikely to be responsive to various therapies such as treatment with only a BTK inhibitor.

In any of the foregoing embodiments, the method can involve obtaining non-diseased cells from the subject, and performing an assay on the cells to determine whether the cells contain a mutation in the carboxyl-terminal cytoplasmic tail of the gene encoding CXCR4. Subjects having WM, thus, can also have non-diseased cells tested for the presence of a mutation in the carboxyl-terminal cytoplasmic tail of the gene encoding CXCR4 that results in the CXCR4 failing to properly internalize. As mentioned above, the mutation is a somatic mutation, and other cells, such as T cells or virtually any non B cell, of the subject, would be expected to have wild type CXCR4. This can be determined in assays as outlined herein for diseased cells.

Evaluating the presence of a CXCR4 tail mutation in a B cell and the absence of that mutation in another non-diseased cell is another aspect of the invention. It was discovered, surprisingly, that the CXCR4 mutation was a somatic mutation in WM subjects, whereas it is a germ line mutation in WHIM. WM then can be diagnosed, in part, by the presence of the mutation only in diseased B cells. A subject having such a genetic profile can be identified as having the somatic mutation in diseased B cells but not in other cells.

Thus, in this aspect of the invention, a method is provided for evaluating a subject. The method involves obtaining B cells from the subject, performing an assay on the diseased B cells to determine whether the diseased B cells contain a mutation in the carboxyl-terminal cytoplasmic tail of the gene encoding CXCR4, obtaining non-B cells or non-diseased cells from the subject, and performing an assay on the cells to determine whether the cells contain a mutation in the carboxyl-terminal cytoplasmic tail of the gene encoding CXCR4. In some embodiments, the subject with a mutation in the diseased cells, but not the non-diseased cells, is identified as having WM. In some embodiments, the subject with a mutation in the diseased cells and also in the non-diseased cells, is identified as not having WM.

In any of the evaluation/diagnostic methods described herein, the method can involve first performing a test on the subject to determine if the subject has or is suspected of having Waldenstrom's macroglobulinemia. To diagnose a subject as having or suspected of having Waldenström's, blood and urine tests are usually performed as well as a bone marrow biopsy. Test for determining whether a subject has Waldenstrom's macroglobulinemia depend on a significant monoclonal IgM spike evident in blood tests and malignant cells consistent with the disease in bone marrow biopsy samples. Blood tests show the level of IgM in the blood and the presence of proteins such as cold agglutinins, or tumor markers, that are the key symptoms of WM. In WM the level of IgM is high but the IgG level is often low. A bone marrow biopsy provides a sample of bone marrow, usually from the back of the pelvis bone. The sample is extracted through a needle and examined under a microscope. A pathologist identifies the particular lymphocytes that indicate WM. To diagnose WM, at least 10% of the cells in the bone marrow must be lymphoplasmacytoid lymphoma cells. Flow cytometry may be used to examine markers on the cell surface or inside the lymphocytes. Additional tests such as computed tomography (CT or CAT) scan may be used to evaluate the chest, abdomen, and pelvis, particularly swelling of the lymph nodes, liver, and spleen. A skeletal survey can help distinguish between WM and multiple myeloma. Anemia is typically found in 80% of patients with WM. Leukopenia, and thrombocytopenia may be observed. Neutropenia may also be found in some patients. In some embodiments, diagnosis of WM comprises determining whether the subject has a mutation at position 38182641 in chromosome 3p22.2 (see WO 2013/006443).

According to another aspect of the invention, a method of treating a subject is provided. The method involves obtaining diseased B cells from a subject having Waldenstrom's macroglobulinemia, and determining whether the diseased B cells contain a mutation in the carboxyl-terminal cytoplasmic tail of the gene encoding CXCR4, wherein if the subject has Waldenstrom's macroglobulinemia, then the presence or absence of the mutation in the diseased B cell indicates the subject's likely responsiveness to treatment with various therapies, including BTK inhibitor treatment and other WM relevant therapeutics (such as, but not limited to, bendamustine, fludarabine, bortezomib, and idelalisib).

In one aspect of the invention, a method is provided for treating a subject having Waldenstrom's macroglobulinemia. The method involves obtaining diseased B cells from the subject, performing an assay on the diseased B cells to determine whether the diseased B cells contain a mutation in the carboxyl-terminal cytoplasmic tail of the gene encoding CXCR4, and if the subject has a mutation in the carboxyl-terminal cytoplasmic tail of the gene encoding CXCR4, then administering to the subject an effective amount of (i) an anti-cancer agent for Waldenstrom's macroglobulinemia that is not a BTK inhibitor or (ii) a BTK inhibitor in combination with a CXCR4 inhibitor, an AKT inhibitor and/or an ERK inhibitor; or if the subject does not have a mutation in the carboxyl-terminal cytoplasmic tail of the gene encoding CXCR4, then administering to the subject an effective amount of an anti-cancer agent for Waldenstrom's macroglobulinemia, optionally a BTK inhibitor. In some embodiments, the subject is administered an anti-cancer agent, such as but not limited to bendamustine, fludarabine, bortezomib, idelalisib and a BTK inhibitor, in combination with a CXCR4 inhibitor, an AKT inhibitor and/or an ERK inhibitor if the subject has a mutation in the carboxyl-terminal cytoplasmic tail of the gene encoding CXCR4.

In another aspect of the invention, a method is provided for treating a subject having Waldenstrom's macroglobulinemia. The method involves directing a test on diseased B cells obtained from the subject to determine whether the diseased B cells contain a mutation in the carboxyl-terminal cytoplasmic tail of the gene encoding CXCR4, and if the subject has a mutation in the carboxyl-terminal cytoplasmic tail of the gene encoding CXCR4, then administering, or directing the administration of, to the subject an effective amount of (i) an anti-cancer agent for Waldenstrom's macroglobulinemia that is not a BTK inhibitor or (ii) a BTK inhibitor in combination with a CXCR4 inhibitor, an AKT inhibitor and/or an ERK inhibitor; or if the subject does not have a mutation in the carboxyl-terminal cytoplasmic tail of the gene encoding CXCR4, then administering to the subject an effective amount of an anti-cancer agent for Waldenstrom's macroglobulinemia, optionally a BTK inhibitor. In some embodiments, the subject is administered an anti-cancer agent, such as but not limited to bendamustine, fludarabine, bortezomib, idelalisib and a BTK inhibitor, in combination with a CXCR4 inhibitor, an AKT inhibitor and/or an ERK inhibitor if the subject has a mutation in the carboxyl-terminal cytoplasmic tail of the gene encoding CXCR4.

In another aspect of the invention, a method is provided for treating a subject having Waldenstrom's macroglobulinemia. The method involves (a) selecting the subject on the basis that the subject is known to have contain a mutation in the carboxyl-terminal cytoplasmic tail of the gene encoding CXCR4; and (b) administering, or directing the administration of, an effective amount of (i) an anti-cancer agent that is not a BTK inhibitor to the subject because the subject has a mutation in the carboxyl-terminal cytoplasmic tail of the gene encoding CXCR4 or (ii) a BTK inhibitor in combination with a CXCR4 inhibitor, an AKT inhibitor and/or an ERK inhibitor.

As used herein, directing means giving written or electronic instructions to conduct the applicable activity.

Determining whether a WM subject has a mutation in the carboxyl-terminal cytoplasmic tail of the gene encoding CXCR4 can be carried out as described herein.

In any of the aspects of the invention involving treatments, various agents are contemplated. Anti-cancer agents for Waldenstrom's macroglobulinemia that are not a BTK inhibitors include alkylators, anthracycline, nucleoside analogs, an anti-CD20 monoclonal antibody, thalidomide, immunomodulatory derivatives of thalidomide, interferon, proteasome inhibitors, protein kinase C inhibitors, monoclonal antibody to CD52 and microtubule inhibitors. Particular anti-cancer agents for Waldenstrom's macroglobulinemia include chlorambucil, Carmustine (bis-chloroethylnitrosourea), cyclophosphamide, vincristine, melphalan, prednisone, cladribine (2-chlorodeoxyadenosine), adriamycin, rituximab, thalidomide, dexamethasone, alpha-interferon (α-IFN), carfilzomib, oprozomib, ixazomib (proteasome inhibitors), UCN-01 (a protein kinase C inhibitor), Campath-1H (monoclonal antibody to CD52), and dolastatin (a microtubule inhibitor).

BTK inhibitors are as described above.

CXCR4 inhibitors are known in the art. The first clinically tested CXCR4 antagonist was plerixafor for the mobilization of hematopoietic stem cells. Another small molecule, AMD070, is an orally active CXCR4 antagonist under clinical investigation for the prevention of T-tropic HIV infection.

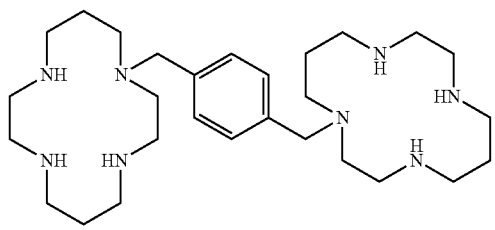

(Plerixafor, AMD3100)

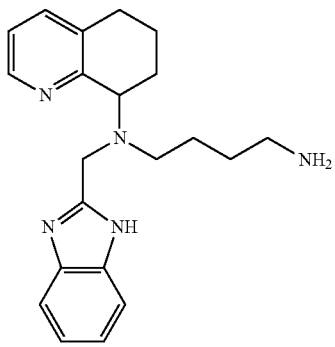

(AMD070)

Newer CXCR4 antagonists are under clinical evaluation for therapeutic intervention in various cancers, hematologic and vascular disorders, HIV infection, and other immune system disorders involving the modulation of the SDF-1/CXCR4 axis, such as rheumatoid arthritis and lupus [See Burger J A, Stewart D J. CXCR4 chemokine receptor antagonists: perspectives in SCLC. Expert Opin Investig Drugs. 2009; 18:481-90; Harvey J R, Mellor P, Eldaly H, Lennard T W, Kirby J A, Ali S. Inhibition of CXCR4-mediated breast cancer metastasis: a potential role for heparinoids?. Clin Cancer Res. 2007; 13:1562-70; Wilson L J, Liotta D C. Emergence of small-molecule CXCR4 antagonists as novel immune and hematopoietic system regulatory agents. Drug Development Research. 2011; 72:598-602. Many newer CXCR4 inhibitors are cationic molecules able to bind the predominantly anionic extracellular domain of CXCR4. They belong to different chemical classes including cyclic penta- and tetra-peptides, diketopiperazine mimetics, bicyclams, tetrahydroquinolines, thiazolylisothiourea derivatives, benzodiazepines, dipicolylamine-zinc(II) complexes and naturally occurring derivatives. Structures of select cyclic pentapeptide-based CXCR4 antagonists are as follows:

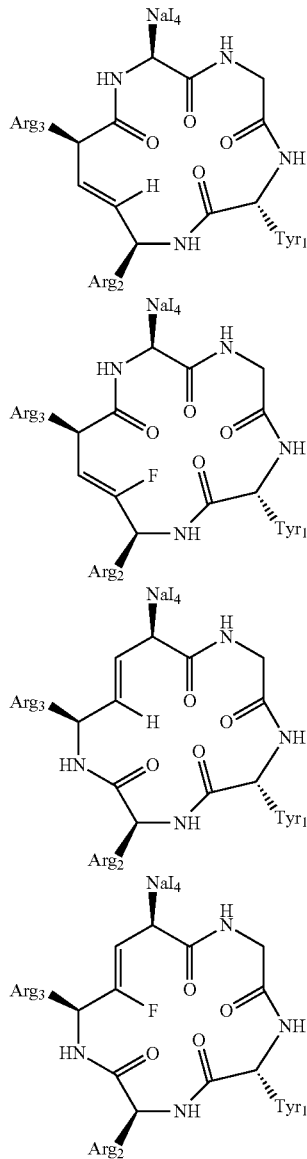

Exemplary structures of representative examples of a monomeric cyclic pentapeptide-based CXCR4 antagonist, two dimeric derivatives and a dimeric Ga-labeled DOTA complex are as follows:

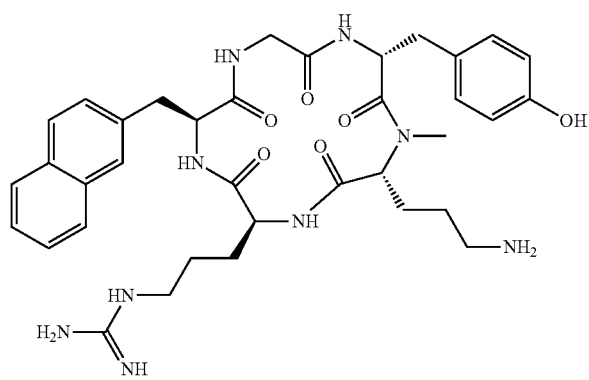

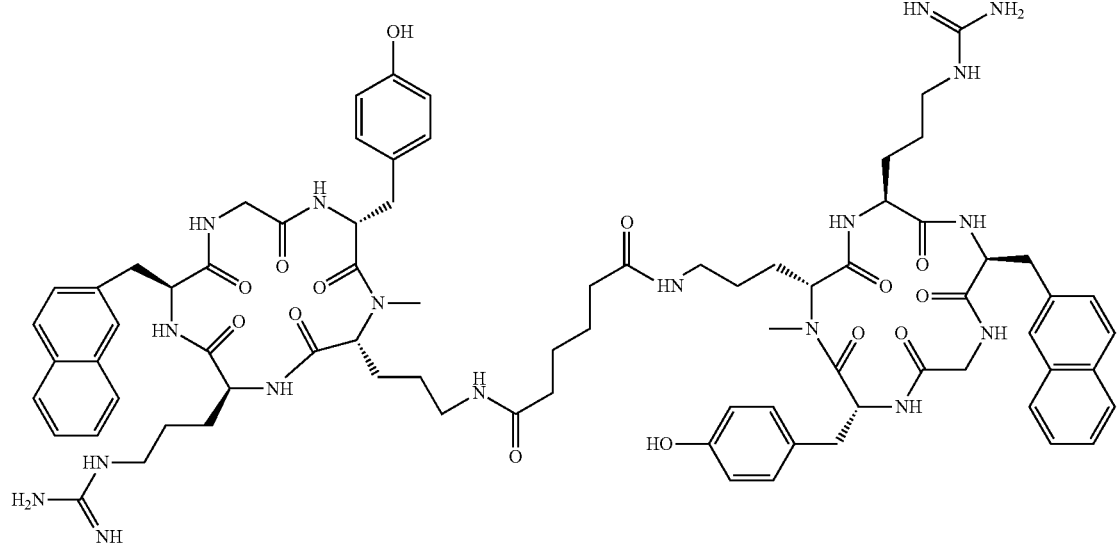
33
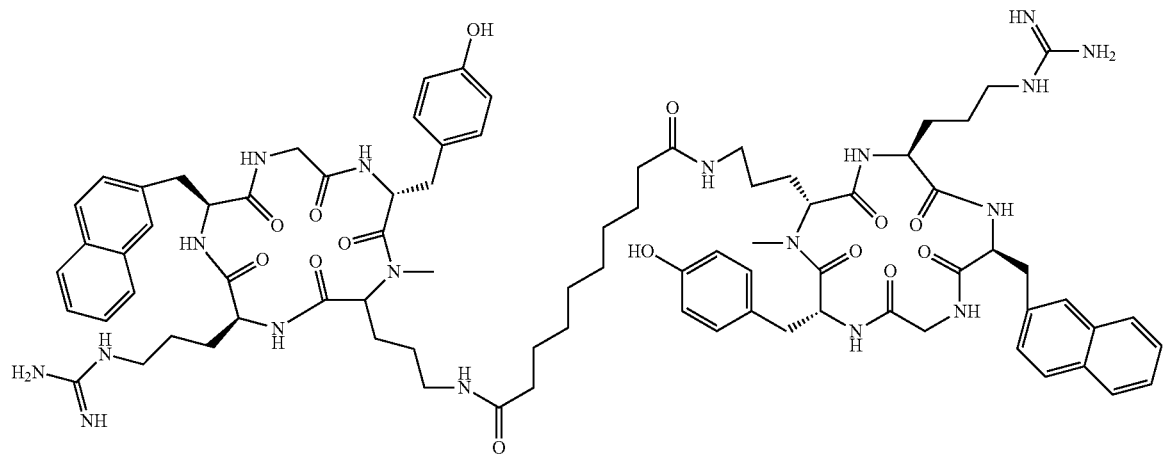
34
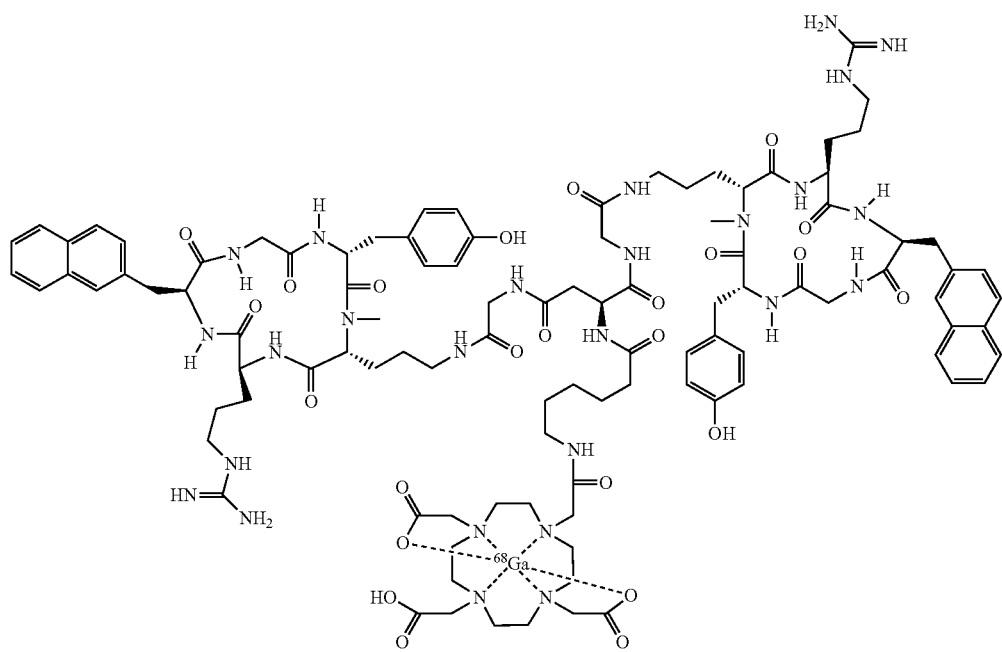
35

Exemplary structures of indole-based CXCR4 antagonists are as follows:
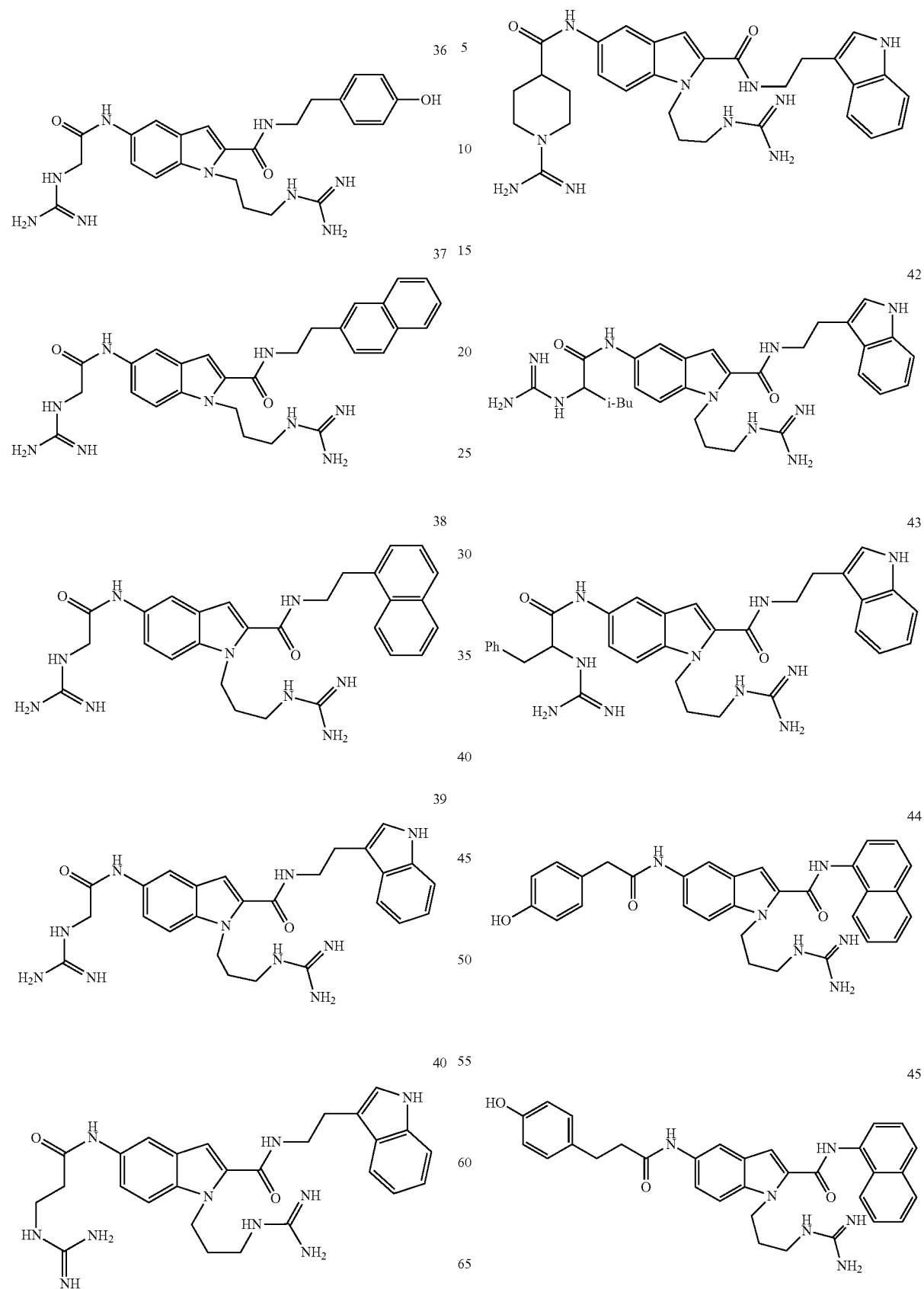

46
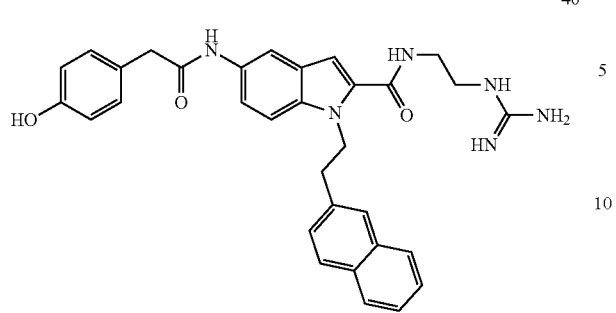
47
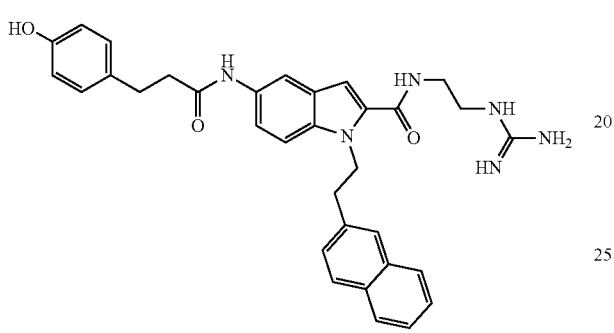
Exemplary structures of tetrahydroquinoline-based CXCR4 antagonists are as follows:
48
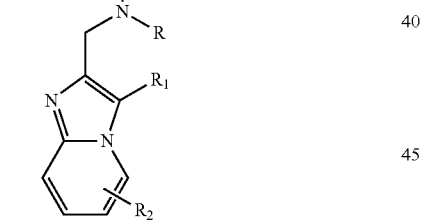
R = alkyl, heteroaryl
R₁ = N-containing chain
R₂ = N-containing chain
49
IC$_{50}$ = 0.044 μM
50
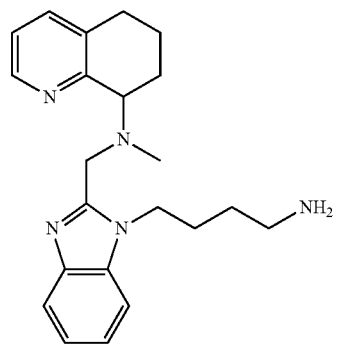
IC$_{50}$ = 0.144 μM
51
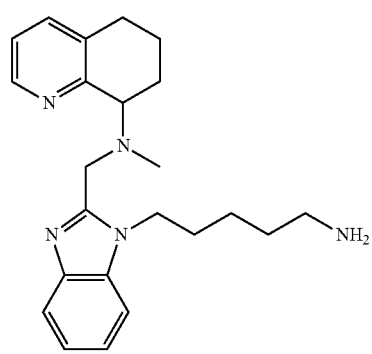
IC$_{50}$ = 0.228 μM
52
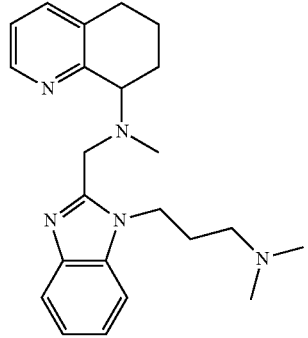
IC$_{50}$ = 0.017 μM
53
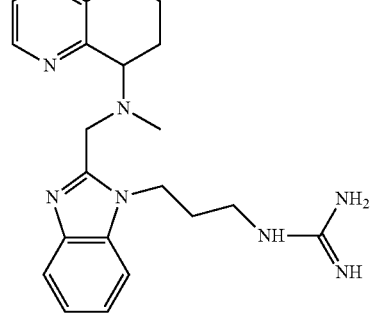
IC$_{50}$ = 0.026 μM 25
-continued
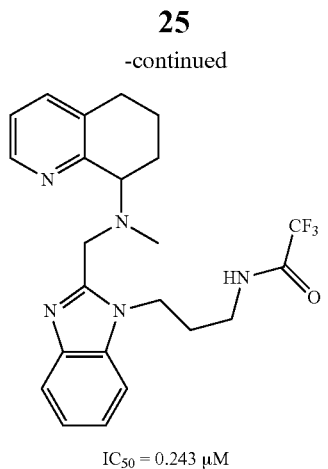
54
IC$_{50}$ = 0.243 μM
Exemplary structures of tetrahyidroquinoline-based CXCR4 antagonists are as follows:
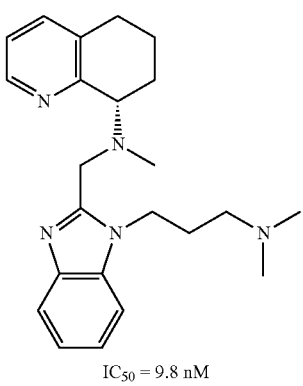
74
IC$_{50}$ = 9.8 nM
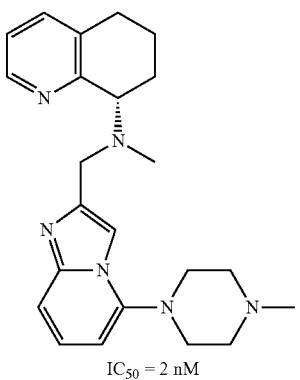
75
IC$_{50}$ = 2 nM
26
-continued
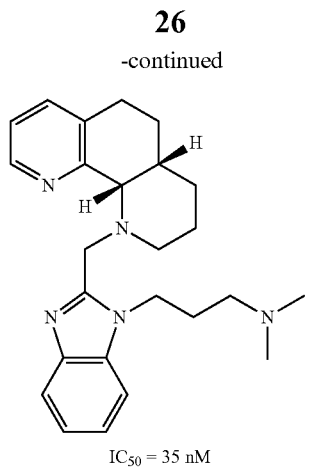
76a
IC$_{50}$ = 35 nM
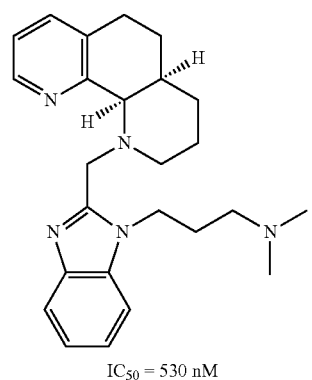
76b
IC$_{50}$ = 530 nM
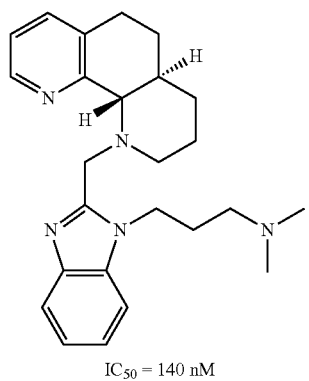
76c
IC$_{50}$ = 140 nM
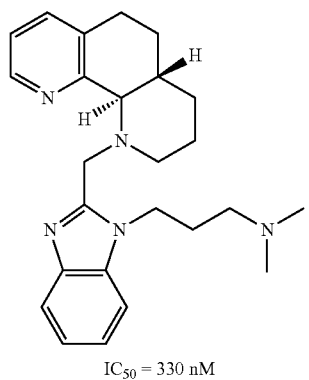
76d
IC$_{50}$ = 330 nM

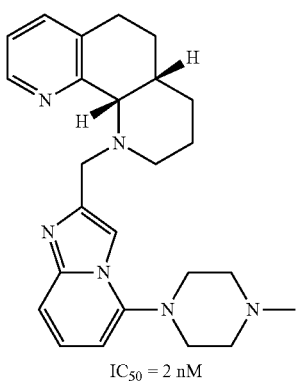

IC$_{50}$ = 2 nM

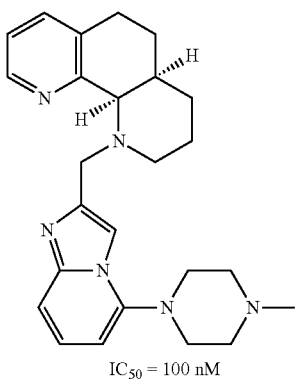

IC$_{50}$ = 100 nM

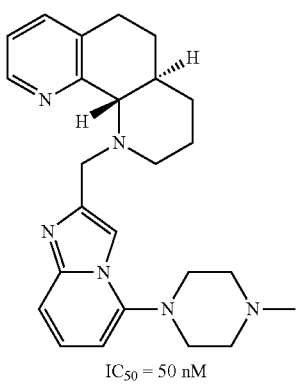

IC$_{50}$ = 50 nM

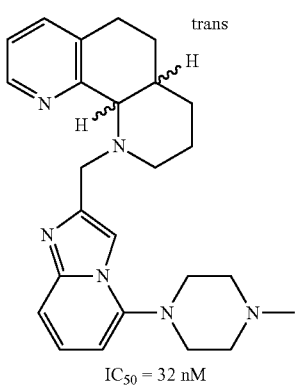

IC$_{50}$ = 32 nM

See also: Skerlj R, Bridger G, McEachern E, Harwig C, Smith C, Kaller A. et al. Design of novel CXCR4 antagonists that are potent inhibitors of T-tropic (X4) HIV-1 replication. Bioorg Med Chem Lett. 2011; 21:1414-8; Skerlj R, Bridger G, McEachern E, Harwig C, Smith C, Wilson T. et al. Synthesis and SAR of novel CXCR4 antagonists that are potent inhibitors of T tropic (X4) HIV-1 replication. Bioorg Med Chem Lett. 2011; 21:262-6; Miller J F, Gudmundsson K S, D'Aurora Richardson L, Jenkinson S, Spaltenstein A, Thomson M. et al. Synthesis and SAR of novel isoquinoline CXCR4 antagonists with potent anti-HIV activity. Bioorg Med Chem Lett. 2010; 20:3026-30. In some embodiments, the CXCR4 inhibitor is AMD3100, BMS936564 (a fully human anti-CXCR4 antibody; Clin Cancer Res. 2013 Jan. 15; 19(2):357-66), AMD-070, TG-0054 (Burixafor; Hsu et al. Cell Transplant. 2014 May 12. [Epub ahead of print]).

AKT inhibitors are known in the art and act on protein kinase B (PKB). Exemplary AKT inhibitors described in WO 2004/022569, WO 2011/050016, WO 2012/177925, and WO2010/091824 are incorporated herein by reference. In some embodiments, the AKT inhibitor is MK-2206 (Hirai et al. Mol Cancer Ther July 2010 9:1956-1967) and AZD-5363 (Davies et al. Mol Cancer Ther. 2012 April; 11(4): 873-87).

ERK inhibitors are known in the art and act on extracellular-signal-regulated kinases (ERK). Exemplary ERK inhibitors described in WO 2008/156739, WO 2001/056993, WO 2013063214, and WO2012/030685 are incorporated herein by reference. Other examples include without limitation, selumetinib (also known as AZD6244), U0126, PD98059, PD0325901, AZD8330(ARRY-42704), CI-1040 (PD 184352), PD318088 (see, for example, WO2012/160130). In some embodiments, the ERK inhibitor is AS-703026 (Br J Haematol. 2010 May; 149(4):537-49), AZD-6244 or U0126.

According to one aspect, the present invention provides a method to distinguish Waldenstrom's macroglobulinemia from other B cell neoplasms. The method comprises performing an assay on a biological sample obtained from a subject in need thereof to determine whether the subject has a mutation at position 38182641 in chromosome 3p22.2; performing an assay on diseased B cells obtained from the subject to determine whether the diseased B cells contain a mutation in the carboxyl-terminal cytoplasmic tail of the gene encoding CXCR4, wherein the subject has Waldenstrom's macroglobulinemia if the subject has a mutation at position 38182641 in chromosome 3p22.2 and a mutation in the carboxyl-terminal cytoplasmic tail of the gene encoding CXCR4.

Other B cell neoplasms are B-cell malignancies, other than WM, that have overlapping clinical and laboratory features. Examples of other B cell neoplasms include nodal marginal zone lymphomas, extranodal marginal zone lymphoma of mucosa-associated lymphoid tissue (MALT lymphoma), splenic B cell marginal zone lymphoma, and plasma cell myeloma.

"A subject in need thereof" is a subject that presents one or more symptoms or clinical features of WM which overlap with one or more symptoms of at least one of the B cell neoplasms described above. Thus, the subject is an individual who is suspected of having either WM or one of the other B cell neoplasm. The subject is selected for further diagnostic analysis by a medical practitioner (e.g., a doctor, nurse, clinical laboratory practitioner, genetic counselor, etc.), a healthcare organization, or a clinical laboratory.

The one or more symptoms or clinical features of WM include anemia, hyper-viscosity, neuropathy, coagulopathies, splenomegaly, hepatomegaly, adenopathy, and an IgM serum paraprotein. In addition, the subject may also present one or more of the following clinical features or symptoms of other B cell neoplasms: asymptomatic localized or generalized peripheral lymphadenopathy, plasmacytic difference, bone marrow involvement, autoimmune thrombocytopenia, peripheral blood villous lymphocytes, end organ damage (hypercalcemia, renal insufficiency, bone lesions), recurrent infections, elevated creatine, hyperuricemia, and hypoalbunemia. The subject suspected of having either WM or one of the other B cell neoplasm is assessed for the presence of a mutation at position 38182641 in chromosome 3p22.2, and for the presence of a mutation in the carboxyl-terminal cytoplasmic tail of the gene encoding CXCR4, wherein the subject has Waldenstrom's macroglobulinemia if the subject has both mutations.

Non-limiting examples of the biological sample obtained from the subject to determine whether the subject has a mutation at position 38182641 in chromosome 3p22.2 include bone marrow, lymph node, spleen or blood. Obtaining a biological sample of a subject means taking possession of a biological sample of the subject. Obtaining a biological sample from a subject means removing a biological sample from the subject. Therefore, the person obtaining a biological sample of a subject and determining the presence of the mutation in the sample does not necessarily obtain the biological sample from the subject. In some embodiments, the biological sample may be removed from the subject by a medical practitioner (e.g., a doctor, nurse, or a clinical laboratory practitioner), and then provided to the person determining the presence of the mutation. The biological sample may be provided to the person determining the mutation by the subject or by a medical practitioner (e.g., a doctor, nurse, or a clinical laboratory practitioner). In some embodiments, the person determining the mutation obtains a biological sample from the subject by removing the sample from the subject.

The term "mutation at position 38182641 in chromosome 3p22.2" means any change or difference in the nucleic acid or protein sequence of MYD88 as compared to the wild type sequence that results in the activation of MYD88 which leads to the activation of NF-κB. Mutations include, but are not limited to, nonsense mutations, missense mutations, frameshift mutations, rearrangement mutations, insertion mutations and deletion mutations. In some embodiments, the mutation is a somatic mutation at position 38182641 in chromosome 3p22.2 which results in a single nucleotide change from TC in the myeloid differentiation primary response (MYD88) gene, and a predicted non-synonymous change at amino acid position 265 from leucine to proline (L265P).

One skilled in the art will appreciate that many suitable methods, in addition to and including the ones discussed in the examples, can be used to detect mutations in the MYD88 and/or CXCR4 gene in the methods described herein. Detection methods that can be used include, but are not limited to, direct sequencing, DNAchip technologies, mass spectroscopy, polymerase chain reaction (PCR), allele specific polymerase chain reaction, real time polymerase chain reaction, reverse transcriptase PCR, electrophoretic mobility, nucleic acid hybridization, fluorescent in situ hybridization, and denaturing high performance liquid chromatography.

In some embodiments, mutations in the MYD88 gene may be detected by allele specific polymerase chain reaction (AS-PCR). For AS-PCR, allele specific primers are used which hybridize at or near their 3' ends to a particular mutation in the MYD88 gene. If the mutation is not present, the 3'-terminal mismatched primer does not initiate replication, and an amplification product is not observed. In some embodiments, only the forward primer or the reverse primer hybridizes at or near its 3' ends to a particular mutation in the MYD88 gene. In some embodiments, both the forward and the reverse primer hybridize at or near their 3' ends to a particular mutation in the MYD88 gene. In some embodiments, the allele specific primer is 5'-CCT TGT ACT TGA TGG GGA aCG-3' (SEQ ID NO: 3) (see, for example, WO 2013/006443).

The present disclosure is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1. Somatic Activating Mutations in CXCR4 are Common in Patients with Waldenstrom's Macroglobulinemia, and their Expression in WM Cells Promotes Resistance to Ibrutinib Waldenstrom's macroglobulinemia (WM) is an indolent non-Hodgkin's lymphoma characterized by the accumulation of IgM secreting lymphoplasmacytic cells in the bone marrow. CXCR4 is a chemokine receptor that promotes the survival, migration, and adhesion to the bone marrow stroma of lymphoplasmacytic cells (LPC) through interactions with its ligand CXCL12. Through whole genome sequencing, somatic mutations in CXCR4 were identified that affected ⅓ of WM patients. These mutations were identical or functionally similar to those associated with *Warts, Hypogammaglobulinemia, Infection, and Myelokathexis* (WHIM) syndrome, a rare autosomal dominant genetic disorder that is caused by frame shift or nonsense mutations in the carboxyl-terminal cytoplasmic tail of CXCR4. In WHIM syndrome, loss of the C-terminal tail of CXCR4 impairs receptor internalization, thereby prolonging G-protein and β-arrestin signaling (Lagane et al., *Blood.* 2008; 112:34-44).

Bruton's tyrosine kinase (BTK) is a known downstream target of CXCR4, and the BTK inhibitor ibrutinib has been shown to induce LPC cell death in WM. The instant study sought to clarify if ibrutinib activity in WM LPCs was modulated by WHIM-like mutations in CXCR4.

Methods

First, the frequency of WHIM-like mutations in 87 untreated WM patients by Sanger sequencing was determined. The most common CXCR4 somatic mutation identified (S338X) in these studies was then cloned by PCR from CD19+ LPCs from a WM patient with this somatic mutation. Wild type (WT) and S338X CXCR4 cDNAs were subcloned into plenti-IRES-GFP vector, and transduced using an optimized lentiviral based strategy into BCWM.1 WM cells, an established WM cell line (Ditzel et al., *Exp Hematol.* 2007; 35(9):1366-75). Five days after transduction, GFP positive cells were sorted and used for functional studies. Surface expression of CXCR4 was determined by flow cytometeric analysis using a PE-conjugated anti-CXCR4 monoclonal antibody. The expression of phosphorylated BTK, AKT, and ERK1/2 was determined by western blot analysis. Cell proliferation was measured with alamar blue.

Results

Sanger sequencing identified nonsense or frame shift mutations (WHIM-like) in the C-terminal tail of CXCR4 in 28 of 87 (32%) patients, the most common of which was a non-sense mutation (S338X) that was present in 12 patients.

BCWM.1 cells were then transduced with control vector, CXCR4 wild type or CXCR4 S338X mutant expressing vectors. Expression was confirmed by cDNA Sanger sequencing. Stably transduced cells exposed to ibrutinib (0.5 uM or 1 uM) showed significantly reduced cell proliferation (p<0.005). Ibrutinib treated control vector and CXCR4 wild-type transduced cells showed suppressed tumor cell growth even in the presence of the CXCR4 ligand CXCL12 (20 nM), whereas cells transduced with CXCR4 S338X WHIM-like mutation demonstrated resistance to ibrutinib growth effect (p<0.005). In turn, this rescue could be blocked by treatment with 30 nM of the CXCR4 specific inhibitor AMD3100 confirming that this effect was mediated through CXCR4 (p<0.005). Phosphorylated BTK, ERK1/2 and AKT signaling increased following CXCL12 stimulation in all transduced cells, while ibrutinib inhibited their activation in control vector and CXCR4 wild-type, but not CXCR4 S338X mutant cells. CXCR4 triggered signaling by CXCL12 in these experiments was confirmed by pre-treatment with AMD3100.

Conclusions

By Sanger sequencing, WHIM-like CXCR4 somatic mutations are observed in ⅓ of untreated WM patients. WHIM-like CXCR4 mutations are associated with resistance to ibrutinib mediated ERK1/2 and AKT signaling, as well as growth suppression in the presence of the CXCR4 ligand, CXCL12 in WM cells. Inhibition of CXCR4 in CXCR4 mutant WM cells re-established sensitivity to BTK inhibition. These studies have important implications for CXCR4 modulation in the treatment of WM. Further, as described in Example 2, CXCR4 mutation status is predictive of outcome for WM patients undergoing BTK inhibition therapy.

Example 2: CXCR4 Mutation Status is Predictive of Patient Response to Treatment with Ibrutinib in WM Ibrutinib is a newly discovered drug that is being developed as an anti-cancer agent. Ibrutinib is a BTK inhibitor drug which interrupts B cell receptor (BCR) signaling in lymphomas by selectively and irreversibly binding to the BTK protein, which then results in malignant cell death. This drug has been used in laboratory experiments and other research studies in B-cell malignancies.

However, based on the knowledge that mutations in the C-terminal tail of CXCR4 conferred resistance of WM cells to ibrutinib in vitro (as described in Example 1), it was hypothesized that patients having such mutations would have reduced or no responsiveness to ibrutinib treatment.

Methods

Forty (40) WM patients were included in the study. Patients were genotyped to determine CXCR4 mutation status. Baseline measurements for the following clinical parameters were taken prior to treatment: serum IgM levels; serum IgM M-spike levels; platelet count; serum hemoglobin levels; absolute lymphocyte count (ALC); hematocrit (HCT) blood test; and bone marrow involvement.

Following baseline measurements, patients were administered 420 mg ibrutinib orally, once daily in the morning in 4 week cycles until disease progression or intolerance to medication developed. Measurements of the above parameters were taken on or about 4 weeks, 8 weeks, 24 weeks, and thereafter every 12 weeks from start of therapy.

Results

Of the 40 patients, 10 (25%) had detectable mutations in the C-terminal tail of CXCR4. Responses to ibrutinib are shown according to response categories and by major response (PR or VGPR) below:

Categorical

|  | VGPR | PR | MR | SD/PD |
|---|---|---|---|---|
| WT | 4 (13.3%) | 19 63.3%) | 2 (6.7%) | 5 (16.7%) |
| WHIM-Like | 0 (0.0%) | 3 (30%) | 4 (40%) | 3 (30%) |

VGPR: very good partial response, i.e., more than a 90% reduction in serum IgM level;
PR: partial response, i.e., reductions in serum IgM of 50% to up to 90%;
MR: minor response, i.e., reductions in serum IgM of 25% to up to 50%;
SD: stable disease, IgM change of under 25% or an increase of not more than 25% in the absence of any new signs or symptoms of disease, or
PR: progressive disease denoted by more than 25% increase in IgM or development of new or other progressive signs and symptoms of disease).

Major Response

|  | Response | No Response |
|---|---|---|
| WT | 23 (76.7%) | 7 (23.3%) |
| WHIM-Like | 3 (30%) | 7 (70%) |

Overall, 76.7% of patients that were wild type (WT) for CXCR4 showed a major response (PR or VGPR) to ibrutinib treatment; whereas only 30% of patients having mutations in the C-terminal tails (WHIM-like mutations) in CXCR4 showed a major response to treatment. Categorically, the majority of those patients that were wild type for CXCR4 had either a very good partial response i.e. more than a 90% reduction in serum IgM level, or a partial response i.e. reductions in serum IgM of 50% to 90% were 13.3% and 63.3%, respectively. Conversely, of those patients positive for a CXCR4 WHIM-like mutation, none demonstrated a very good partial response, and only 30% showed a partial response.

Of the other clinical parameters tested, patients that were wild type for CXCR4 had statistically significant, greater reductions in IgM M-spike levels (FDR adjusted p-value=0.0116) as compared to those carrying CXCR4 mutations. Wild type patients also had increased absolute lymphocyte counts in response to treatment that were significant (FDR adjusted p-value=0.0013). Differences between platelet levels, hemoglobin levels, hematocrit blood tests, and bone marrow levels were not statistically significant between wild type and CXCR4 mutation status.

Linear and logistic regression analysis was performed to determine the predictive value of the parameters tested. With linear modeling, IgM response (i.e. the best IgM levels achieved/baseline levels), baseline bone marrow involvement, age, sex, MYD88 mutation status, and CXCR4 mutation status were analyzed. The results indicated that baseline bone marrow involvement and age correlates with a better IgM response, and CXCR4 (but not MYD88) mutation status is a negative predictor for response to BTK inhibition.

With logistic regression analysis, of HCT, Age, MYD88 status, CXCR4 status, sex, and baseline bone marrow involvement, only baseline bone marrow involvement and CXCR4 status significantly altered the odds of response attainment. Higher bone marrow involvement at baseline correlated with better odds of PR/VGPR, while CXCR4 mutations decrease the odds of PR/VGPR attainment.

Conclusions

The results of Example 2 confirmed, in vivo, the conclusions of the in vitro study described in Example 1. Mutations in the C-terminus of CXCR4 confers resistance to BTK inhibitors, such as ibrutinib, in WM cells, such that patients having these mutations have either no or a reduced response to BTK inhibition. Knowledge of CXCR4 mutation status is thus important for determining the course of treatment in WM.

Example 3: Development of AS-PCR Assay

Methods
Patient Samples

Thirteen patients meeting consensus diagnostic criteria for WM, and 12 healthy donors were included in assay development. CXCR4S338X AS-PCR assays were then used to examine bone marrow (BM) and peripheral blood (PB) samples from a separate cohort of WM (n=62), IgM MGUS (n=12), MZL (n=18), and CLL patients (n=32), and healthy donors (n=32). The clinical characteristics for WM and IgM MGUS patients whose disease status was defined based on consensus criteria are depicted in Table 1 shown below. MYD88 mutation status was determined by AS-PCR for all subjects. Subject participation was approved by the Harvard Cancer Center/Dana-Farber Cancer Institute Institutional Review Board. All participants provided written consent. DNA for CXCR4 sequencing studies was extracted from samples as previously described (Xu L, et al. MYD88 L265P in Waldenstrom macroglobulinemia, immunoglobulin M monoclonal gammopathy, and other B-cell lymphoproliferative disorders using conventional and quantitative allele-specific polymerase chain reaction. Blood 2013; 121 (11):2051-8; Xu L, et al. Detection of MYD88 L265P in peripheral blood from patients with Waldenström's Macroglobulinemia and IgM Monoclonal Gammopathy of Undetermined Significance. Leukemia 2014; [Epub ahead of print]).

TABLE 1

Baseline characteristics for the 62 WM and 12 IgM MGUS patients whose samples were evaluated by AS-PCR for the CXCR4$^{S338X\ C>A}$ and CXCR4$^{S338X\ C>G}$ variants. Median values are shown with ranges.

| | WM | IGM MGUS |
|---|---|---|
| N= | 62 | 12 |
| Age (years) | 63 | 69 |
| | (range 44-86) | (range 56-82) |
| Gender (M/F) | 48/15 | 6/6 |
| Serum IgM (mg/dL) | 3,610 | 397 |
| | (range 735-8,390) | (range 142-1,640) |
| Hemoglobin (g/dL) | 10.5 | 13.4 |
| | (range 8.2-13.8) | (range 11.9-16.3) |
| Serum $\beta_2$-microglobulin (mg/L) | 3.9 | 1.9 |
| | (range 1.3-14.2) | (range 1.7-3.4) |
| Adenopathy (≥1.5 cm) | 37 (58.7%) | 0 (0%) |
| Splenomegaly (≥15 cm) | 7 (11.1%) | 0 (0%) |
| Bone Marrow Involvement (%) by IHC | 60 | 0 (0%) |
| | (range 3-95) | (range 0-0) |
| MYD88 $^{L265P}$ positive | 55 (89%) | 6 (50%) |

IHC, immunohistochemistry.

Development of Quantitative AS-PCR Assays for CXCRS338X Mutations

Since CXCR4$^{S338X}$ mutation can occur due to C>G and C>A mutations at nucleotide position 1013 in the CXCR4 gene, two AS-PCR assays were developed to permit their detection. Three reverse primers were designed to differentiate the nucleotide positions corresponding to the mutant and wild-type alleles of CXCR4S338X. To optimize the specificity, an internal mismatch in the third position from the 3'-end was introduced. 5'-AGACTCAGACTCAGTGGAAACAGTTC-3' (SEQ ID NO:4) was used to detect the C>G mutation, and 5'-AGACTCAGACTCAGTGGAAACAGGTT-3' (SEQ ID NO:5) was used to detect the C>A mutation. The wild-type specific reverse primer was 5'-AGACTCAGACTCAGTGGAAACAGTTG-3' (SEQ ID NO:6). The common forward primer was 5'-TTCCACTGTTGTCTGAACCCCATC-3' (SEQ ID NO:7). Quantitative detection of the CXCR4$^{S338X}$ mutations was achieved using the above described primers with Power SYBR® Green PCR Master Mix used in accordance with manufacturer's instructions for the ABI Prism 7500 Sequence Detection System (Applied Biosystems, Foster City, Calif.). PCR reaction was performed in a final volume of 25 μl with 25 nM of each primer and 50 ng DNA. Thermal cycling conditions were as follows: 10 min at 950 C, followed by 40 cycles of 950 C for 15 seconds and 600 C for 60 seconds. Each sample was assayed in triplicate. The standard curves for the CXCR4$^{S338X}$ mutations were generated by serial dilution of mutant DNA with wild-type DNA (50%, 10%, 2%, 0.4%, 0.08%, and wild-type). For the corresponding reference PCR, the forward and reverse primers were 5'-ACTACATTGGGATCAGCATCGACTC-3' (SEQ ID NO:8) and 5'-TGAAGACTCAGACTCAGTGGAAACAG-3' (SEQ ID NO:9), respectively. The mutation burden was calculated based on the value of delta CT generated from the standard curves.

Sanger Sequencing of CXCR4 C-Terminal Domain

The C-terminal domain of the CXCR4 gene was sequenced by Sanger sequencing. The forward PCR primer 5'-ATG GGG AGG AGA GTT GTA GGA TTC TAC-3' (SEQ ID NO:10) and reverse PCR primer 5'-TTG GCC ACA GGT CCT GCC TAG ACA-3' (SEQ ID NO:11) were designed to amplify the CRCR4 open reading frame. Amplified PCR products were isolated by QIA quick gel extraction kit (Qiagen, CA) and sequenced using both forward and reverse PCR primers and an additional sequencing primer 5'-GCTGCCTTACTACATTGGGATCAGC-3' (SEQ ID NO:12).

Results
Development of CXCR4$^{S338X\ C>A}$ and CXCR4$^{S338X\ C>G}$ AS-PCR Assays.

Real-time AS-PCR detected the CXCR4$^{S338X\ C>A}$ mutation at a dilution of 0.4% with a 2 cycle difference (cutoff of 9.1) from the wild-type DNA background. Correlation coefficient of the standard curve was 0.992 and demonstrated a slope value of −3.45 (FIG. 1). The melting curve analysis revealed that the CXCR4$^{S338X\ C>G}$ mutant-specific amplicon melted at 81.20 C. For the CXCR4$^{S338X\ C>G}$, real-time AS-PCR detected this variant at a dilution of 0.16% with >2 cycle difference (using a cutoff of 10.5) from the wild-type DNA background. Correlation coefficient of the standard curve was 0.999 with a slope value of −3.74 (FIG. 1). The melting curve analysis revealed that the CXCR4$^{S338X\ C>G}$ mutant-specific amplicon melted at 81.70 C.

CD19-sorted BM and PB samples were first analyzed using the CXCR4$^{S338X\ C>G}$ AS-PCR assay in the same 13 WM patients and 13 healthy donors described above. Healthy donors displayed a median $\Delta C_T$ value of >17.0 cycles, whereas CXCR4$^{S338X\ C>G}$ WM patients had a median $\Delta C_T$ value of 0.8 (range 0.2 to 1.4 cycles) in BM samples and a median $\Delta C_T$ value of 1.6 (range 0.9-1.6 cycles) in PB samples; p<0.001 for BM and PB sample comparisons to healthy donor samples. Among CXCR4$^{WT}$ and CXCR4$^{S338X\ C>A}$ patients, the median $\Delta C_T$ values with this assay were >11.9 cycles and 11.2 (range 11.1 to 11.4 cycles) in BM samples, respectively (p<0.01 for comparisons of both cohorts versus CXCR4$^{S338X\ C>G}$ WM patient BM samples). For PB samples, the median $\Delta C_T$ values for CXCR4$^{WT}$ and CXCR4$^{S338X\ C>A}$ patients were >14.2 cycles; and 11.2 (range 11.1 to 11.4 cycles); p<0.01 for comparisons of both cohorts versus CXCR4$^{S338X\ C>G}$ WM patient BM and PB samples. There were no significant differences in median $\Delta C_T$ values for either CXCR4$^{WT}$ or CXCR4$^{S338X\ C>A}$ patient BM or PB samples versus healthy donors. CXCR4$^{S338X\ C>G}$ was detected in 4/4 (100%) BM and simultaneously collected PB samples of patients bearing this variant by Sanger sequencing. Using a $\Delta C_T$ cutoff of 10.5 representing a >2 cycle difference from the lowest healthy donor cutoff, CXCR4$^{S338X\ C>G}$ was positive in BM and PB samples from all 4 of these patients.

Detection of CXCR4$^{S338X\ C>A}$ and CXCR4$^{S338X\ C>G}$ WHIM Mutations in WM and IgM MGUS Patients by AS-PCR Assays.

Figure 2A:
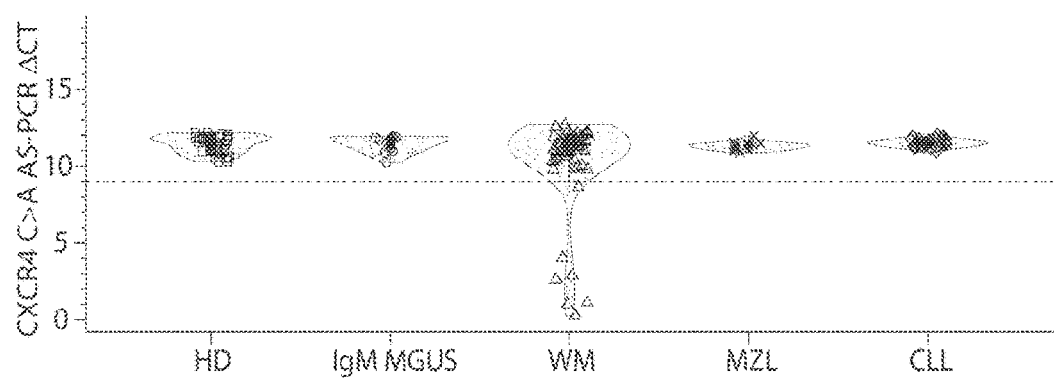
FIG. 2. Real-time AS-PCR results for $CXCR4^{S338X\ C>A}$ or $CXCR4^{S338X\ C>G}$ variants in WM, IgM MGUS, CLL and healthy donor samples. Violin plot representing AS-PCR differences in cycle threshold ($\Delta C_T$) for WM, IgM MGUS, CLL, and healthy donor (HD) samples evaluated for $CXCR4^{S338X\ C>A}$ (FIG. 2A) and $CXCR4^{S338X\ C>G}$ (FIG. 2B) variants. The span of grey area for each cohort represents the kernel density estimation of the sample distribution, and highlights the bimodal nature of the data. Box plots with interquartile ranges are shown in black with an overlay of the individual data points. Samples evaluated were from WM (n=62), IgM MGUS (n=12), MZL (n=18) and CLL (n=32) patients, and health donors (n=32). Gray line denotes Δct cutoffs established for each AS-PCR assay.
Figure 2B:
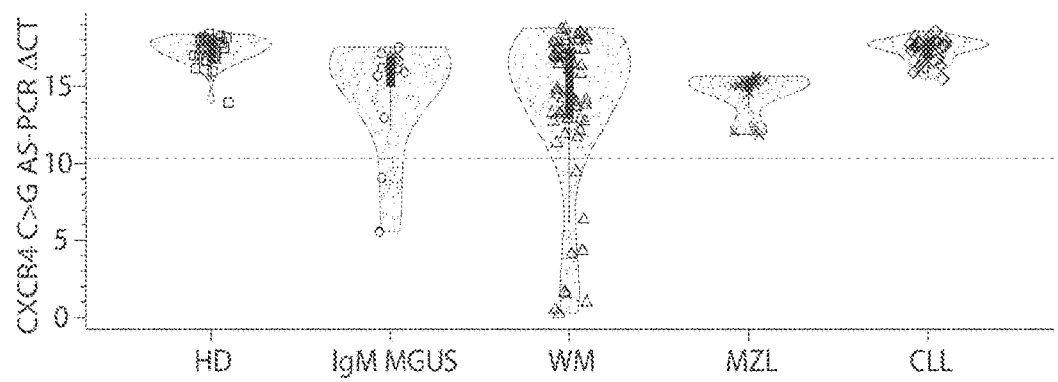

Both CXCR4$^{S338X\ C>A}$ and CXCR4$^{S338X\ C>G}$ assays were then applied using the $\Delta C_T$ cutoffs established above to detect their respective target variants in samples from a separate cohort of 62 WM, 12 IgM MGUS, 18 MZL, and 32 CLL patients, as well as 32 healthy donors. Sanger sequencing of BM CD19-selected samples from these patients revealed CXCR4$^{WHIM}$ mutations that included non-sense or frameshift mutations in 17/62 (27.4%) patients (Table 2). Application of CXCR4$^{S338X\ C>A}$ AS-PCR assay to the BM samples used for Sanger sequencing in the 62 WM patients identified 7 patients with CXCR4$^{S338X\ C>A}$ that included all 5 patients who had this variant by Sanger sequencing, as well as 2 additional patients who were negative by Sanger sequencing (FIG. 2). The CXCR4$^{S338X\ C>A}$ AS-PCR assay did not detect the CXCR4$^{S338X\ C>A}$ variant in the remaining WM patients, including those with frameshift mutations, and other nonsense mutations (inclusive of patients with the CXCR4$^{S338X\ C>G}$ variant). The CXCR4$^{S338X\ C>A}$ AS-PCR assay also did not detect the CXCR4$^{S338X\ C>A}$ variant in samples from the 12 IgM MGUS, 18 MZL, and 32 CLL patients, as well as 32 healthy donors.

TABLE 2

Mutational status by Sanger sequencing for the 62 WM patients evaluated by AS-PCR for CXCR4$^{S338X\ C>A}$ and CXCR4$^{S338X\ C>G}$ variants.

| N= | Mutation Status | Nucleotide change | Amino acid change |
|---|---|---|---|
| 45 | Wild-type | None | None |
| 1 | Frameshift | r.969_971insG | S324fs |
| 2 | Nonsense | r.1000C>T | S334X |
| 2 | Frameshift | r.1012_1014insT | S338fs |
| 5 | Nonsense | r.1013C>A | S338X |
| 7 | Nonsense | r.1013C>G | S338X |

Application of the CXCR4$^{S338X\ C>G}$ AS-PCR assay in BM samples used for Sanger sequencing in the 62 WM patients identified all 7 patients with CXCR4$^{S338X\ C>G}$ with this variant identified by Sanger sequencing, as well as 2 additional patients who were negative by Sanger sequencing (FIG. 2). The CXCR4$^{S338X\ C>G}$ AS-PCR assay did not detect the CXCR4$^{S338X\ C>G}$ variant in the remaining WM patients, including those with frameshift and other nonsense mutations (inclusive of patients with the CXCR4$^{S338X\ C>A}$ variant). The CXCR4$^{S338X\ C>G}$ AS-PCR assay also detected the CXCR4$^{S338X\ C>G}$ variant in BM samples from 2 of 12 (17%) patients with IgM MGUS. All IgM MGUS patients were negative by Sanger sequencing for any CXCR4$^{WHIM}$ mutations. Lastly, samples from 18 MZL and 32 CLL patients, as well as 32 healthy donor samples showed no CXCR4$^{S338X\ C>G}$ variant by the CXCR4$^{S338X\ C>G}$ AS-PCR assay.

Figure 3:
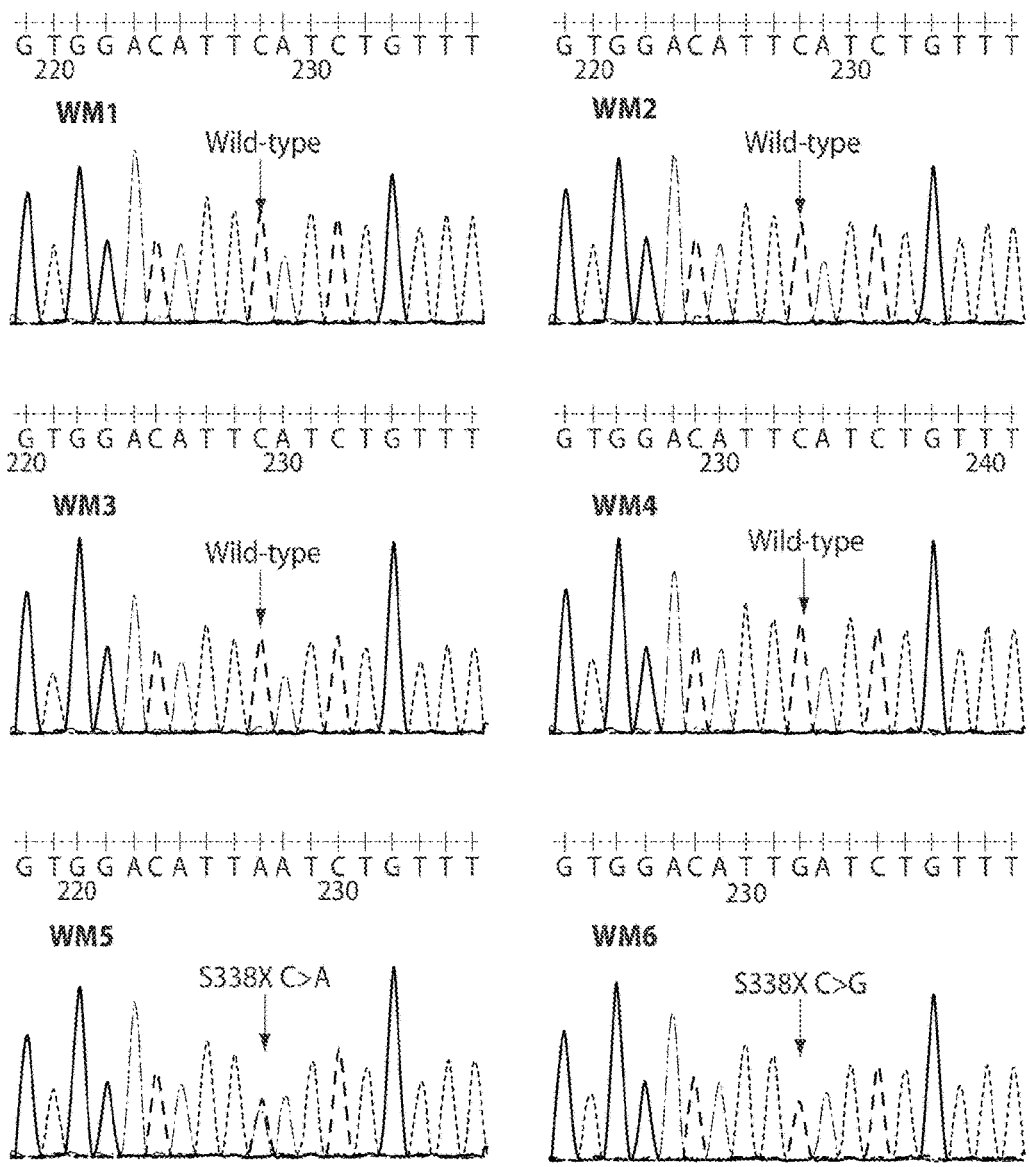
FIG. 3. Sanger tracings for patients with $CXCR4^{WT}$ and who demonstrated $CXCR4^{S338X}$ mutations by AS-PCR assays. Sanger tracings show 4 patients with $CXCR4^{WT}$ who demonstrated $CXCR4^{S338X\ C>A}$ (WM1,2) and $CXCR4^{S338X\ C>G}$ (WM3,4). Sanger tracings for two patients with $CXCR4^{S338X\ C>A}$ (WM5) and CXCR4S338X C>G (WM6) are shown for comparison.

Therefore, the CXCR4$^{S338X}$ AS-PCR assays used in this study validated all 12 CXCR4$^{S338X}$ nonsense mutations detected in this study population by Sanger sequencing, as well as 4 additional WM cases not detected by Sanger sequencing (FIG. 3). In all, 21/62 (34%) WM and 2/12 (17%) patients had CXCR4$^{WHIM}$ mutations by use of Sanger sequencing and/or the AS-PCR assays employed in this study. All 21 WM patients, and both IgM MGUS patients who demonstrated a CXCR4$^{WHIM}$ mutation were also positive for MYD88$^{L265P}$ mutation.

Sanger sequencing of the C-terminal domain of CXCR4 revealed no CXCR4$^{WHIM}$ mutations in any of the 32 CLL patients or 32 healthy donors. However, one of 18 (5%) MZL patients had a CXCR4$^{S344fs}$ frameshift mutation resulting from insertion of T at nucleotide positions 1030_1031. This patient was also wild-type for MYD88. The MYD88 and CXCR4 mutation status for all subjects is shown in Table 3.

TABLE 3

MYD88 and CXCR4 mutation status in patients with WM, IgM MGUS, MZL and CLL patients. CXCR4 mutation status includes all WHIM mutations identified by CXCR4$^{S338X\ C>A}$ and $^{C>G}$ AS-PCR and Sanger sequencing. All WM and IgM MGUS patients with CXCR4$^{WHIM}$ mutations expressed MYD88$^{L265P}$.

|  | (N=) | MYD88 $^{L265P}$ | CXCR4$^{WHIM}$ |
|---|---|---|---|
| Healthy Donors | 32 | 0 (0%) | 0 (0%) |
| Waldenström's Macroglobulinemia | 62 | 57 (89%) | 21 (34%) |
| IgM MGUS | 12 | 6 (60%) | 2 (17%) |
| Marginal Zone Lymphoma | 18 | 2 (11%) | 1 (5%) |
| Chronic Lymphocytic Leukemia | 32 | 1 (3%) | 0 (0%) |

Conclusion

This study describes the development of quantitative AS-PCR assays that detect the most common CXCR4$^{WHIM}$ mutation variant, CXCR4$^{S338X}$ in patients with WM and IgM MGUS. CXCR4$^{WHIM}$ mutations are important determinants to WM disease presentation, including disease tropism, BM disease burden, serum IgM levels, and symptomatic hyperviscosity.[2] Patients with nonsense CXCR4$^{WHIM}$ are particularly more apt to present with aggressive WM disease features, and both frameshift and nonsense CXCR4$^{WHIM}$ patients show muted clinical responses to ibrutinib.[8] Increased resistance to ibrutinib and other WM is also seen by preclinical studies, while the use of CXCR4 antagonists such as plerixafor sensitizes WM cells to the tumoricidal effects of these agents.[6,7] As such, the CXCR4$^{WHIM}$ mutation status plays a role in the diagnostic workup and management of WM patients.

The results of these studies demonstrate high levels of specificity (100%) and sensitivity (100%) for the CXCR4$^{S338X\ C>A}$ and CXCR4$^{S338X\ C>G}$ AS-PCR assays in their respective cohorts, and discriminated samples bearing their target variants from those samples with CXCR4$^{WT}$, CXCR4$^{WHIM}$ frameshift, and other nonsense mutations. Importantly, the AS-PCR assays identified 4 additional patients with CXCR4$^{S338X}$ mutations (2 C>A; and 2 C>G mutations) beyond the 12 CXCR4$^{S338X}$ patients identified by Sanger sequencing in a cohort of 62 WM patients. At baseline, two of these patients (1 C>A; 1 C>G mutations) had minimal BM disease burden (5% and 6%), and it remains possible that these patients has a small tumor load for detection by Sanger sequencing. However, two patients (1 C>A; 1 C>G mutations) had 68% and 80% BM disease involvement by WM. Review of the Sanger tracings for these patients showed absence of detectable mutation in the first patient, while the second patient had minimal changes in the Sanger tracing at nucleotide position 1013. These findings suggest that the CXCR4$^{S338X}$ mutations for these patients may be subclonal.

Additionally, in 2 of 12 IgM MGUS patients, CXCR4$^{S338X}$ (both C>G) was also detectable by AS-PCR assays but absent by Sanger sequencing. It is possible that other CXCR4$^{WHIM}$ mutations may be present in IgM MGUS patients but were below the level of detection by Sanger sequencing. CXCR4$^{WHIM}$ mutations are likely to constitute early genomic events, as has also been proposed for MYD88$^{L265P}$.[12] In this series, both MYD88$^{L265P}$ and CXCR4$^{WHIM}$ mutation status were determined in WM and IgM MGUS patients. Half to 80% of IgM MGUS patients harbor the MYD88$^{L265P}$ somatic mutation, and the presence of MYD88$^{L265P}$ is associated with a higher rate of evolution to malignancy including WM and MZL.[10,13-15] Both IgM MGUS patients with the CXCR4$^{S338X}$ mutation also expressed the MYD88$^{L265P}$ mutation, and co-expression of both CXCR4$^{WHIM}$ and MYD88$^{L265P}$ mutations is nearly universal in WM.[1,2] It is interesting that the one MZL patient with CXCR4$^{S344fs}$ was MYD88$^{WT}$. Similarly, Martinez et al[16] identified a CXCR4$^{R334X}$ nonsense mutation in one of 15 MZL patients, who was also wild-type for MYD88. MYD88$^{L265P}$ is rare in patients with MZL, with estimated frequency of 6-10%.[17,18] Thus, co-expression of CXCR4$^{WHIM}$ and MYD88$^{L265P}$ mutations heralds progression of IgM MGUS toward WM. Additionally, determination of both MYD88 and CXCR4 mutation status helps in further discriminating WM from MZL, and other overlapping B-cell malignancies which often share similar morphological, immunophenotypic, cytogenetic and clinical findings.[19-21]

Interestingly, both AS-PCR assays detected the CXCR4$^{S338X}$ mutation in all PB samples. The use of CD19-selected cells for the AS-PCR assays likely contributed to the high rate of CXCR4$^{S338X}$ detection in PB, as seen with MYD88$^{L265P}$ AS-PCR testing in this patient population. Use of unsorted cells markedly diminished AS-PCR sensitivity.[11] These findings suggest that PB testing may also be feasible for CXCR4$^{S338X}$ mutation testing, thereby providing a convenient and non-invasive means for determination of this variant in WM patients.

Lastly, while CXCR4$^{S338X}$ mutations represent the most common CXCR4$^{WHIM}$ mutations in WM, other somatic mutations in the C-terminal domain are present that are not amenable to detection by the AS-PCR assays described herein. In the proper clinical setting, Sanger sequencing could be considered if the AS-PCR assays are negative.

In summary, the feasibility of using AS-PCR to identify with high specificity and sensitivity CXCR4$^{S338X}$ nonsense mutations in WM and IgM MGUS samples has been demonstrated. AS-PCR identified CXCR4$^{S338X}$ mutations in patients not detectable by Sanger sequencing. Determination of both CXCR4 and MYD88 mutation status distinguishes WM from MZL and CLL. Expression of CXCR4$^{S338X}$ in IgM MGUS cases supports an early oncogenic role for this mutation in WM pathogenesis.

Example 5: The WHIM-Like CXCR4S338X Somatic Mutation Activates AKT and ERK, and Promotes Resistance to Ibrutinib and Other Agents Used in the Treatment of Waldenstrom's Macroglobulinemia Methods CXCR4$^{WT}$ and CXCR4$^{S338X}$ cDNAs were subcloned into plenti-IRES-GFP vector, and transduced using an optimized lentiviral based strategy into BCWM.1 and MWCL-1 WM cells. Five days after transduction, GFP positive cells were sorted and used for functional studies. Surface expression of CXCR4 was determined by flow cytometric analysis using a PE-conjugated anti-CXCR4 monoclonal antibody (BD Biosciences, San Jose Calif.). Transduced cell lines were stimulated with or without SDF-1a (10-100 nM), and cell surface expression of CXCR4 determined on CXCR4$^{WT\ and\ S338X}$ transduced cells. CXCR4 expression levels were calculated as: [(receptor geometric mean fluorescence intensity [MFI] of treated cells-MFI of isotype IgG control)/(receptor geometric MFI of unstimulated cells-MFI of isotype IgG control)]×100. For phosphoflow experiments, cells were fixed with BD Phosflow Fix Buffer1 at the indicated time point at 37° c. for 10 minutes followed by two washes with 1× perm/wash buffer I. FACS analysis was performed using conjugated antibodies to phospho-ERK1/2 (T$^{202}$/Y$^{204}$), phospho-AKT(S$^{473}$) (BD Phosflow), and phospho-BTK (Y$^{223}$) (BD Pharmigen, San Jose Calif.). Results were confirmed by immunoblotting. Cell signaling and survival studies related to CXCR4 signaling were performed in the presence or absence of SDF-1a (20 nM) (R&D Systems, Minneapolis Min.), ibrutinib (0.5 uM), bendamustine (5-10 uM), fludarabine (3 uM), bortezomib (5 nM), idelalisib (0.5 uM) (MedChem Express, Monmouth, N.J.), the CXCR4 inhibitor AMD3100 (30 uM), and pertussis toxin (500 ng), a G-protein coupled receptor (GPCR) antagonist that blocks CXCR4 signaling (Sigma-Aldrich, St. Louis Mo.). Cell signaling and survival studies related to AKT and ERK were performed in CXCR4$^{S338X}$ expressing cells as described above, in the presence or absence of either AKT (MK-2206, 0.5 uM and AZD-5363, 0.5 uM) or MEK (AS-703026, 0.25 uM; AZD-6244, 0.5 uM and U0126, 5.0 uM) specific inhibitors at their IC$_{50}$ dose (Selleck Chemicals, Houston Tex.). For survival studies, WM cells were incubated for 6 hours and apoptosis assessed by immunoblotting using antibodies for cleaved PARP and cleaved caspase 3 (Abcam, Cambridge Mass.), and also by Annexin V staining (R&D Systems) in the presence of low dose (0.5 uM) BCL-2 inhibitor (GDC-0199; Selleck Chemicals Inc., Houston Tex.) to optimize ibrutinib related apoptotic effects in SDF-1a rescue experiments. Bone marrow core biopsies from WM patients whose aspirates were used to sort for CD19$^+$ cells and Sanger sequencing for the C-terminal domain were stained for phospho-AKT and phospho-ERK (Cell Signaling Technologies, Danvers Mass.) before and after ibrutinib therapy.

Results

Figure 4A:
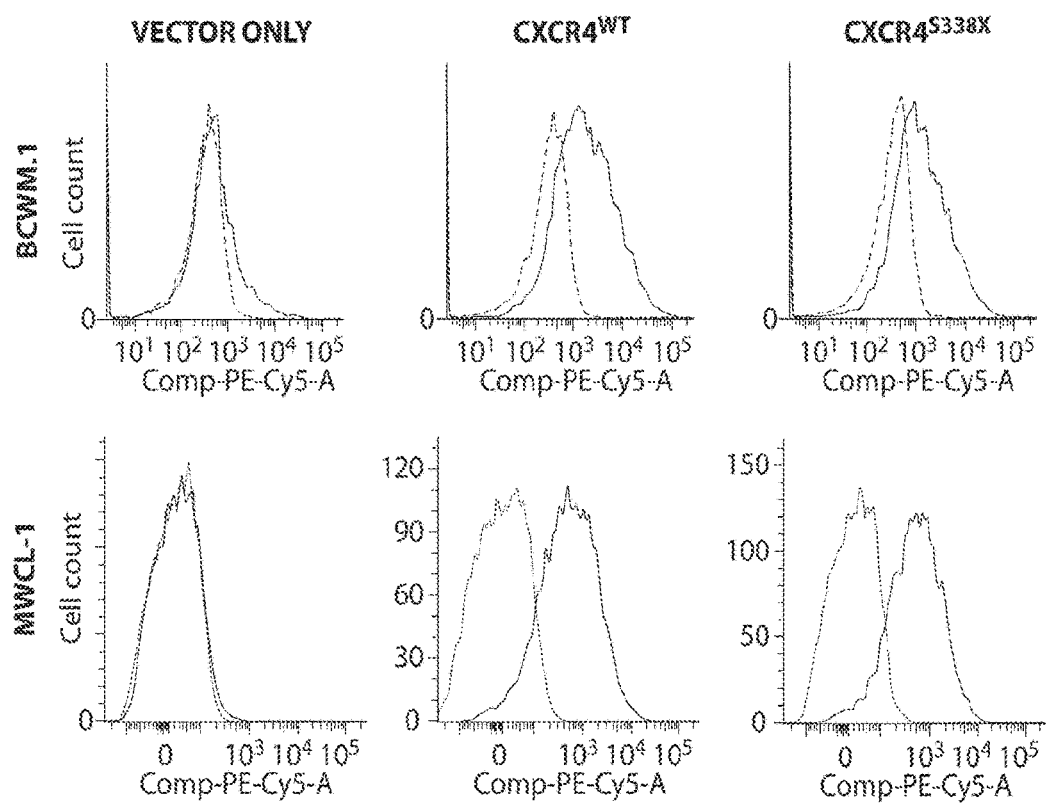
(FIG. 4A) Cell surface expression of CXCR4 in vector only, $CXCR4^{WT}$ and $CXCR4^{S338X}$ engineered BCWM.1 and MWCL-1 cells by flow cytometry using PE-Cy5 conjugated anti-CXCR4 mAb (12G5) (dark line) or isotype control (gray line).
Figure 4B:
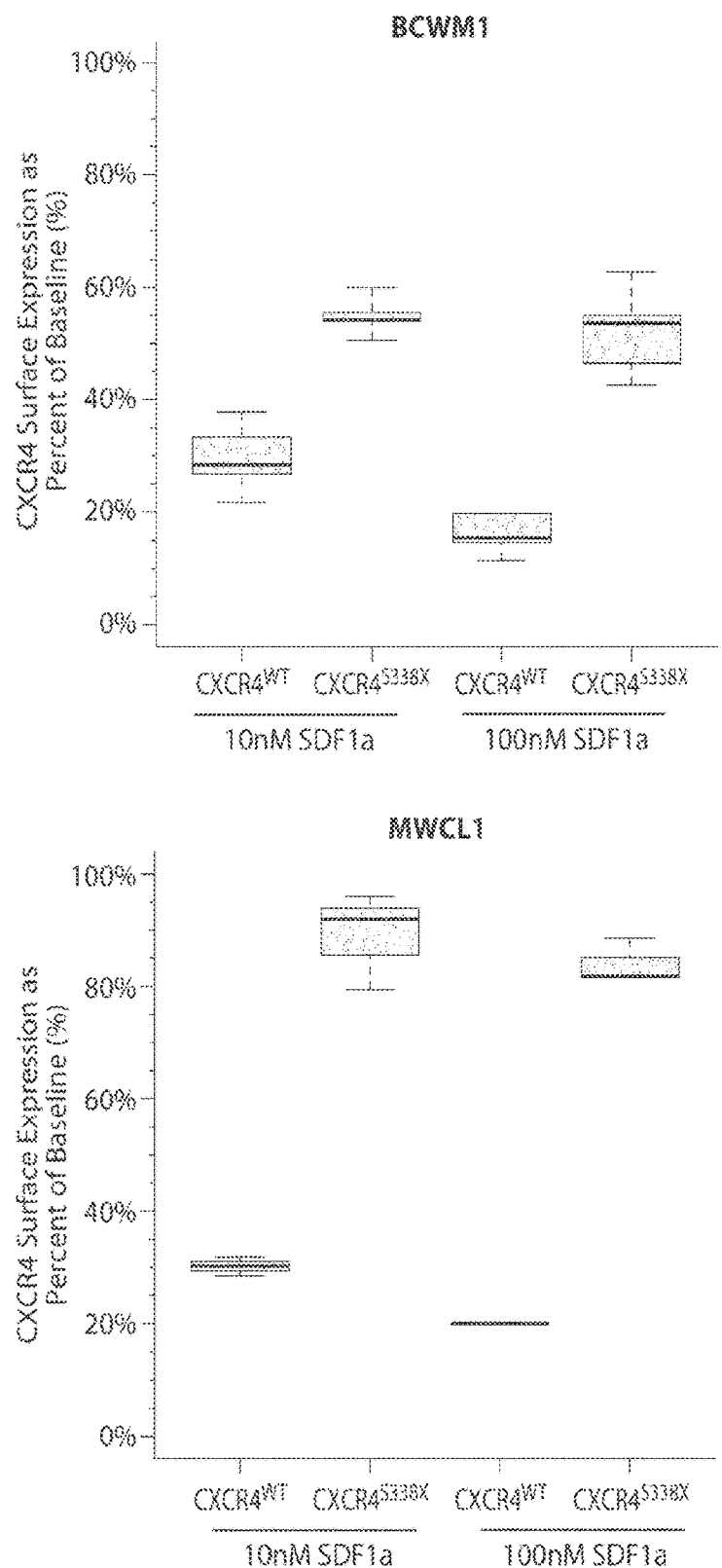
Figure 5A:
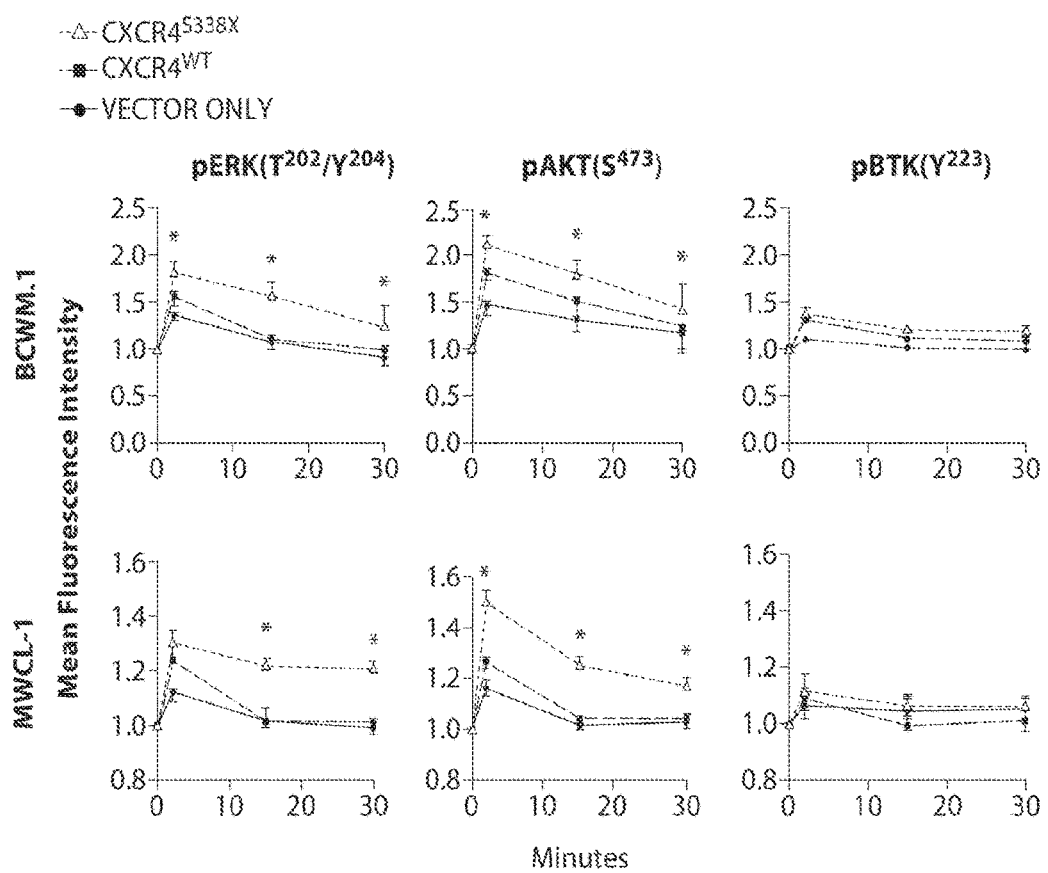
(FIG. 5A) plenti-GFP vector, $CXCR4^{WT}$ and $CXCR4^{S338X}$ expressing WM cells were treated with SDF-1a (20 nM) for 2, 15, and 30 minutes and phosphoflow analyses performed using conjugated anti-phospho-ERK ($T^{202}/Y^{204}$), phospho-AKT ($S^{473}$) and phospho-BTK($Y^{223}$) antibodies. Data represent the mean of at least 3 experiments±SEM; *p<0.05 for CXCR4$^{S338X}$ versus CXCR4$^{WT}$.
Figure 5B:
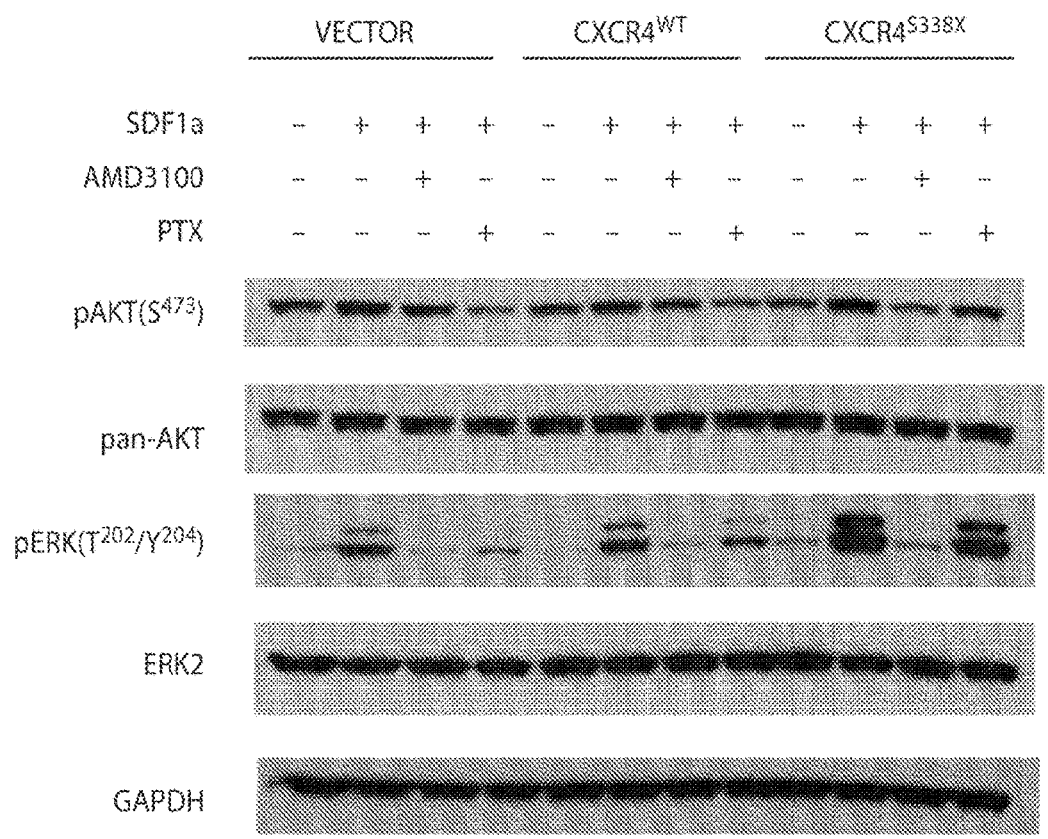
(FIG. 5B) Immunoblotting studies depicting differences in phospho-ERK (T$^{202}$/Y$^{204}$), total ERK, phospho-AKT (S$^{473}$), total AKT in plenty-GFP vector only, CXCR4$^{WT}$ and CXCR4$^{S338X}$ expressing BCWM.1 cells stimulated for 2 minutes with SDF-1a (20 nM) after either no pre-treatment, or pre-treatment for 2 hours with AMD3100 (30 uM) or pertussis toxin (500 ng; PTX). Membranes were stripped following pERK and pAKT staining, and were then probed for total ERK and AKT as shown.

Non-transfected BCWM.1 and MWCL-1 cells express very low levels of CXCR4. These cell lines were therefore transfected with plenti-IRES-GFP vector alone, CXCR4$^{WT}$ or CXCR4$^{S338X}$ WHIM-like protein expressing vectors. Flow cytometric analysis confirmed expression, as well as similar levels of cell surface CXCR4 expression for CXCR4$^{WT}$ and CXCR4$^{S338X}$ engineered WM cells (FIG. 4A). Stimulation of transfected WM cells with the ligand for CXCR4 (SDF-1a) for 30 minutes resulted in significantly greater down-regulation of cell surface CXCR4 expression on CXCR4$^{WT}$ versus CXCR4$^{S338X}$ expressing WM cells (p<0.001; FIG. 4B). Because AKT, ERK and possibly BTK are known downstream signal mediators of CXCR4, their signaling was interrogated by phosphoflow and immunoblotting. WM cells were stimulated with SDF-1a for 2, 15, and 30 minutes and evaluated by phosphoflow analysis. Stimulation with SDF-1a resulted in enhanced and prolonged AKT and ERK activation in CXCR4$^{S338X}$ versus GFP vector only and CXCR4$^{WT}$ expressing BCWM.1 and MWCL-1 WM cells (FIG. 5A). In contrast, only minimal changes in BTK activation were observed between vector only, CXCR4$^{WT}$, and CXCR4$^{S338X}$ expressing cells stimulated with SDF-1a using phosphoflow analysis. Immunoblotting after 30 minutes of SDF-1a stimulation confirmed enhanced AKT and ERK phosphorylation in CXCR4$^{S338X}$ BCWM.1 cells relative to vector only, and CXCR4$^{WT}$ cells (FIG. 5B). Total AKT and ERK protein levels remained the same in vector only, CXCR4$^{WT}$ and CXCR4$^{S338X}$ expressing BCWM.1 cells following SDF-1a stimulation in these studies, denoting that activation of AKT and ERK occurred in the absence of changes in total protein expression for these transcription factors (FIG. 5B). Importantly, both AMD3100 and pertussis toxin blocked both AKT and ERK activation confirming their SDF-1a triggered transactivation via GPCR/CXCR4 signaling in both CXCR4$^{WT}$ and CXCR4$^{S338X}$ expressing BCWM.1 cells (FIG. 5B).

Figure 6:
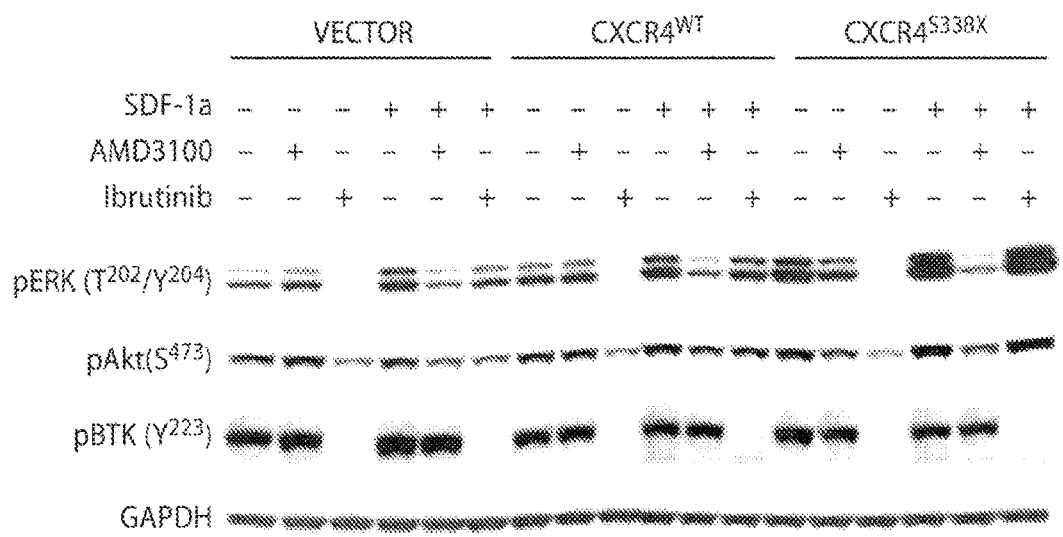
FIG. 6. Impact of ibrutinib on phospho-AKT, ERK and BTK expression following SDF-1a stimulation of plenti-GFP vector, CXCR4$^{WT}$ and CXCR4$^{S338X}$ expressing BCWM.1 cells. plenti-GFP vector, CXCR4$^{WT}$ and CXCR4$^{S338X}$ expressing BCWM.1 cells were pretreated for 2 hours with either ibrutinib (0.5 uM) or AMD3100 (30 uM) prior to stimulation with SDF-1a (20 nM) for 2 minutes. Results depict differences in phospho-AKT, phospho-ERK, and phospho-BTK obtained by immunoblotting following SDF-1a stimulation in the absence or presence of ibrutinib (0.5 uM).

Because AKT, ERK and BTK signaling are impacted by ibrutinib, CXCR4$^{WT}$ and CXCR4$^{S338X}$ expressing WM cells were cultured in the presence or absence of SDF-1a and/or ibrutinib. Cell surface expression of CXCR4 was examined in transfected WM cells following ibrutinib treatment at 0.5, 1, 2, and 6 hours and observed little or no significant changes in cell surface CXCR4 expression in either CXCR4$^{WT}$ or CXCR4$^{S338X}$ expressing WM cells (data not shown). Furthermore, addition of ibrutinib did not affect SDF-1a related changes in cell surface CXCR4 expression in vector only, CXCR4$^{WT}$ and CXCR4$^{S338X}$ transfected WM cells (data not shown). The impact of SDF-1a triggered AKT, ERK and BTK signaling following ibrutinib treatment was examined in CXCR4$^{WT}$ and CXCR4$^{S338X}$ BCWM. 1 cells. Ibrutinib attenuated SDF-1a triggered AKT and ERK activation in plenti-GFP vector only and CXCR4$^{WT}$ expressing WM cells, whereas in CXCR4$^{S338X}$ expressing WM cells both AKT and ERK signaling remained robust and did not show attenuation in the presence of ibrutinib (FIG. 6). Conversely, in both SDF-1a treated CXCR4$^{WT}$ and CXCR4$^{S338X}$ expressing WM cells, ibrutinib blocked BTK signaling (FIG. 6). These studies therefore show that SDF-1a triggered AKT and ERK, but not BTK activation despite treatment with ibrutinib in CXCR4$^{S338X}$ expressing BCWM.1 cells.

Figure 7A:
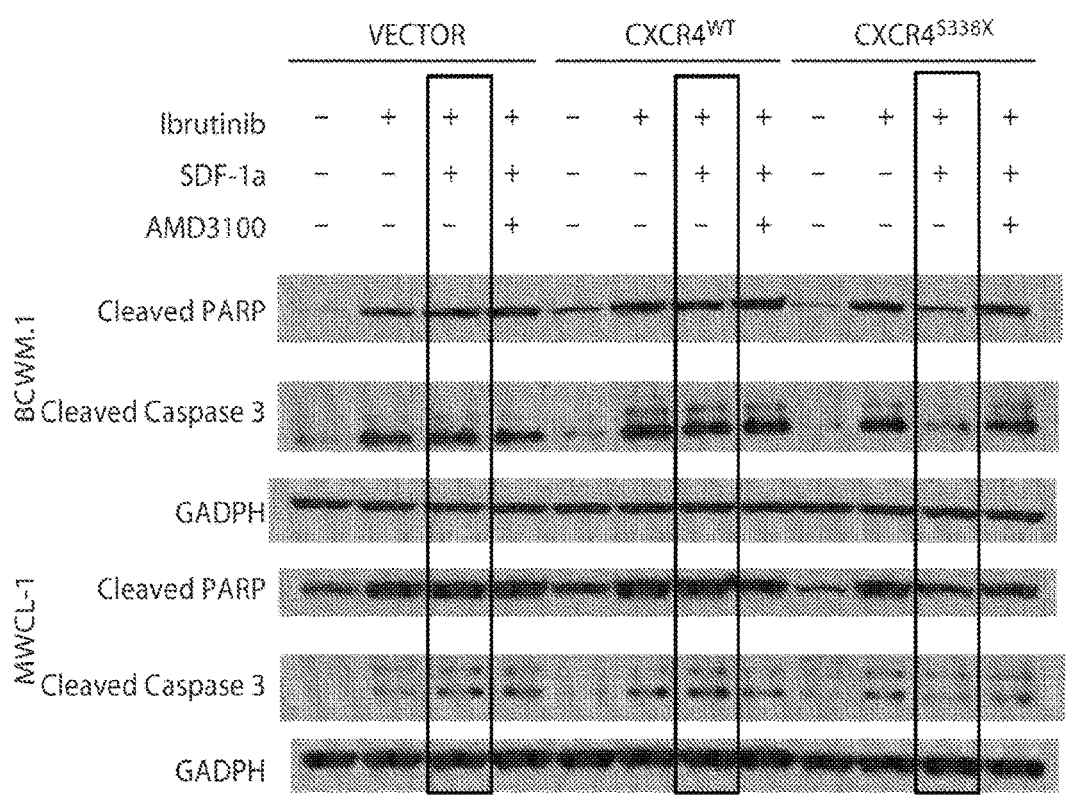
(FIG. 7A). Annexin V staining of wild-type and CXCR4$^{S338X}$ expressing BCWM.1 and MWCL-1 cells following treatment with DMSO vehicle control (shaded curve), ibrutinib (IB), ibrutinib plus SDF-1a (IB/SDF-1a), or ibrutinib plus SDF-1a and the CXCR4 inhibitor AMD3100 (IB/SDF-1a/AMD) at 18 hours (non-shaded curves). Percentages shown denote treatment related Annexin V staining (outside of DMSO vehicle control). Study was performed in triplicate, and results from a representative study set are shown (FIG. 7B).
Figure 7B:
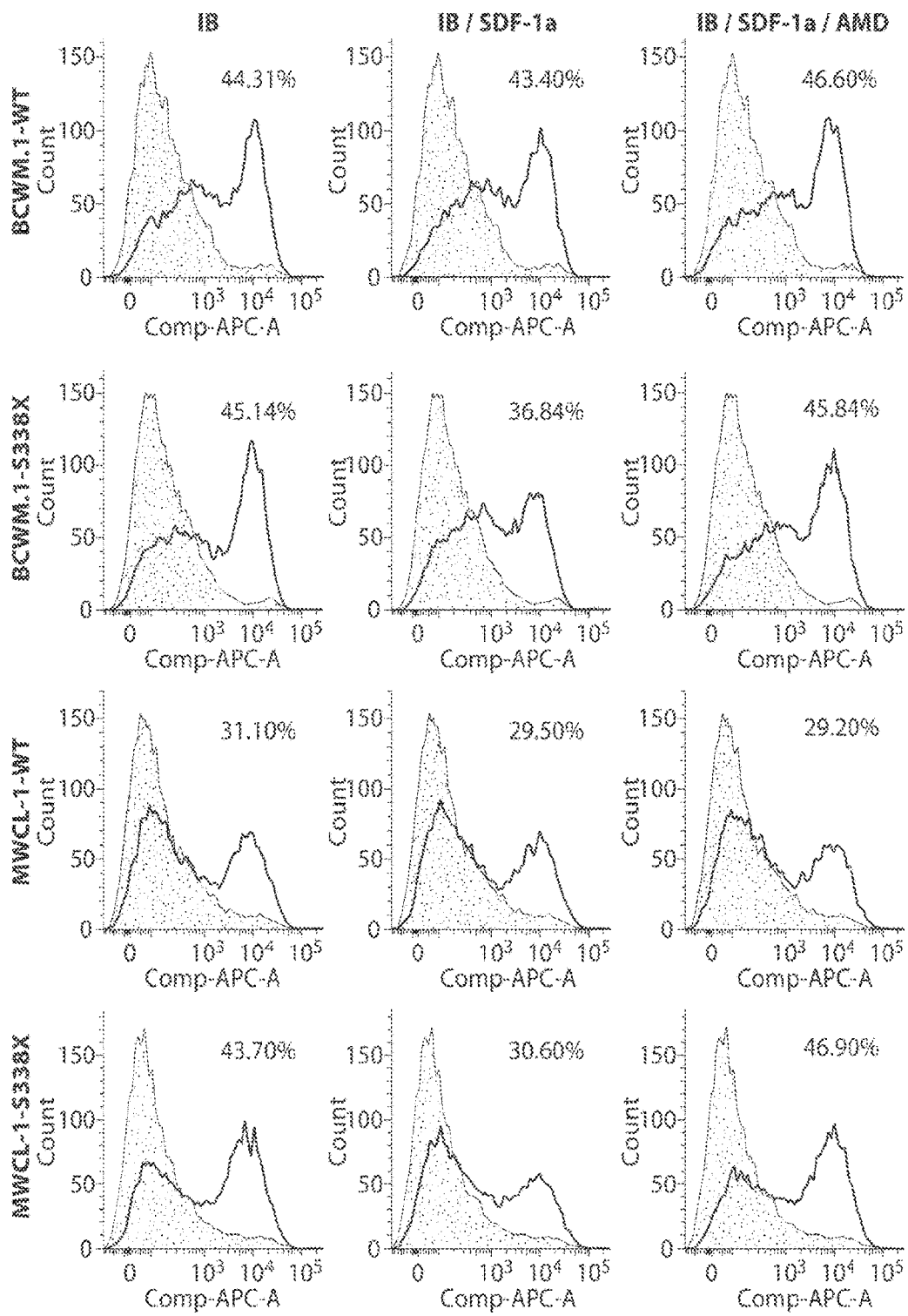
FIG. 7. CXCR4$^{S338X}$ expressing BCWM.1 and MWCL-1 cells show resistance to ibrutinib induced PARP and caspase 3 cleavage in the presence of SDF-1a and reversed by AMD3100. plenti-GFP vector, CXCR4$^{WT}$ and CXCR4$^{S338X}$ expressing WM cells were treated for 6 hours with ibrutinib (0.5 uM) in the presence or absence of SDF-1a (20 nM) and/or the CXCR4 receptor antagonist AMD3100 (30 uM). PARP and caspase 3 cleavage was assessed by immunoblotting at 6 hours.

To clarify if the expression of the CXCR4$^{S338X}$ mutant protein conferred enhanced survival against ibrutinib, SDF-1a treated vector only, CXCR4$^{WT}$, and CXCR4$^{S338X}$ expressing BCWM.1 and MWCL-1 cells were cultured in the presence or absence of ibrutinib (0.5 uM) and/or AMD3100 for 6 hours. Apoptotic changes were assessed by evaluating for cleaved PARP (a caspase 3 substrate) and cleaved caspase 3 given prior studies establishing caspase mediated killing for ibrutinib. As shown in FIG. 7, treatment with ibrutinib for 6 hours led to increased PARP and caspase 3 cleavage in vector only, CXCR4$^{WT}$, and CXCR4$^{S338X}$ expressing BCWM.1 and MWCL-1 cells. Co-culture with SDF-1a failed to protect plenti-GFP vector only and CXCR4$^{WT}$ expressing cells from ibrutinib induced PARP and caspase 3 cleavage. Conversely, SDF-1a rescued CXCR4$^{S338X}$ expressing WM cells from ibrutinib induced apoptosis, a finding which could be reversed by co-treatment of CXCR4$^{S338X}$ expressing BCWM.1 and MWCL-1 cells with both ibrutinib and the CXCR4 receptor antagonist AMD3100 (FIG. 7). Annexin V staining confirmed rescue of ibrutinib mediated apoptotic changes by SDF-1a, as well as restoration of apoptotic changes by addition of AMD3100 to BCWM.1 and MWCL-1 cells treated with ibrutinib and SDF-1a (FIG. 7).

Figure 8A:
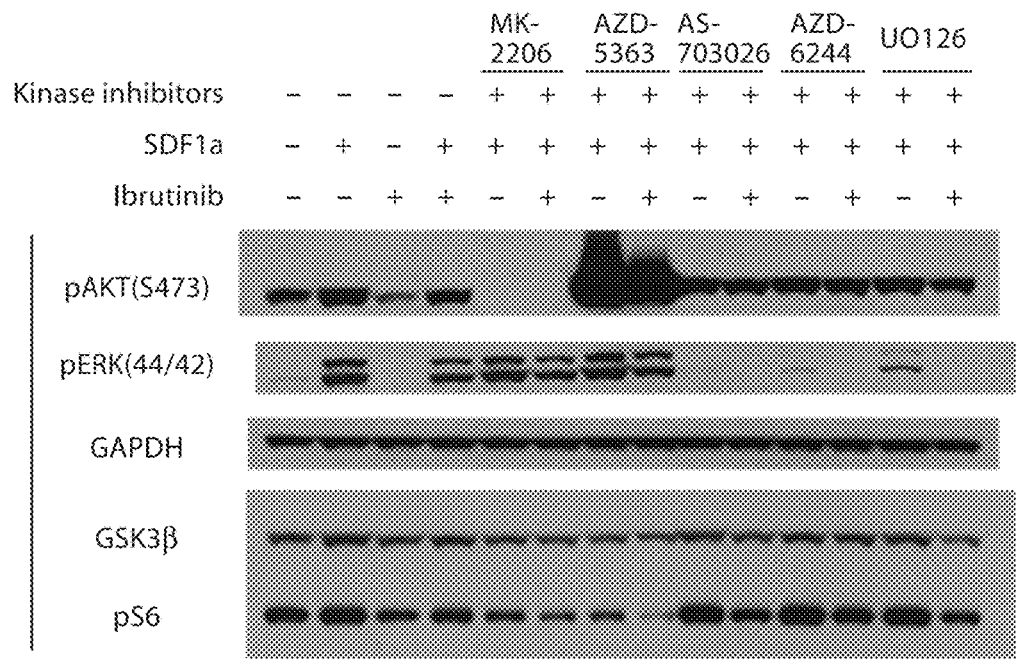
(FIG. 8A) Immunoblotting results for phospho-AKT (S$^{473}$) and phospho-ERK (T$^{202}$/Y$^{204}$) in CXCR4$^{S338X}$ expressing BCWM.1 cells pretreated with ibrutinib with and without AKT or ERK inhibitors, then subjected to SDF-1a stimulation for 2 minutes. The inhibitory effect of AZD-5363 on AKT, which is known to paradoxically hyper-phosphorylate pAKT(S$^{473}$) was confirmed by inhibition of the phospho-activity for the downstream AKT targets GKS3β and pS6.
Figure 8B:
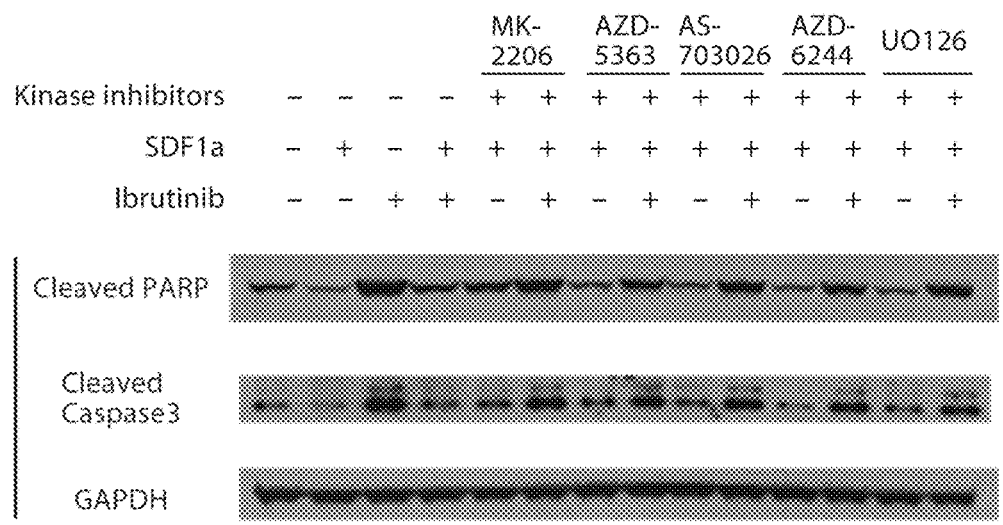
(FIG. 8B) Immunoblotting results for cleaved PARP and cleaved caspase 3 in CXCR4$^{S338S}$ expressing BCWM.1 cells treated with ibrutinib and/or AKT or ERK inhibitors for 6 hours at IC$_{50}$ doses.

Since AKT and ERK, but not BTK show continued SDF-1a triggered activation in CXCR4$^{S338X}$ expressing WM cells treated with ibrutinib, the inventors sought to determine if AKT and ERK contributed to the enhanced survival of these cells. SDF-1a cultured CXCR4$^{S338X}$ BCWM.1 cells were treated with either AKT (MK-2206 and AZD-5363) or MEK (AS-703026, AZD-6244 and U0126) specific inhibitors with and without ibrutinib (0.5 uM) for 6 hours so as to clarify the contribution of AKT and ERK to ibrutinib resistance. The inhibitory activity of MK-2206, as well as AS-703026, AZD-6244 and U0126 was confirmed by western blot analysis for pAKT (S$^{473}$) and pERK (T$^{202}$/Y$^{204}$), respectively (FIG. 8). The inhibitory effect of AZD-5363 on AKT, which is known to paradoxically hyper-phosphorylate pAKT(S$^{473}$) was confirmed by inhibition of the phospho-activity for the downstream AKT targets GKS3β and pS6 (FIG. 8). As before, SDF-1a blocked ibrutinib triggered PARP and caspase 3 cleavage in CXCR4$^{S338X}$ expressing BCWM.1 cells. Conversely, addition of either AKT or ERK inhibitors to ibrutinib resulted in augmented PARP and caspase 3 cleavage versus ibrutinib alone in SDF-1a cultured CXCR4$^{S338X}$ BCWM.1 cells (FIG. 8).

Figure 9:
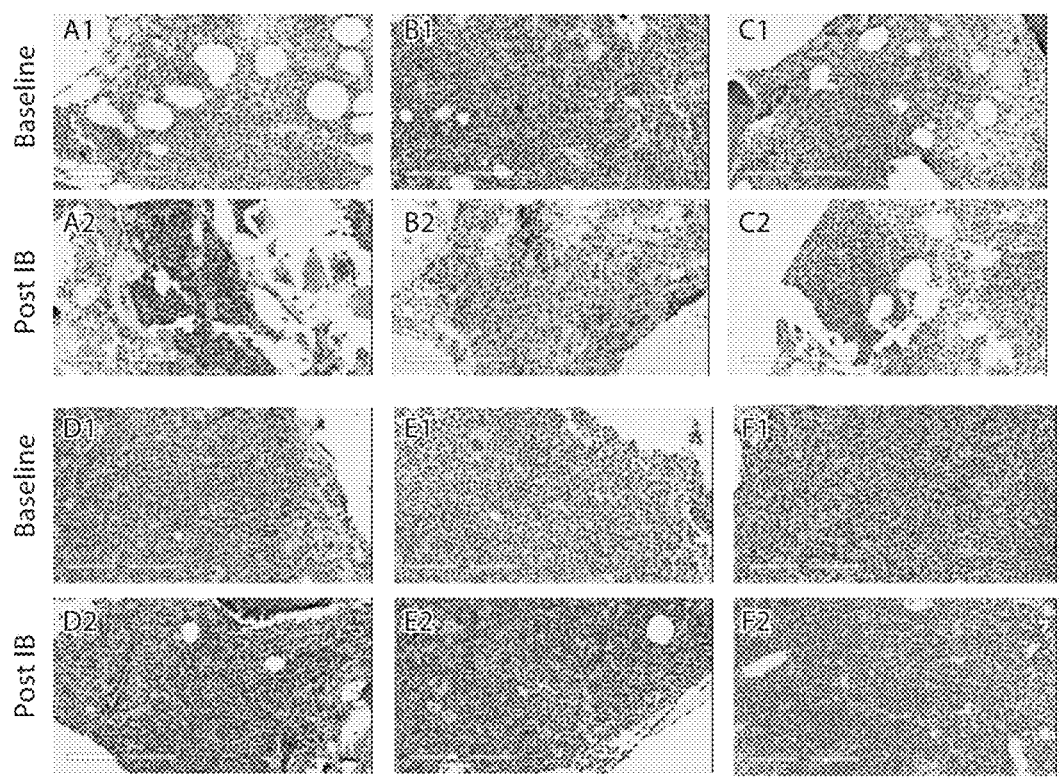
FIG. 9. Immunohistochemical staining for pAKT in bone marrow samples from genotyped WM patients with CXCR4$^{WT}$ and CXCR4$^{WHIM}$ expression. Bone marrow specimens from 3 patients with CXCR4$^{WHIM}$ (FIG. 9A, 9B, 9C) and 3 patients with CXCR4$^{WT}$ (FIG. 9D, 9E, 9F) were stained for pAKT at baseline, and following 6 months of continuous ibrutinib therapy. For the depicted CXCR4$^{WHIM}$ patients, Sanger sequencing showed nonsense mutations for patient A (CXCR4$^{R334X}$) and B (CXCR4$^{S338X}$), and a frameshift (FS) mutation resulting in insertion of T at position 1013 for patient C (CXCR4$^{S338FS}$).

Since pAKT and pERK are enhanced in SDF-1a stimulated CXCR4$^{S338X}$ versus CXCR4$^{WT}$ WM cells, the inventors sought to determine if these transcription factors were differentially activated in samples from WM patients with and without CXCR4$^{WHIM}$ mutations. Bone marrow samples from 6 patients (3 CXCR4$^{WT}$; 3 CXCR4$^{WHIM}$) with relapsed/refractory disease who underwent daily ibrutinib therapy as previously described by us were selected for these studies. As shown in FIG. 9, robust immunohistochemical staining for pAKT was present at baseline in bone marrow tumor samples from CXCR4$^{WHIM}$ patients, whereas by comparison marginal staining for pAKT was present in CXCR4$^{WT}$ patients. pERK staining was present at low levels in both CXCR4$^{WT}$ and CXCR4$^{WHIM}$ patients, without any discernible differences (data not shown). Importantly, in CXCR4$^{WHIM}$ patients, pAKT staining remained robust without any changes from baseline despite these patients being on continuous ibrutinib therapy for 6 months. In contrast, CXCR4$^{WT}$ patients on continuous ibrutinib therapy showed marginal pAKT staining relative to CXCR4$^{WHIM}$ patients. As before, low levels of pERK staining were present despite ibrutinib therapy in all patients, regardless of CXCR4 mutation status (data not shown).

Figure 10A:
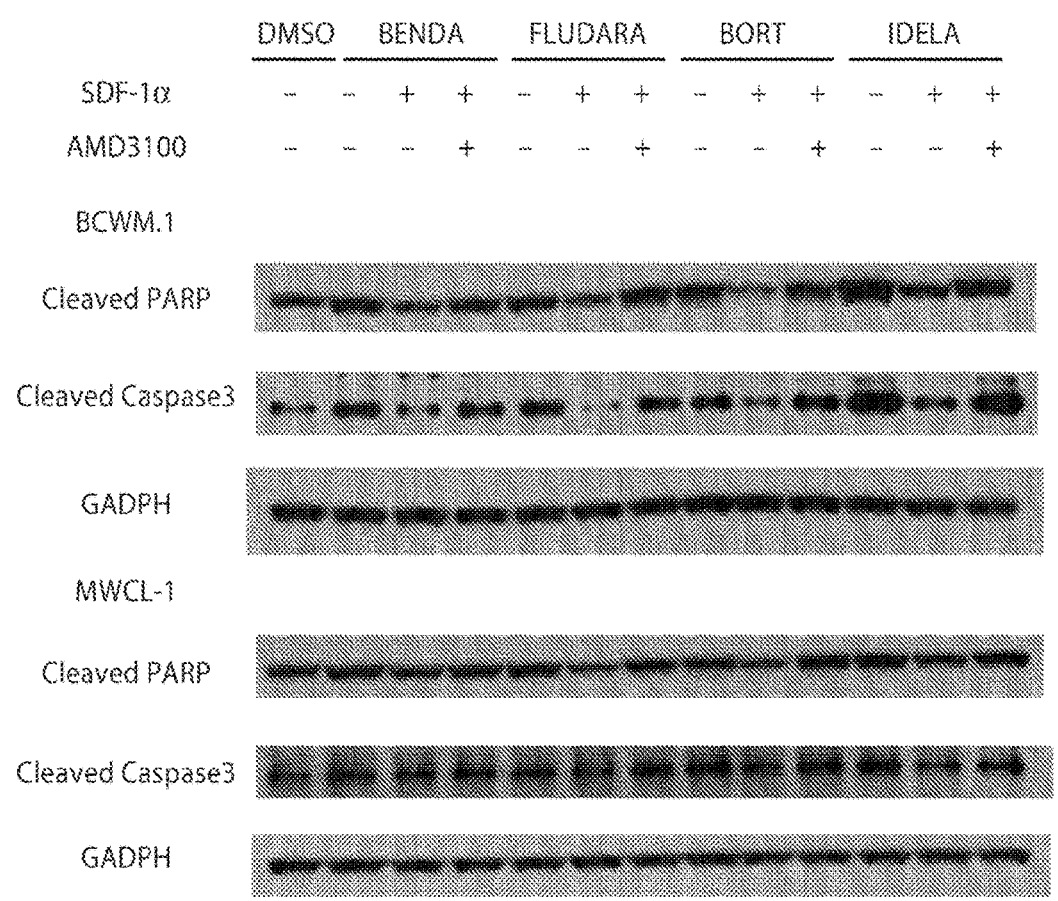
FIG. 10. CXCR4$^{S338X}$ expressing BCWM.1 and MWCL-1 cells show variable resistance to PARP and caspase 3 cleavage mediated by WM relevant therapeutics in the presence of SDF-1a, and reversed by AMD3100. plenti-GFP vector, CXCR4$^{WT}$ and CXCR4$^{S338X}$ expressing WM cells were treated for 6 hours with bendamustine (BENDA), fludarabine (FLUDARA), bortezomib (BORT), and idelalisib (IDELA) at their EC$_{50}$ doses in the presence or absence of SDF-1a (20 nM) and/or the CXCR4 receptor antagonist AMD3100 (30 uM). PARP and caspase 3 cleavage was assessed by immunoblotting at 6 hours (FIG. 10A). Annexin V staining of CXCR4$^{S338X}$ expressing BCWM.1 and MWCL-1 cells following treatment with DMSO vehicle control (shaded curve), idelalisib (ID), idelalisib plus SDF-1a (ID/SDF-1a), or idelalisib plus SDF-1a and the CXCR4 inhibitor AMD3100 (ID/SDF-1a/AMD) at 18 hours (non-shaded curves). Percentages shown denote treatment related Annexin V staining (outside of DMSO vehicle control). Study was performed in triplicate, and results from a representative study set are shown (FIG. 10B).
Figure 10B:
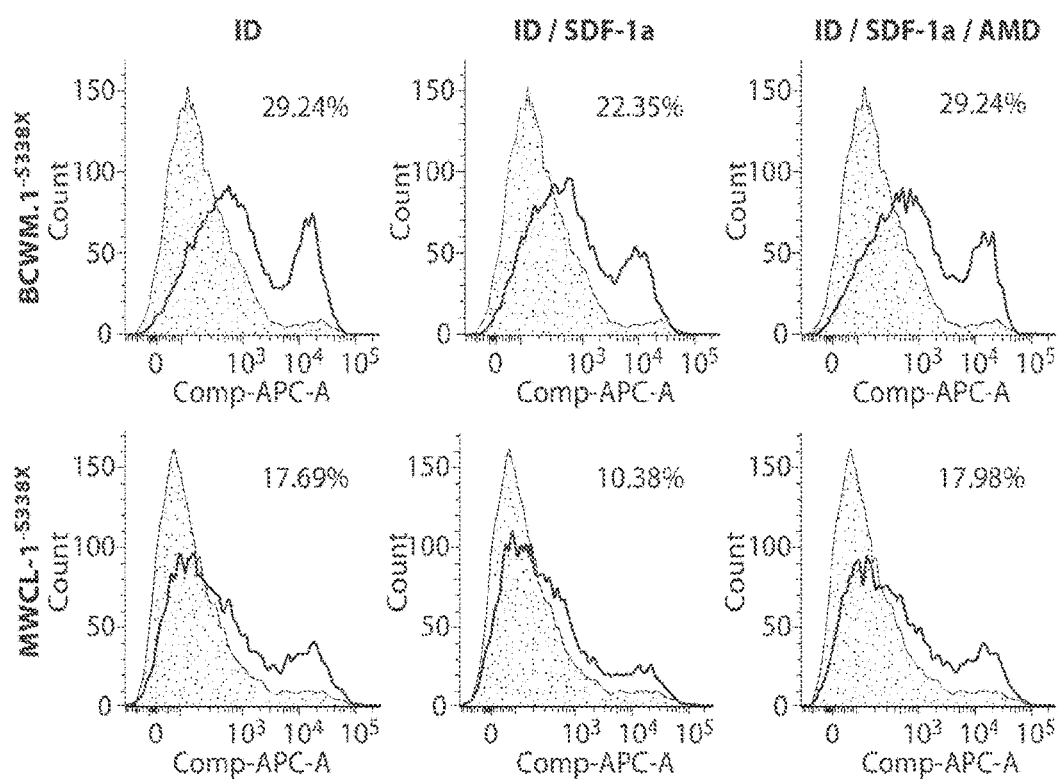

Given the protective effect of SDF-1a against ibrutinib in CXCR4$^{S338X}$ BCWM.1 and MWCL-1 cells, the inventors next sought to clarify if SDF-1a protected against apoptosis triggered by other WM relevant therapeutics (FIG. 10). Treatment of CXCR4$^{S338X}$ BCWM.1 and MWCL-1 cells with bendamustine, fludarabine, bortezomib or idelalisib at their EC$_{50}$ dose ranges resulted in changes in PARP and caspase 3 cleavage at 6 hours which varied based on treatment and WM cell type. CXCR4$^{S338X}$ BCWM.1 cells exhibited moderate levels of SDF-1a mediated rescue for bendamustine, fludarabine and bortezomib, and strong SDF-1a mediated rescue for idelalisib, with reversal of rescue mediated by co-treatment of cells with AMD3100 for all agents. CXCR4$^{S338X}$ MWCL-1 cells displayed a moderate level of rescue effect by SDF-1a for idelalisib, followed by lesser levels of rescue for fludarabine and bortezomib, with reversal of SDF1-a rescue mediated by co-treatment with AMD3100. Conversely, little to no SDF-1a rescue was observed in bendamustine treated CXCR4$^{S338X}$ MWCL-1 cells (FIG. 10). Idelalisib which targets PI3Kδ, a key modulator of AKT activation that supports WM cell survival, showed pronounced rescue by SDF-1a and reversal of rescue by AMD3100 for Annexin V studies as well in both CXCR4$^{S338X}$ BCWM.1 and MWCL-1 WM cells (FIG. 10).

Conclusion

The functional significance of WHIM-like mutations in CXCR4 that are present in up to 30 percent of WM patients, and represent the first reporting of CXCR4 somatic mutations in cancer was determined. These studies demonstrate that the most common WHIM-like mutation (CXCR4$^{S338X}$) identified in WM patients conferred decreased receptor down-regulation, as well as enhanced and sustained AKT and ERK, but not BTK activation following SDF-1a. BTK activation following SDF-1a has been reported in myeloma cells, which show variable levels of BTK activation. Conversely, BTK is activated by MYD88 L265P, and high levels of activated BTK are present in WM cell lines which may have accounted for the minimal changes in phospho-BTK observed in response to SDF-1a stimulation.

Both AKT and ERK are activated in WM cells, and inhibition of their activity leads to apoptotic changes thereby invoking a growth promoting role for their activation in WM. The findings herein provide a putative mechanism for activation of both AKT and ERK by SDF-1a in WM through acquisition of a somatic WHIM-like (CXCR4$^{S338X}$) mutation. Enhanced AKT and ERK signaling in response to SDF-1a has also been observed in response to another WHIM-like (CXCR4$^{R334X}$) mutation which like CXCR4$^{S338X}$ leads to truncation of the regulatory c-terminal domain of CXCR4 (McDermott D H, et al. J Cell Mol Med 2011; 15(10):2071-81).

In these studies with CXCR4$^{S338X}$, as well as those by McDermott et al. who investigated CXCR4$^{R334X}$ related signaling, use of the CXCR4 antagonist AMD3100 blocked SDF-1a triggered AKT and ERK activation. The use of CXCR4 antagonists therefore offers a targeted approach to therapy of WM patients with WHIM-like somatic mutations, particularly given their success in patients with WHIM syndrome patients who harbor germline CXCR4 mutations (McDermott D H, et al. Blood 2011; 118(18):4957-62). Several antagonists to CXCR4 have been developed. AMD3100 is approved for use in stem cell mobilization, while other CXCR4 antagonists such as BMS-936564, AMD-070, TG-0054 and others are in clinical trials. While most cases of WM do not have CXCR4 somatic mutations, aberrant CXCR4 signaling may still exist due to either other CXCR4 path mutations as has been proposed for some WHIM-syndrome cases.

The central finding of these studies was that the CXCR4$^{S338X}$ WHIM-like mutation conferred resistance to ibrutinib triggered apoptosis in WM cells, a finding that was associated with persistent AKT and ERK activation. The association of CXCR4 WHIM-like mutations in patients undergoing ibrutinib therapy was examined. These studies showed that the clinical activity of ibrutinib was muted in WM patients harboring CXCR4 WHIM-mutations. Approximately 80% of relapsed/refractory WM patients who expressed CXCR4$^{WT}$ attained a major response, compared to 30% with CXCR4$^{WHIM}$ mutations following ibrutinib therapy. The finding that enhanced AKT and ERK activity following SDF-1a is present in CXCR4$^{S338X}$ expressing cells, and that inhibition of these targets potentiated ibrutinib killing provides support for an explanation for these clinical results, as well as a novel mechanism for ibrutinib related resistance. Consistent with these in vitro findings, robust pAKT staining was observed in tumor samples from CXCR4$^{WHIM}$ patients, which contrasted against marginal pAKT staining in tumor samples from CXCR4$^{WT}$ patients. Importantly, pAKT staining remained robust despite continuous ibrutinib therapy for 6 months in CXCR4$^{WHIM}$ patients, and continued to be marginal in CXCR4$^{WT}$ patients. Conversely, low level pERK staining was observed at baseline, and following ibrutinib therapy in bone marrow samples, without any discernible differences between CXCR4$^{WT}$ and CXCR4$^{WHIM}$ patients. These findings depict constitutive AKT activity, which functions as a powerful survival factor in WM, as being relevant to in vivo CXCR4$^{WHIM}$ signaling, and likely in view of the aggregate findings of this study as a likely contributor to clinical resistance to ibrutinib. The absence of pERK differences in patients with and without CXCR4$^{WHIM}$ mutations while a surprise could reflect either in vivo steady state attainment of pERK in response to SDF-1a, dependence of pERK signaling on other (non-CXCR4) triggered pathways, as well as micro-environmental effects which could modulate pERK activity.

The additional finding in these studies that SDF-1a protected against apoptosis triggered by other WM relevant therapeutics including bendamustine, fludarabine, bortezomib, and idelalisib in WM cells engineered to express the CXCR4$^{WHIM}$ mutation is of great interest, and demonstrates the relevance of these findings against a broader array of agents used to treat WM. Rescue effects by SDF-1a in CXCR4$^{S338X}$ expressing BCWM.1 and MWCL-1 cells were particularly pronounced against idelalisib, a novel PI3Kδ inhibitor that modulates AKT activity, and has shown promising activity in relapsed/refractory WM patients.

In conclusion, these findings show that the most common CXCR4 WHIM-like somatic mutation in WM (CXCR4$^{S338X}$) confers decreased SDF-1a triggered CXCR4 receptor internalization, enhanced AKT and ERK activation, and resistance to ibrutinib triggered apoptosis in WM cells. Use of inhibitors targeting CXCR4 or AKT/ERK can restore the sensitivity of CXCR4$^{S338X}$ expressing WM cells to ibrutinib as well as other WM relevant agents, thereby providing a framework for the investigation of these combinations in WM.

Figure 11A:
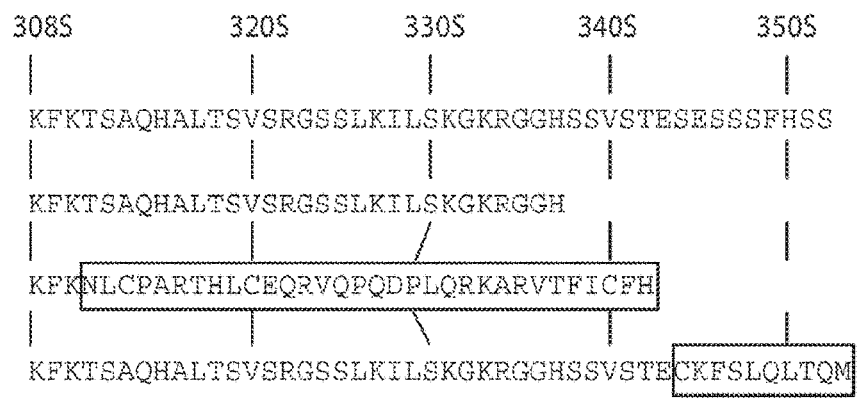
(FIG. 11A) Depiction of C-terminal domain of CXCR4 showing CXCR4$^{WT}$ (SEQ ID NO:13), CXCR4$^{T311fs}$ (SEQ ID NO:14), CXCR4$^{S344fs}$ (SEQ ID NO:15) and CXCR4$^{S338X}$ (SEQ ID NO:16) amino acid sequences. Highlighted amino acids denote novel predicted sequences resulting from frameshift mutations.
Figure 11B:
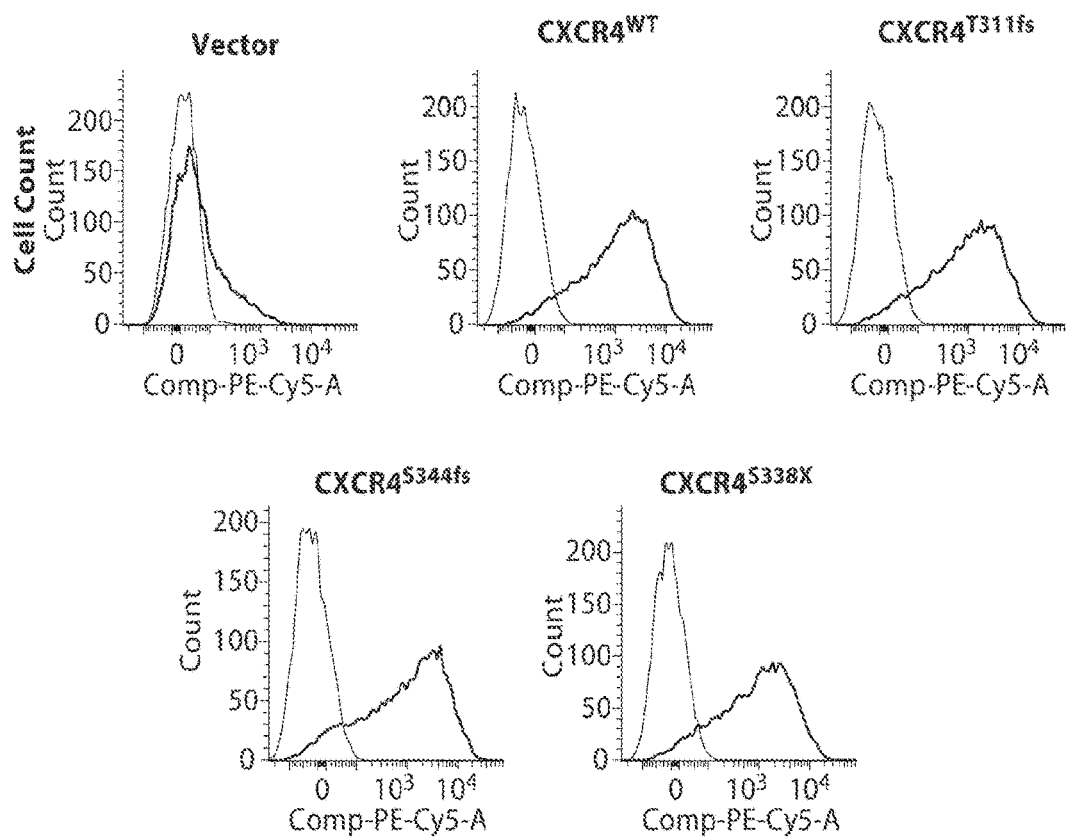
(FIG. 11B) Cell surface expression of CXCR4 in vector only, CXCR4$^{WT}$, CXCR4$^{T311fs}$, CXCR4$^{S344fs}$ and CXCR4$^{S338X}$ expressing BCWM.1 cells by flow cytometry using anti-CXCR4 mAb (12G5) (dark line) or isotype control (gray line).
Figure 11C:
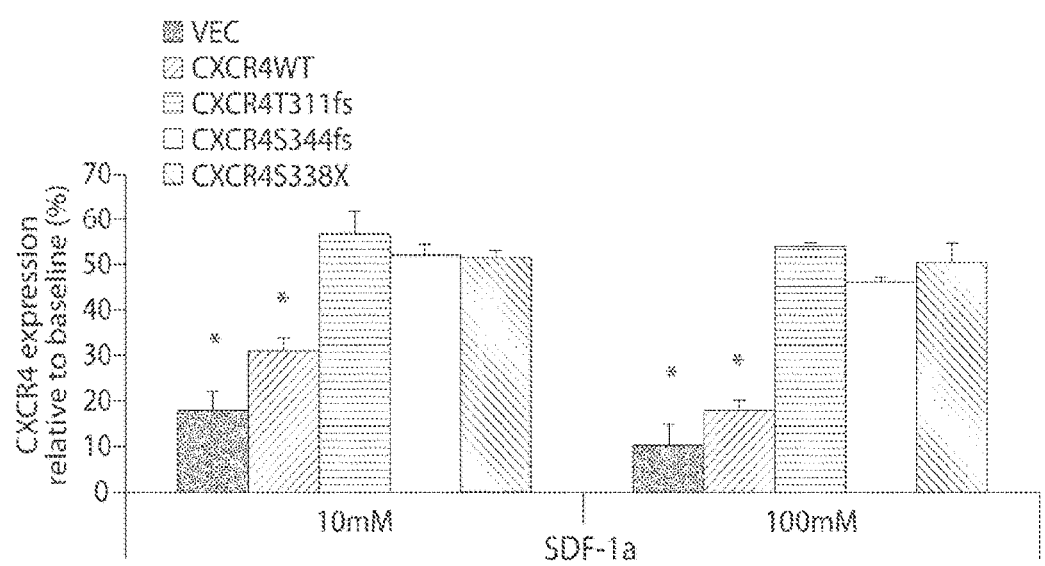
(FIG. 11C) Changes in cell surface CXCR4 expression following stimulation of vector only, CXCR4$^{WT}$, CXCR4$^{T311fs}$, CXCR4$^{S344fs}$ and CXCR4$^{S338X}$ expressing BCWM.1 cells for 30 minutes at 37° C. with SDF-1a (10 nM, 100 nM). Surface CXCR4 expression was assessed by flow cytometry and expression relative to baseline levels are shown. Data represent the median of at least 3 independent experiments; *p<0.05 for comparisons.

Example 6: CXCR4 WHIM-Like Frameshift Mutations Activate AKT and ERK, and Promote Resistance to Ibrutinib in Waldenstrom's Macroglobulinemia Cells Methods CXCR4$^{WT}$, CXCR4$^{FS}$, CXCR4$^{S338X}$ cDNAs were subcloned into plenti-IRES-GFP vector, and transduced using a lentiviral based strategy into BCWM.1 WM cells as before (Cao et al, 2014; Yang et al, 2013). Frameshift mutations proximal and distal to CXCR4$^{S338X}$ that were identified in WM patients by WGS were studied (FIG. 11). One frameshift variant resulted from insertion of T at position 136872570 resulting in T311fs; the other frameshift variant resulted from GAAGACTCAG>AC (SEQ ID NO:17) at position 136872467 resulting in S344fs. The nonsense mutation CXCR4$^{S338X}$ resulted from C>G change at 136872485 (Hunter et al, 2013). Five days after transduction, GFP positive cells were sorted and used for functional studies. Surface CXCR4 expression was determined at baseline, and following stimulation for 30 minutes with SDF-1a (10-100 nM) as before (Cao et al, 2014). Phosphoflow experiments were performed using conjugated antibodies to phospho-ERK1/2 ($T^{202}/Y^{204}$) and phospho-AKT($S^{473}$) (BD Phosflow) as previously described (Cao et al, 2014). Ibrutinib was obtained from MedChem Express (Monmouth Junction, N.J.). Cell signaling and survival studies related to CXCR4 signaling were performed in the presence or absence of SDF-1a (20-50 nM) and ibrutinib (5.0 uM). For survival studies, WM cells were incubated for 18 hours and apoptosis assessed by Annexin V staining (R&D Systems, Minneapolis Minn.) with BCL-2 inhibitor (GDC-0199; Selleck Chemicals Inc., Houston Tex.) to optimize ibrutinib related apoptotic effects in SDF-1a rescue experiments as previously described (Cao et al, 2014). Survival studies related to AKT and ERK were performed in the presence or absence AKT (MK-2206, 0.5 uM) or MEK (AS-703026, 0.25 uM) specific inhibitors (Selleck Chemicals, Houston Tex.) as previously reported (Cao et al, 2014).

Results

Non-transfected BCWM.1 cells express very low levels of CXCR4. BCWM.1 cells were transfected with vector alone, $CXCR4^{WT}$, as well as $CXCR4^{S338X}$, $CXCR4^{T311fs}$, and $CXCR4^{S344fs}$ expressing vectors. The predicted C-terminal amino acid sequences and truncation sites for the CXCR4 mutations evaluated in this study are shown in FIG. 11. Flow cytometry confirmed similar levels of CXCR4 cell surface expression for transfected cells (FIG. 11). Stimulation of transfected WM cells with SDF-1a for 30 minutes resulted in significantly greater internalization of CXCR4 expression on $CXCR4^{WT}$ versus $CXCR4^{S338X}$, $CXCR4^{T311fs}$, and $CXCR4^{S344fs}$ expressing WM cells ($p<0.05$; FIG. 11). Similar reduced levels of CXCR4 receptor internalization were observed for $CXCR4^{S338X}$, $CXCR4^{T311fs}$, and $CXCR4^{S344fs}$ expressing cells following SDF-1a stimulation.

Figure 12A:
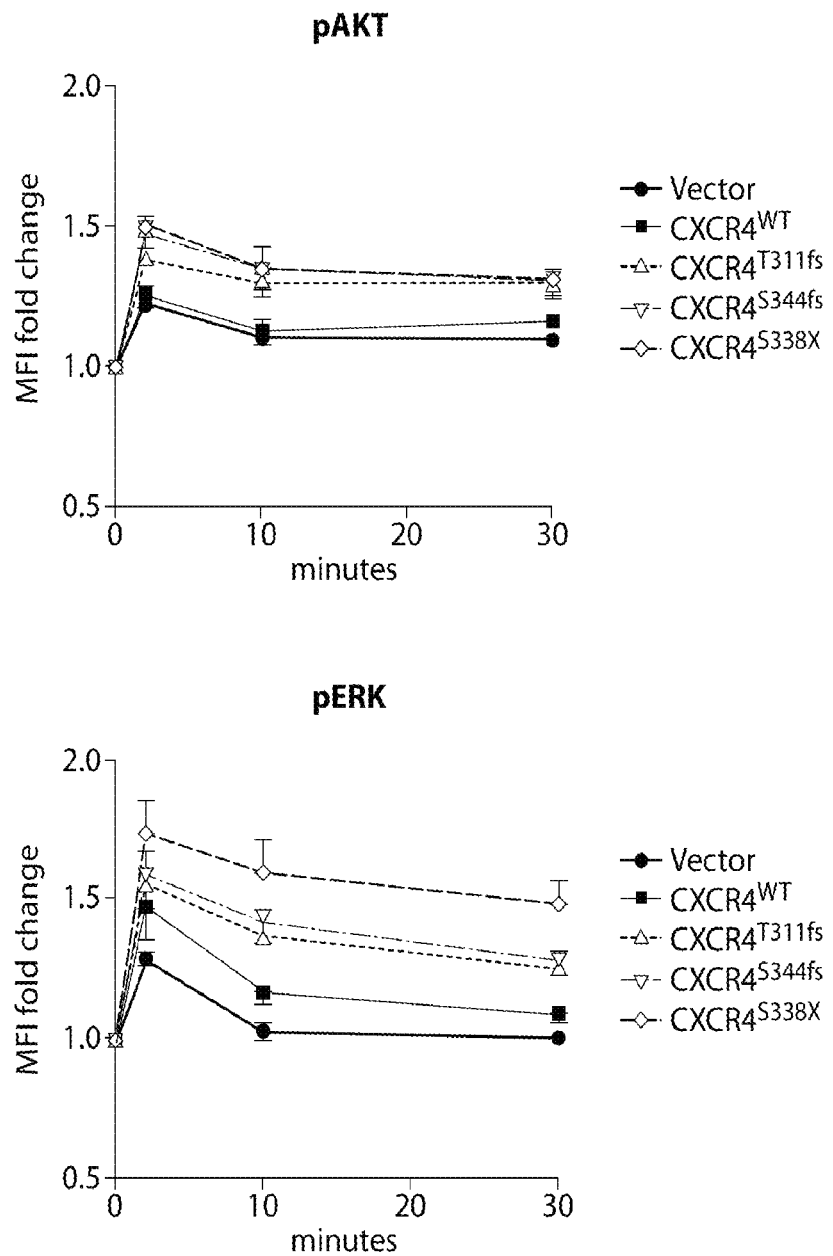
(FIG. 12A) CXCR4$^{T311fs}$ and CXCR4$^{S344fs}$ expressing WM cells were treated for 18 hours with vehicle control (DMSO); ibrutinib (IB; 0.5 uM) in the presence or absence of SDF-1a (SDF; 20 nM) and/or the AKT (MK-2206; 0.5 uM) and ERK (AZ-703026; 0.25 uM) inhibitors. Annexin V staining was performed to assess apoptosis. Study was performed in triplicate, and results from a representative study set are shown (FIG. 12B).
Figure 12B:
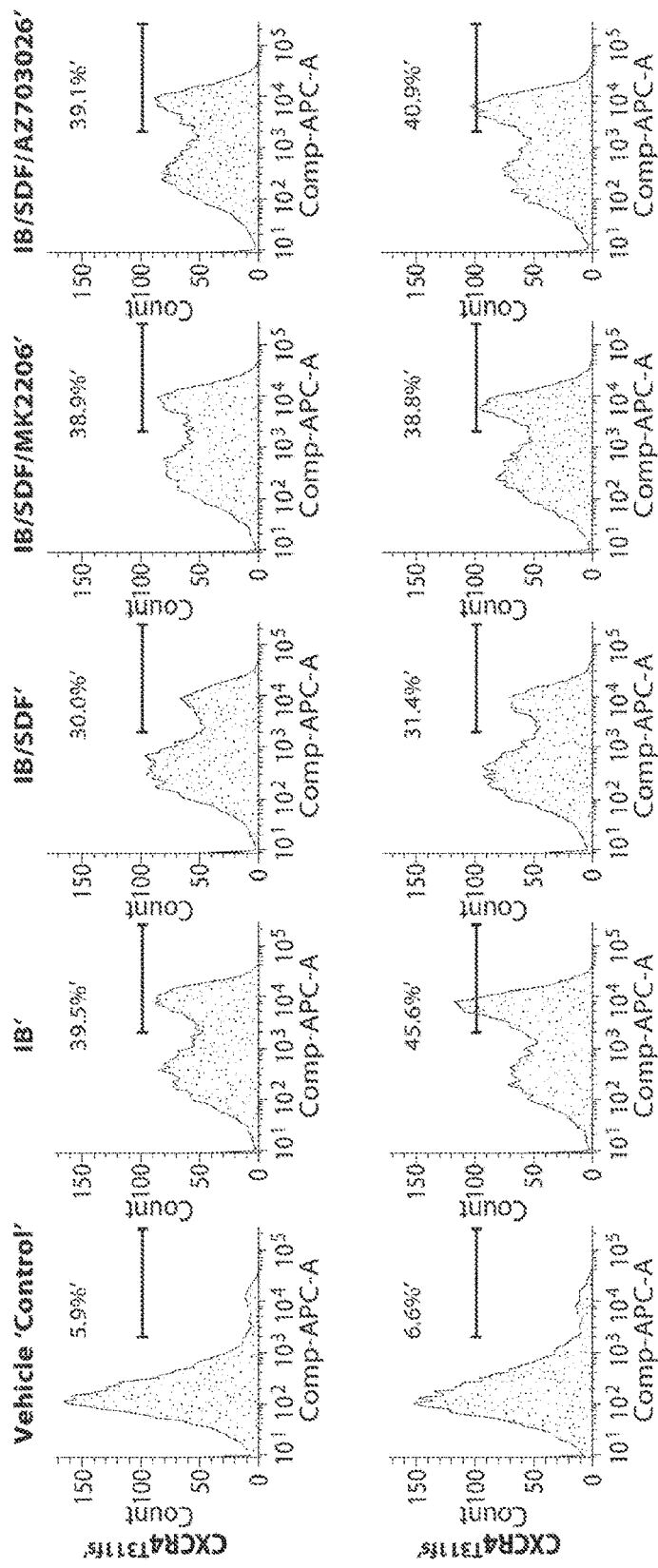
FIG. 12. Impact of SDF-1a on AKT and ERK signaling and WM cell survival in CXCR4 transfected WM cells. Vector only, CXCR4$^{WT}$, CXCR4$^{T311fs}$ CXCR4$^{S344fs}$ and CXCR4$^{S338X}$ expressing WM cells were treated with SDF-1a (20 nM) for 2, 15, and 30 minutes and phosphoflow analyses performed using phospho-AKT (S$^{473}$) or phospho-ERK (T$^{202}$/Y$^{204}$) directed antibodies. Data represent the mean of at least 3 experiments ±SEM; *p<0.05 for comparisons.

Because AKT and ERK are important survival factors in WM, as well as downstream mediators for CXCR4 signaling, their signaling was interrogated (Leleu et al, 2007; Busillo et al, 2007; Leleu et al, 2008). WM cells were stimulated with SDF-1a for 2, 15, and 30 minutes and evaluated by phosphoflow analysis. Stimulation with SDF-1a showed enhanced and prolonged AKT activation in $CXCR4^{S338X}$, $CXCR4^{T311fs}$, and $CXCR4^{S344fs}$ versus vector only and $CXCR4^{WT}$ expressing WM cells ($p<0.05$; FIG. 12). Levels of AKT activation were similar for $CXCR4^{FS}$ and $CXCR4^{S338X}$ cells. In contrast, intermediate levels of ERK activation between $CXCR4^{WT}$ and $CXCR4^{S338X}$ were observed for $CXCR4^{T311fs}$ and $CXCR4^{S344fs}$ expressing WM cells in response to SDF-1a ($p<0.05$ versus both $CXCR4^{WT}$ and $CXCR4^{S338X}$; FIG. 12). As with the previous findings in $CXCR4^{S338X}$ cells, use of AKT (MK-2206) or MEK (AS-703026) specific inhibitors attenuated SDF-1a rescue of ibrutinib or idelalisib treated $CXCR4^{T311fs}$ and $CXCR4^{S344fs}$ cells (FIG. 12)

Figure 13:
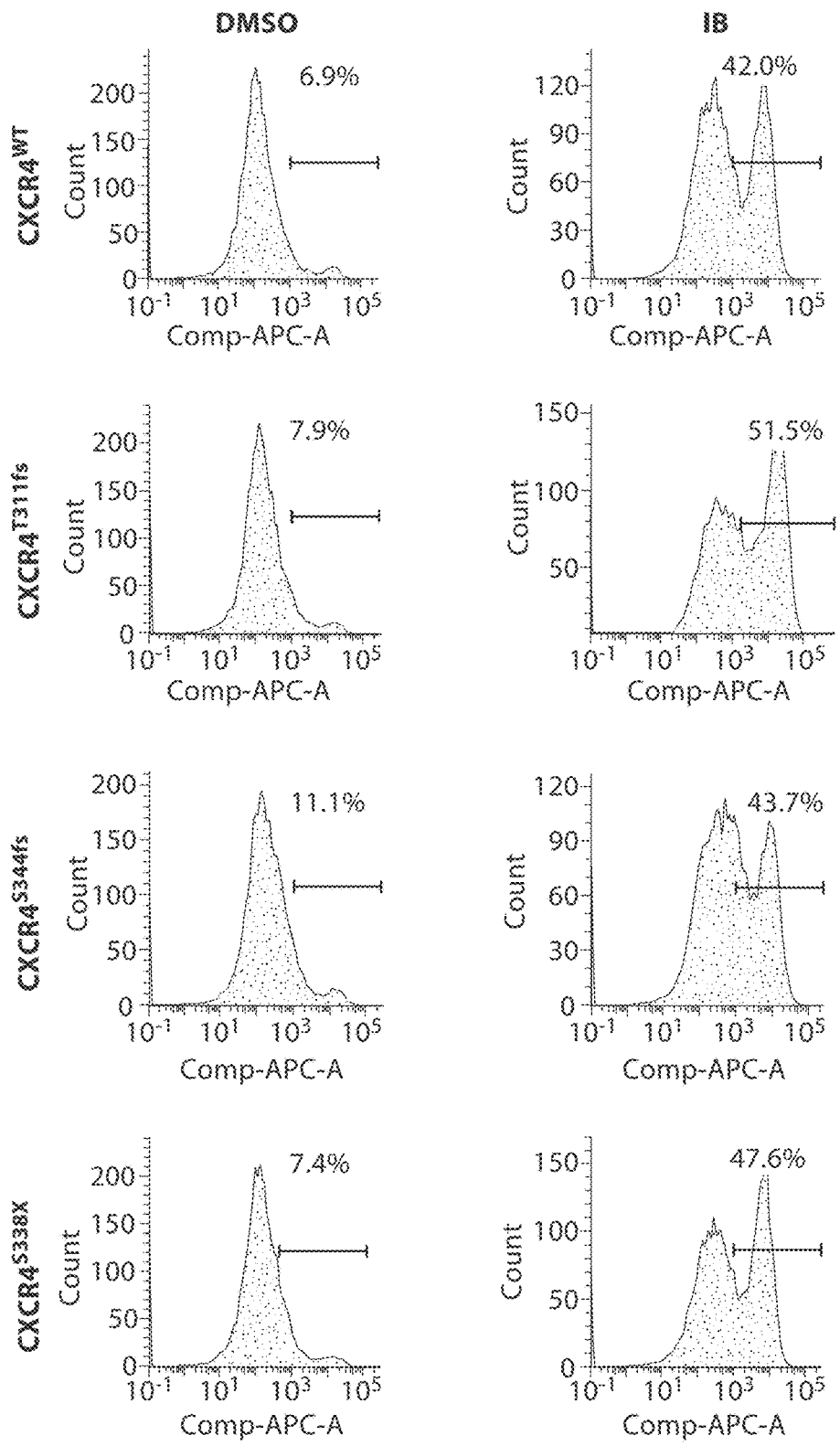
FIG. 13. Impact of SDF-1a and plerixafor on transfected WM cells treated with ibrutinib. CXCR4$^{WT}$ CXCR4$^{T311fs}$ CXCR4$^{S344fs}$ and CXCR4$^{S338X}$ expressing WM cells were treated for 18 hours with vehicle control (DMSO); ibrutinib (IB; 0.5 uM) in the presence or absence of SDF-1a (SDF; 20 nM) and/or the CXCR4 receptor antagonist plerixafor (PXF; 30 uM). Annexin V staining was performed to assess apoptosis. Study was performed in triplicate, and results from a representative study set are shown.
Figure 13:
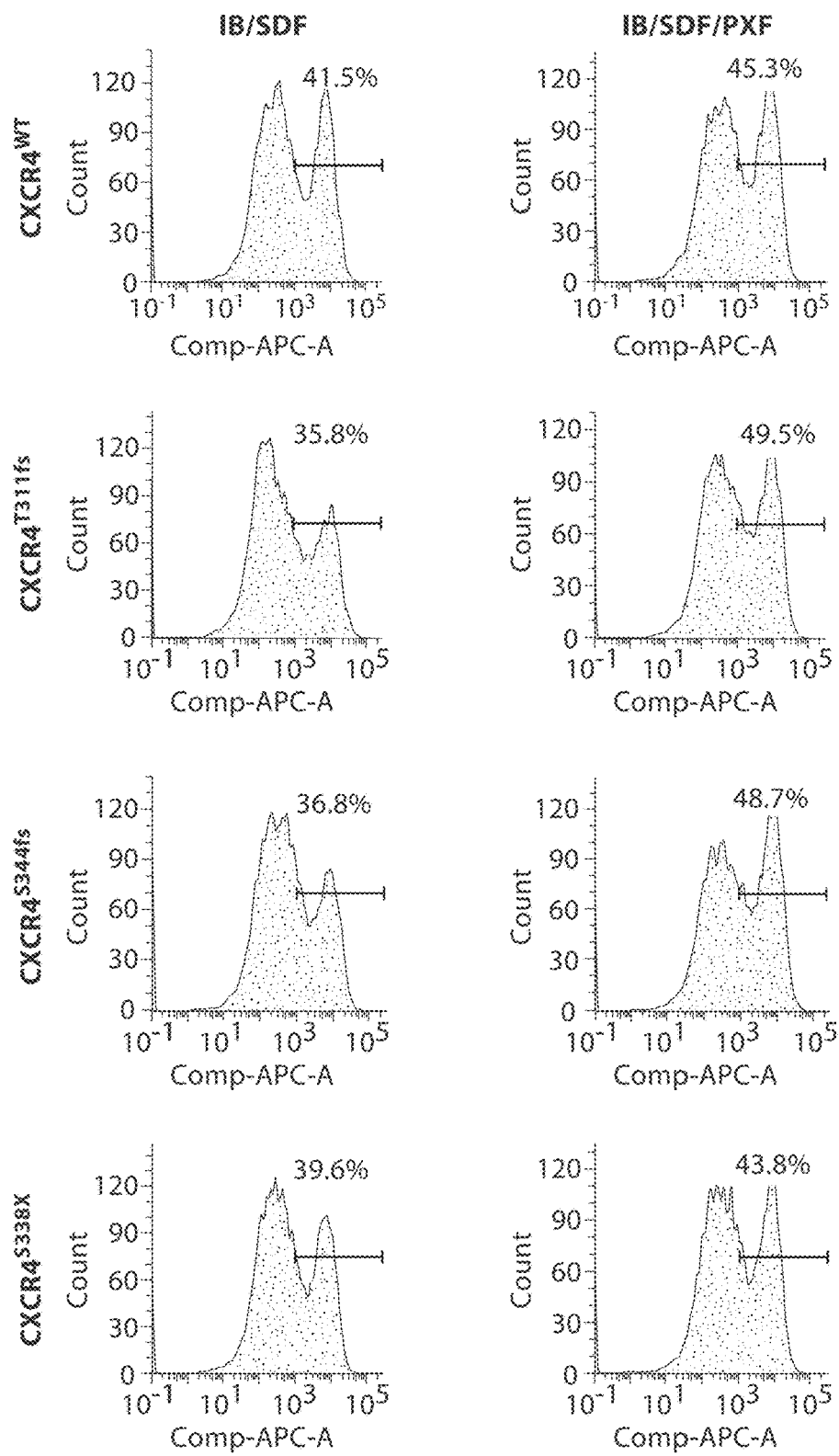

Since SDF-1a triggers the pro-survival proteins AKT and ERK, the pro-apoptotic effects of ibrutinib was examined on $CXCR4^{WT}$, $CXCR4^{S338X}$, $CXCR4^{T311fs}$ and $CXCR4^{S344fs}$ expressing WM cells in the presence or absence of SDF-1a and the CXCR4 antagonist plerixafor. $CXCR4^{WT}$, $CXCR4^{S338X}$, $CXCR4^{T311fs}$ and $CXCR4^{S344fs}$ expressing WM cells showed similar levels of apoptosis triggered by ibrutinib (FIG. 13). In contrast to $CXCR4^{WT}$ expressing cells, $CXCR4^{S338X}$ as well as $CXCR4^{T311fs}$ and $CXCR4^{S344fs}$ expressing WM cells showed similar levels of SDF-1a mediated rescue to ibrutinib triggered apoptosis. Concurrent treatment of SDF-1a exposed $CXCR4^{S338X}$, $CXCR4^{T311fs}$ and $CXCR4^{S344fs}$ cells with the CXCR4 antagonist plerixafor restored the pro-apoptotic effects of ibrutinib (FIG. 13).

Discussion

The functional significance of $CXCR4^{FS}$ mutations that constitute half of the WHIM-like somatic mutations in WM was investigated (Hunter et al, 2013; Treon et al, 2014). These studies show that $CXCR4^{FS}$ expressing cells exhibited diminished CXCR4 receptor internalization in response to SDF-1a akin to that observed for $CXCR4^{S338X}$ expressing cells. These findings are consistent with earlier work in WHIM patients establishing the terminal 10 amino acids as critical determinants of SDF-1a triggered CXCR4 receptor internalization (Futahashi et al, 2007). Particularly critical in this region are $Ser^{346/347}$ which are phosphorylated by GRK2/3, and required for subsequent phosphorylation of more proximal sites ($Ser^{324/325}$ and $Ser^{338/339}$) that regulate CXCR4 receptor internalization and desensitization (Mueller et al, 2013). As shown in FIG. 11, all three mutants examined here impact the $Ser^{346/347}$ site by introduction of a stop codon leading to its truncation ($CXCR4^{S338X}$); by frameshift mutation leading to a stop codon and truncation ($CXCR4^{T311fs}$); and by frameshift mutation resulting in replacement of amino acids ($CXCR4^{S344fs}$).

Both AKT and ERK are important survival factors in WM (Leleu et al, 2007; Leleu et al, 2008). AKT activation in $CXCR4^{FS}$ expressing cells showed increased and prolonged activation kinetics as those observed for $CXCR4^{S338X}$ cells. However, differences in ERK activation were observed between $CXCR4^{FS}$ and $CXCR4^{S338X}$ expressing cells, with lower levels of ERK activation observed for both $CXCR4^{T311fs}$ and $CXCR4^{S344fs}$ expressing cells versus $CXCR4^{S338X}$ cells. Differences in ERK activation may explain why WM patients with nonsense mutations inclusive of $CXCR4^{S338X}$ present with higher burdens of disease versus those with $CXCR4^{FS}$ mutations (Treon et al, 2014). ERK activation is dependent on binding of β-arrestins to the CXCR4 C-terminal domain which is prompted by recruitment of G protein-coupled receptor kinases (GRKs) in response to SDF-1a (Busillo et al, 2014). Loss of the distal C-terminal domain of WHIM patients sustains β-arrestin recruitment and ERK signaling (Busillo et al, 2014). Variations in ERK activation could therefore reflect differences in GRK phosphorylation and β-arrestin binding sites within the C-terminus.

Differences in heterodimer formation for $CXCR4^{FS}$ or $CXCR4^{S338X}$ with $CXCR4^{WT}$ proteins may also contribute to variations in downstream signaling following SDF-1a ligation. HEK cells transfected with both $CXCR4^{WT}$ and $CXCR4^{S338X}$ expressing vectors show preferential existence of heterodimers (Lagane et al, 2008). Novel amino acid sequences introduced by frameshift mutations into the C-terminal domain could be more disruptive than truncations introduced by nonsense mutations, thereby differentially impacting CXCR4 dimer formation and downstream signaling. More work is clearly needed to clarify such possibilities.

SDF-1a triggered AKT and ERK activation impacts ibrutinib triggered apoptosis in WM cells engineered to express $CXCR4^{S338X}$, as well as other agents used in WM therapy. These studies demonstrate that $CXCR4^{FS}$ mutations conferred SDF-1a mediated resistance to ibrutinib similar to that observed in $CXCR4^{S338X}$ expressing WM cells. Taken together, these findings provide a molecular basis for the diminished clinical activity of ibrutinib observed in WM patients bearing both nonsense and frameshift mutations (Treon et al, 2013). Moreover these findings also demonstrate that CXCR4 inhibitors can restore sensitivity to ibrutinib, as well as other therapeutics impacted by CXCR4$^{FS}$ mutations. Plerixafor, an FDA approved agent for stem cell mobilization in lymphoma patients, reversed myelokathexis related leukopenia in WHIM patients treated daily for 6 months, thereby demonstrating both clinical efficacy and long term safety of CXCR4 inhibition (McDermott et al, 2014). Several other antagonists to CXCR4 including BMS-936564, AMD-070, TG-0054 are also in clinical trials.

In conclusion, these findings show that CXCR4$^{FS}$ mutations confer decreased SDF-1a triggered CXCR4 receptor internalization, enhanced AKT and ERK activation, and SDF-1a mediated resistance to ibrutinib triggered apoptosis in WM cells. Use of inhibitors targeting CXCR4 restored the sensitivity of CXCR4$^{FS}$ expressing WM cells to ibrutinib thereby providing a framework for the investigation of CXCR4 antagonists with ibrutinib in WM patients with CXCR4$^{FS}$ mutations.

REFERENCES

1. Hunter Z R, Xu L, Yang G, Zhou Y, Liu X, Cao Y, et al. The genomic landscape of Waldenstöm's Macroglobulinemia is characterized by highly recurring MYD88 and WHIM-like CXCR4 mutations, and small somatic deletions associated with B-cell lymphomagenesis. Blood 2013 Dec. 23. [Epub ahead of print].
2. Treon S P, Cao Y, Xu L, Yang G, Liu X, Hunter Z R. Somatic mutations in MYD88 and CXCR4 are determinants of clinical presentation and overall survival in Waldenstrom's Macroglobulinemia. Blood 2014; [Epub ahead of print].
3. Treon S P, Xu L, Yang G, Zhou Y, Liu X, Cao Y, et al: MYD88 L265P somatic mutation in Waldenstrom's macroglobulinemia. N Engl J Med 2012; 367: 826-33.
4. Dotta L, Tassone L, Badolato R. Clinical and genetic features of Warts, Hypogammaglobulinemia, Infections and Myelokathexis (WHIM) syndrome. Curr Mol Med. 2011; 11: 317-25.
5. Ngo H T, Leleu X, Lee J, Jia X, Melhem M, Runnels J, et al. SDF-1/CXCR4 and VLA-4 interaction regulates homing in Waldenstrom macroglobulinemia. Blood. 2008; 112: 150-8.
6. Cao Y, Hunter Z R, Liu X, et al. The WHIM-like CXCR4$^{S338X}$ somatic mutation activates AKT and ERK, and promotes resistance to ibrutinib and other agents used in the treatment of Waldenstrom's Macroglobulinemia. Leukemia 2014; [Epub ahead of print].
7. Rocarro A M, Saco A, Jimenez C, et al. C1013G/CXCR4 acts as a driver mutation of tumor progression and modulator of drug resistance in lymphoplasmacytic lymphoma. Blood 2014; [Epub ahead of print].
8. Treon S P, Tripsas C, Yang G, Cao Y, Xu L, Hunter Z R, et al. A Prospective Multicenter Study Of The Bruton's Tyrosine Kinase Inhibitor Ibrutinib In Patients With Relapsed Or Refractory Waldenstrom's Macroglobulinemia. Proc. of the American Society of Hematology. Blood 2013; 122 (21): 251.
9. Owen R G, Treon S P, Al-Katib A, et al. Clinicopathological definition of Waldenström's macroglobulinemia: Consensus panel recommendations from the Second International Workshop on Waldenström's Macroglobulinemia. Semin Oncol. 2003; 30: 110-115.
10. Xu L, Hunter Z, Yang G, et al. MYD88 L265P in Waldenstrom macroglobulinemia, immunoglobulin M monoclonal gammopathy, and other B-cell lymphoproliferative disorders using conventional and quantitative allele-specific polymerase chain reaction. Blood 2013; 121(11):2051-8.
11. Xu L, Hunter Z, Yang G, et al. Detection of MYD88 L265P in peripheral blood from patients with Waldenström's Macroglobulinemia and IgM Monoclonal Gammopathy of Undetermined Significance. Leukemia 2014; [Epub ahead of print].
12. Treon S P, Hunter Z R. A new era for Waldenstrom macroglobulinemia: MYD88 L265P. Blood 2013; 121: 4434-6.
13. Landgren O, Staudt L. MYD88 L265P Somatic Mutation in IgM MGUS. N Engl J Med 2012; 367:2255-57.
14. Varettoni M, Arcaini L, Zibellini S, Boveri E, Rattotti S, Pascutto C, et al: Prevalence and clinical significance of the MYD88 (L265P) somatic mutation in Waldenstrom's macroglobulinemia and related lymphoid neoplasms. Blood 2013; 121:2522-8.
15. Jimenez C, Sebastian E, Del Carmen Chillón M, et al. MYD88 L265P is a marker highly characteristic of, but not restricted to, Waldenström's macroglobulinemia. Leukemia 2013; 27(8):1722-8.
16. Martinez N, Almaraz C, Vaque J P, et al. Whole-exome sequencing in splenic marginal zone lymphoma reveals mutations in genes involved in marginal zone differentiation. Leukemia 2014; 28:1334-40.
17. Ngo V N, Young R M, Schmitz R, et al. Oncogenically active MYD88 mutations in human lymphoma. Nature. 2011; 470(7332): 115-121.
18. Trøen G, Warsame A, Delabie J. CD79B and MYD88 Mutations in Splenic Marginal Zone Lymphoma. ISRN Oncol 2013; 2013:252318.
19. Swerdlow, S H, Campo, E, Harris, N L, et al. (eds). World Health Organization Classification of Tumours of Haematopoietic and Lymphoid Tissues (4$^{th}$ edition). Lyon, France. IARC Press, 2008:194-5.
20. Kyrtsonis M C, Levidou G, Korkolopoulou P, et al. CD138 expression helps distinguish Waldenstrom's macroglobulinemia from splenic marginal zone lymphoma. Clin Lymph Myel Leuk. 2011; 11: 99-102.
21. Arcaini L, Varettoni M, Boveri E, et al. Distinctive clinical and histological features of Waldenstrom's Macroglobulinemia and splenic marginal zone lymphoma. Clin Lymph Myel Leuk. 2011; 11: 103-105.
22. Treon S P, Xu L, Yang G, Zhou Y, Liu X, Cao Y, et al: MYD88 L265P somatic mutation in Waldenstrom's macroglobulinemia. N Engl J Med 2012; 367(9):826-33.
23. Hunter Z R, Xu L, Yang G, Zhou Y, Liu X, Cao Y, et al. The genomic landscape of Waldenström's Macroglobulinemia is characterized by highly recurring MYD88 and WHIM-like CXCR4 mutations, and small somatic deletions associated with B-cell lymphomagenesis. Blood 2013 Dec. 23. [Epub ahead of print].
24. Xu L, Hunter Z R, Yang G, Zhou Y, Cao Y, Liu X, et al: MYD88 L265P in Waldenstrom macroglobulinemia, immunoglobulin M monoclonal gammopathy, and other B-cell lymphoproliferative disorders using conventional and quantitative allele-specific polymerase chain reaction. Blood 2013; 121:2051-8.
25. Varettoni M, Arcaini L, Zibellini S, Boveri E, Rattotti S, Pascutto C, et al: Prevalence and clinical significance of the MYD88 (L265P) somatic mutation in Waldenstrom's macroglobulinemia and related lymphoid neoplasms. Blood 2013; 121:2522-8.
26. Jimenez C, Sebastian E, Del Carmen Chillon M, Giraldo P, Mariano Hernandez J, Escalante F, et al: MYD88 L265P is a marker highly characteristic of, but not 26. restricted to, Waldenstrom's macroglobulinemia. Leukemia 2013; August; 27(8):1722-8.
27. Poulain S, Roumier C, Decambron A, Renneville A, Herbaux C, Bertrand E, et al. MYD88 L265P mutation in Waldenstrom's macroglobulinemia. Blood 2013; May 30; 121(22):4504-11.
28. Roccaro A, Sacco A, Jiminez C, Maiso P, Moschetta M, Mishima Y, et al. A novel activating mutation of CXCR4 plays a crucial role in Waldenstrom Macroglobulinemia biology. Blood 2013; 122(21): Abstract 272.
29. Treon S P, Cao Y, Xu L, Yang G, Liu X, Hunter Z R. Somatic mutations in MYD88 and CXCR4 are determinants of clinical presentation and overall survival in Waldenstrom's Macroglobulinemia. Blood 2014; [Epub ahead of print].
30. Yang G, Zhou Y, Liu X, Xu L, Cao Y, Manning R J, et al. A mutation in MYD88 (L265P) supports the survival of lymphoplasmacytic cells by activation of Bruton tyrosine kinase in Waldenstrom macroglobulinemia. Blood. 2013; 122(7):1222-32.
31. Dotta L, Tassone L, Badolato R. Clinical and genetic features of Warts, Hypogammaglobulinemia, Infections and Myelokathexis (WHIM) syndrome. Curr Mol Med. 2011; 11(4):317-25.
32. Busillo J M, Benovic J L. Regulation of CXCR4 signaling. Biochim Biophys. Acta 2007; 1768(4):952-963.
33. Busillo J M, Amando S, Sengupta R, Meucci O, Bouvier M, Benovic J L. Site-specific phosphorylation of CXCR4 is dynamically regulated by multiple kinases and results in differential modulation of CXCR4 signaling. J Biol Chem 2010; 285(10):7805-17.
34. Bam R, Ling W, Khan S, Pennisi A, Venkateshaiah S U, Li X, et al. Role of Bruton's tyrosine kinase in myeloma cell migration and induction of bone disease. Am J Hematol 2013; 88(6):463-71.
35. Ngo H T, Leleu X, Lee J, Jia X, Melhem M, Runnels J, et al. SDF-1/CXCR4 and VLA-4 interaction regulates homing in Waldenstrom macroglobulinemia. Blood. 2008; 112(1):150-8.
37. Herman S E, Gordon A L, Hertlein E, Ramanunni A, Zhang X, Jaglowski S, et al. Bruton tyrosine kinase represents a promising therapeutic target for treatment of chronic lymphocytic leukemia and is effectively targeted by PCI-32765. Blood 2011; 117(23):6287-96.
38. Davies B R, Greenwood H, Dudley P, Crafter C, Yu D H, Zhang J, et al. Preclinical Pharmacology of AZD5363, an Inhibitor of AKT: Pharmacodynamics, Antitumor Activity, and Correlation of Monotherapy Activity with Genetic Background. Mol Cancer Ther 2012; 11(4):873-87.
39. Okuzumi T, Fiedler D, Zhang C, Gray D C, Aizenstein B, Hoffman R, Shokat K M. Inhibitor hijacking of Akt activation. Nat Chem Biol 2009; 5(7):484-93.
40. Treon S P, Tripsas C, Yang G, Cao Y, Xu L, Hunter Z R, et al. A Prospective Multicenter Study Of The Bruton's Tyrosine Kinase Inhibitor Ibrutinib In Patients With Relapsed Or Refractory Waldenstrom's Macroglobulinemia. Proc. of the American Society of Hematology. Blood 2013; 122 (21): 251.
41. Leleu X, Jia X, Runnels J, Ngo H T, Moreau A S, Farag M, et al. The Akt pathway regulates survival and homing in Waldenstrom macroglobulinemia. Blood 2007; 110 (13):4417-26.
42. Tai Y T, Chang B Y, Kong S Y, Fulciniti M, Yang G, Calle Y, et al. Bruton tyrosine kinase inhibition is a novel therapeutic strategy targeting tumor in the bone marrow microenvironment in multiple myeloma. Blood 2012; 120(9):1877-87.
43. Leleu X, Eeckhoute J, Jia X, Roccaro A M, Moreau A S, Farag M, et al. Targeting NF-kappaB in Waldenstrom macroglobulinemia. Blood 2008; 111(10):5068-77.
44. McDermott D H, Lopez J, Deng F, Liu Q, Ojode T, Chen H, et al. AMD3100 is a potent antagonist at CXCR4 (R334X), a hyperfunctional mutant chemokine receptor and cause of WHIM syndrome. J Cell Mol Med 2011; 15(10):2071-81.
45. McDermott D H, Liu Q, Ulrick J, Kwatemaa N, Anaya-O'Brien S, Penzak S R, et al. The CXCR4 antagonist plerixafor corrects panleukopenia in patients with WHIM syndrome. Blood 2011; 118(18):4957-62.
46. Balabanian K, Lagane B, Pablos J L, Laurent L, Planchenault T, Verola O, et al. WHIM syndromes with different genetic anomalies are accounted for by impaired CXCR4 desensitization to CXCL12. Blood 2005; 105: 2449-2457.
47. Leleu X, Jia X, Runnels J, Ngo H T, Moreau A S, Farag M, et al. The Akt pathway regulates survival and homing in Waldenstrom Macroglobulinemia. Blood 2007; 110 (13):4417-26.
48. Gopal A K, Kahl B S, de Vos S, Wagner-Johnston N D, Schuster S J, Jurczak W J, Flinn I W, et al. PI3Kδ inhibition by idelalisib in patients with relapsed indolent lymphoma. N Engl J Med 2014; 370(11):1008-18.
49. Busillo J M, Benovic J L. Regulation of CXCR4 signaling. Biochim Biophys. Acta 2007; 1768(4):952-963.
50. Busillo J M, Armando S, Sengupta R, et al. Site-specific phosphorylation of CXCR4 is dynamically regulated by multiple kinases and results in differential modulation of CXCR4 signaling. J Biol Chem. 2010; 285(10):7805-17.
51. Cao Y, Hunter Z R, Liu X, et al. The WHIM-like $CXCR4^{S338X}$ somatic mutation activates AKT and ERK, and promotes resistance to ibrutinib and other agents used in the treatment of Waldenstrom's Macroglobulinemia. Leukemia 2014; [Epub ahead of print].
52. Dotta L, Tassone L, Badolato R. Clinical and genetic features of Warts, Hypogammaglobulinemia, Infections and Myelokathexis (WHIM) syndrome. Curr Mol Med. 2011; 11(4):317-25.
53. Futahashi Y, Koman J, Urano E, et al. Separate elements are required for ligand-dependent and independent internalization of metastatic potentiator CXCR4. Cancer Sci 2007; 98: 373-9.
54. Hunter Z R, Xu L, Yang G, Zhou Y, Liu X, Cao Y, et al. The genomic landscape of Waldenström's Macroglobulinemia is characterized by highly recurring MYD88 and WHIM-like CXCR4 mutations, and small somatic deletions associated with B-cell lymphomagenesis. Blood 2013 Dec. 23. [Epub ahead of print].
55. Lagane B, Chow K Y C, Balabanian K, et al. CXCR4 dimerization and β-arrestin mediated signaling account for the enhanced chemotaxis to CXCL12 in WHIM syndrome. Blood 2008; 112:34-44.
56. Leleu X, Jia X, Runnels J, Ngo H T, Moreau A S, Farag M, et al. The Akt pathway regulates survival and homing in Waldenstrom macroglobulinemia. Blood 2007; 110 (13):4417-26.
57. Leleu X, Eeckhoute J, Jia X, Roccaro A M, Moreau A S, Farag M, et al. Targeting NF-kappaB in Waldenstrom macroglobulinemia. Blood 2008; 111(10):5068-77.

58. McDermott D H1, Liu Q, Velez D, et al. A phase 1 clinical trial of long-term, low-dose treatment of WHIM syndrome with the CXCR4 antagonist plerixafor. Blood. 2014; 123(15):2308-16.
59. Mueller W, Schutz D, Nagel F, et al. Hierarchical organization of multisite phosphorylation at the CXCR4 C terminus. PLOS One 2013; 8:e64975.
60. Roccaro A, Sacco A, Jiminez C, Maiso P, Moschetta M, Mishima Y, et al. A novel activating mutation of CXCR4 plays a crucial role in Waldenstrom Macroglobulinemia biology. Blood 2013; 122(21): Abstract 272.
61. Treon S P, Xu L, Yang G, Zhou Y, Liu X, Cao Y, et al: MYD88 L265P somatic mutation in Waldenstrom's macroglobulinemia. N Engl J Med 2012; 367(9):826-33.
62. Treon S P, Tripsas C, Yang G, Cao Y, Xu L, Hunter Z R, et al. A Prospective Multicenter Study Of The Bruton's Tyrosine Kinase Inhibitor Ibrutinib In Patients With Relapsed Or Refractory Waldenstrom's Macroglobulinemia. Proc. of the American Society of Hematology. Blood 2013; 122 (21): 251.
63. Treon S P, Cao Y, Xu L, Yang G, Liu X, Hunter Z R. Somatic mutations in MYD88 and CXCR4 are determinants of clinical presentation and overall survival in Waldenstrom's Macroglobulinemia. Blood 2014; [Epub ahead of print].
64. Yang G, Zhou Y, Liu X, Xu L, Cao Y, Manning R J, et al. A mutation in MYD88 (L265P) supports the survival of lymphoplasmacytic cells by activation of Bruton tyrosine kinase in Waldenstrom macroglobulinemia. Blood 2013; 122:1222-32.

We claim:

1. A method for treating a subject having Waldenstrom's macroglobulinemia, the method comprising:
   obtaining diseased B cells from the subject, and
   performing an assay on the diseased B cells to determine whether the diseased B cells contain a mutation in the carboxyl-terminal cytoplasmic tail of the gene encoding CXCR4, and
   if the subject has a mutation in the carboxyl-terminal cytoplasmic tail of the gene encoding CXCR4, then administering to the subject an effective amount of (i) an anti-cancer agent for Waldenstrom's macroglobulinemia that is not a BTK inhibitor or (ii) a BTK inhibitor in combination with a CXCR4 inhibitor, an AKT inhibitor and/or an ERK inhibitor; or
   if the subject does not have a mutation in the carboxyl-terminal cytoplasmic tail of the gene encoding CXCR4, then administering to the subject an effective amount of an anti-cancer agent for Waldenstrom's macroglobulinemia.

2. A method for treating a subject having Waldenstrom's macroglobulinemia, the method comprising:
   directing a test on diseased B cells obtained from the subject to determine whether the diseased B cells contain a mutation in the carboxyl-terminal cytoplasmic tail of the gene encoding CXCR4, and
   if the subject has a mutation in the carboxyl-terminal cytoplasmic tail of the gene encoding CXCR4, then administering to the subject an effective amount of (i) an anti-cancer agent for Waldenstrom's macroglobulinemia that is not a BTK inhibitor or (ii) a BTK inhibitor in combination with a CXCR4 inhibitor, an AKT inhibitor and/or an ERK inhibitor; or
   if the subject does not have a mutation in the carboxyl-terminal cytoplasmic tail of the gene encoding CXCR4, then administering to the subject an effective amount of an anti-cancer agent for Waldenstrom's macroglobulinemia.

3. A method for treating a subject with Waldenstrom's macroglobulinemia, the method comprising:
   (a) selecting the subject on the basis that the subject is known to have contain a mutation in the carboxyl-terminal cytoplasmic tail of the gene encoding CXCR4; and
   (b) administering an effective amount of (i) an anti-cancer agent that is not a BTK inhibitor or (ii) a BTK inhibitor in combination with a CXCR4 inhibitor, an AKT inhibitor and/or an ERK inhibitor, to the subject because the subject has a mutation in the carboxyl-terminal cytoplasmic tail of the gene encoding CXCR4.

4. The method of claim 1, wherein:
   (i) the anti-cancer agent is an alkylator, an anthracycline, a nucleoside analogs, an anti-CD20 monoclonal antibody, thalidomide, an immunomodulatory derivative of thalidomide, interferon, a proteasome inhibitor, a protein kinase C inhibitor, a monoclonal antibody to CD52 and a microtubule inhibitor; or
   (ii) the anti-cancer agent is one or more of chlorambucil, Carmustine (bis-chloroethylnitrosourea), cyclophosphamide, vincristine, melphalan, prednisone, cladribine (2-chlorodeoxyadenosine), adriamycin, and dexamethasone.

5. The method of claim 4, wherein the anti-cancer agent is chlorambucil, cyclophosphamide, carfilzomib, oprozomib, ixazomib, cladribine (2-chlorodeoxyadenosine), adriamycin, rituximab, or alpha-interferon (a-IFN).

6. A method for treating a subject who has Waldenstrom's macroglobulinemia comprising administering to a human subject in need of such treatment a BTK inhibitor in an amount effective to treat the Waldenstrom's macroglobulinemia, wherein the subject has wild-type CXCR4.

7. The method of claim 1, further comprising performing an assay on a biological sample from a subject in need thereof to determine whether the subject has a mutation at position 38182641 in chromosome 3p22.2.

8. The method of claim 1, wherein the assay to determine whether the disease B cells contain a mutation in the carboxyl-terminal cytoplasmic tail of the gene encoding CXCR4 comprises allele specific polymerase chain reaction.

9. The method of claim 4, wherein the anti-CD20 monoclonal antibody is rituximab.

10. The method of claim 4, wherein the interferon is alpha-interferon.

11. The method of claim 4, wherein the proteasome inhibitor is carfilzomib, oprozomib, or ixazomib.

12. The method of claim 4, wherein the protein kinase C inhibitor is UCN-01.

13. The method of claim 4, wherein the monoclonal antibody to CD52 is alemtuzumab.

14. The method of claim 4, wherein the microtubule inhibitor is dolastatin.

15. The method of claim 7, wherein the assay to determine whether the subject has a mutation at position 38182641 in chromosome 3p22.2 comprises allele specific polymerase chain reaction performed using an allele specific primer, wherein the allele specific primer hybridizes at or near its 3' end to the mutation at position 38182641 in chromosome 3p22.2.

16. The method of claim 1, wherein the subject has a mutation in the carboxyl-terminal cytoplasmic tail of the gene encoding CXCR4 and a BTK inhibitor in combination with a CXCR4 inhibitor, an AKT inhibitor and/or an ERK inhibitor is administered to the subject.

17. The method of claim 2, wherein the subject has a mutation in the carboxyl-terminal cytoplasmic tail of the gene encoding CXCR4 and a BTK inhibitor in combination with a CXCR4 inhibitor, an AKT inhibitor and/or an ERK inhibitor is administered to the subject.

18. The method of claim 3, comprising administering an effective amount of a BTK inhibitor in combination with a CXCR4 inhibitor, an AKT inhibitor and/or an ERK inhibitor.

19. The method of claim 1, wherein the anti-cancer agent for Waldenstrom's macroglobulinemia administered if the subject does not have a mutation in the carboxyl-terminal cytoplasmic tail of the gene encoding CXCR4 is a BTK inhibitor.

20. The method of claim 19, wherein the BTK inhibitor is Ibrutinib.

21. The method of claim 2, wherein the anti-cancer agent for Waldenstrom's macroglobulinemia administered if the subject does not have a mutation in the carboxyl-terminal cytoplasmic tail of the gene encoding CXCR4 is a BTK inhibitor.

22. The method of claim 21, wherein the BTK inhibitor is Ibrutinib.

\* \* \* \* \*